United States Patent [19]

Shoelson

[11] Patent Number: 5,801,149
[45] Date of Patent: Sep. 1, 1998

[54] INHIBITION OF SIGNAL TRANSDUCTION MOLECULES

[75] Inventor: Steven Shoelson, Natick, Mass.

[73] Assignee: Joslin D-abetes Center, Inc., Boston, Mass.

[21] Appl. No.: 408,604

[22] Filed: Mar. 21, 1995

Related U.S. Application Data

[63] Continuation-in-part of Ser. No. 134,558, Oct. 8, 1993, abandoned, which is a continuation-in-part of Ser. No. 959,949, Oct. 9, 1992, abandoned, which is a continuation-in-part of Ser. No. 722,359, Jun. 19, 1991, abandoned.

[51] Int. Cl.$^6$ .......................... A61K 38/00; A61K 38/04; C07K 5/00
[52] U.S. Cl. ................. 514/18; 514/13; 514/14; 514/15; 514/16; 514/17; 514/324; 514/325; 530/330
[58] Field of Search ........................ 514/13, 14, 15, 514/16, 17, 18; 530/324, 325, 326, 327, 328, 329, 330, 331

[56] References Cited

PUBLICATIONS

Waksman, G. et al. Cell, 12, 779–790, Mar. 1993.

Cantley et al., "Oncogenes and Signal Transduction" *Cell*, vol. 64, No. 2, pp. 281–302, 25 Jan. 1991.

Chavanieu et al., "Phosphorylation Effects on Flanking Charged Residues: Sturctural Implications for Signal Transduction in Protein Kinases" *Eur. J. Biochem*, vol. 224, No. 1, pp. 115–123, 1994.

Cheng et al., "Peptide antibodies to the human c–fyn gene product demonstrate pp59$^{c-fyn}$ is capable of complex formation with the middle–T antigen of polyomavirus" *EMBO Journal*, vol. 7, No. 12, pp. 3845–3855, 1 Dec. 1988.

Escobedo et al., "cDNA Cloning of a Novel 85 kd Protein That Has SH2 Domains and Regulates Binding of P–13–Kinase to the PDGF β–Receptor" *Cell*, vol. 65, No. 1, pp. 75–82, 5 Apr. 1991.

Panchamoorthy et al., "Physical and Functional Interactions between SH2 and SH3 Domains of the Src Family Protein Tyrosine Kinase p59$^{fyn}$" *Molecular and Cellular Biology*, vol. 14, No. 9, pp. 6372–6385, Sep. 1994.

Shoelson et al., "Nonphosphorylatable Substrate Analogs Selectively Block Autophosphorylation and Activation of the Insulin Receptor, Epidermal Growth Factor Receptor, and pp60$^{v-src}$ Kinases" *Journal of Biological Chemistry*, vol. 264, No. 14, pp. 7831–7836, 15 May 1989.

Anderson, D. et al., "Binding of SH2 Domains of Phospholipase Cγ1, GAP, and Src to Activated Growth Factor Receptors" *Science*, vol. 250, No. 4983, pp. 979–982, 16 Nov. 1990.

Anderson, N.G. et al., "Requirement for integration of signals from two distinct phosphorylation pathways for activation of MAP kinase" *Nature*, vol. 343, No. 6259, pp. 651–653, 15 Feb. 1990.

Auger et al., "PDGF–Dependent Tyrosine Phosphorylation Stimulates Production of Novel Polyphosphoinositides in Intact Cells" *Cell*, vol. 57, No. 1 pp. 167–175, 7 Apr. 1989.

Auger et al., "Polyoma Virus Middle T Antigen–pp60$^{c-src}$ Complex Associates with Purified Phosphatidylinositol 3–Kinase in Vitro" *Journal of Biological Chemistry*, vol. 267, No. 8, pp. 5408–5415, 15 Mar. 1992.

Bayle–Lacoste et al., "Synthesis of 4–phosphono and of 4–(phosphonomethyl)–di–phenylalanine, two analogues of o–phosphotyrosine" *Tetrahedron*, vol. 46, No. 23, pp. 7793–7802, 1990.

Beitner–Johnson and LeRoith, "Insulin–like Growth Factor–I Stimulates Tyrosine Phosphorylation of Endogenous c–Crk" *Journal of Biological Chemistry*, vol. 270, No. 10, 10 Mar. 1995.

Bigge et al., "Exploration of Phenyl–Spaced 2–Amino–(5–9)–phosphonoalknaoiuc Acids as Competitive N–Methyl–D–aspartic Acid Antagonists" *J. Medicinal Chemistry*, vol. 32, No. 7, pp. 1580–1590, 1989.

Bouchard et al., "Phosphorylation and Identification of a Major Tyrosine Phosphorylation Site in Protein Tyrosine Phosphatase 1C" *Journal of Biological Chemistry*, vol. 269, No. 30, pp. 19585–19589, 29 Jul. 1994.

Burke, Jr. et al., "Phosphonate–Containing Inhibitors of Tyrosine–Specific protein Kinases" *Journal of Medicinal Chemistry*, vol. 34, No. 5, pp. 1577–1581, May 1991.

Burk, Jr. et al., "Preparation of 4–[Bis(tert–butoxy)phosphorylmethyl] –N–(fluoren–9–ymethoxycarbonyl)–DL–phenylalanine. A Hydrolytically Stable Analogue of O–Phosphotyrosine Potentially Suitable for Peptide Synthesis" *Synthesis*, No. 11, pp. 1019–1020, Nov. 1991.

Cance et al., "Rak, a Novel Nuclear Tyrosine Kinase Expressed in Epithelial Cells" *Cell Growth & Differentiation*, vol. 5, pp. 1347–1355, Dec. 1994.

Chanmugam et al., "Radicicol, a Protein Tyrosine Kinase Inhibitor, Suppresses the Expression of Mitogen–Inducible Cyclooxygenase in Macrophages Stimulated with Lipopolysaccharide and in Experimental Glomerulonephritis" *Journal of Biological Chemistry*, vol. 270, No. 10, pp. 5418–5426, 10 Mar. 1995.

Chen et al., "Structure of Malhamensilipin A, an Inhibitor of Protein Tyrosine Kinase, From the Cultured Chrystophyte *Poterioochromonas Malahamensis*" *Journal of Natural Products*, vol. 57, No. 4, pp. 524–527, Apr. 1994.

Cohen and Cohen, "Protein Phosphatases Come of Age" *Journal of Biological Chemistry*, vol. 264, No. 36, pp. 21435–21438, 25 Dec. 1989.

Coughlin et al., "Role of Phosphatidylinositol Kinase in PDGF Receptor Signal Transduction" *Science* vol. 243, pp. 1191–1194, 3 Mar. 1989.

Courtneidge, "Activation of the pp60$^{c-src}$ kinase by middle T antigen binding or by dephosphorylation" *EMBO Journal*, vol. 4, No. 6, pp. 1474–1477, Jun. 1985.

(List continued on next page.)

*Primary Examiner*—Robert J. Hill, Jr.
*Assistant Examiner*—Michael Borin
*Attorney, Agent, or Firm*—Louis Myers Lahive & Cockfield

[57] ABSTRACT

A peptide capable of inhibiting the interaction of an SH2 domain containing protein with a second protein.

16 Claims, 4 Drawing Sheets

OTHER PUBLICATIONS

Courtneidge and Heber, "An 81 kd Protein Complexed with Middle T Antigen and pp60$^{c-src}$: A Possible Phosphatidylinositol Kinase" *Cell*, vol. 50, pp. 1031–1037, 25 Sep. 1987.

Courtneidge and Smith, "Polyoma virus transforming protein associates with the product of the c-src cellular gene" *Nature*, vol. 303, pp. 435–439, 2 Jun. 1983.

Ellis et al., "Phosphorylation of GAP and GAP-associated proteins by transforming and mitogenic tyrosine kinases" *Nature*, vol. 343, No. 6256, pp. 377–381, 25 Jan. 1990.

Ernould et al., "Substrate phosphorylation capacities of the major tyrosine protein kinase from the human promyelocytic cell line, HL-60" *Int. J. Peptide Protein Res.*, 43, pp. 496–504, 1994.

Escobedo and Williams, "A PDGF receptor domain essential for mitogenes but not for many other responses to PDGF" *Nature*, vol. 335, No. 6185, pp. 85–87, 1 Sep. 1988.

Escobedo et al., "A Phosphatidylinositol-3 Kinase Binds to Platelet-Derived Growth Factor Receptors through a Specific Receptor Sequence Containing Phosphotyrosine" *Molecular and Cellular Biology*, vol. 11, No. 2, pp. 1125–1132, Feb. 1991.

Fantl et al., "Distinct Phosphotyrosines on a Growth Factor Receptor Bind to Specific Molecules That Mediate Different Signaling Pathways" *Cell*, vol. 269, No. 3, pp. 413–423, 1 May 1992.

Fish et al., "Inhibitory Effects of α-Interferon on Epidermal Growth Factor–mediated Receptor–dependent Events" *Cancer Research*, vol. 53, pp. 5148–5157, 1 Nov. 1993.

Fry et al., "A Specific Inhibitor of the Epidermal Gowth Factor Receptor Tyrosine Kinase" *Science*, vol. 265, pp. 1093–1095, 19 Aug. 1994.

Fu and Schmitz, "Inhibitors of Protein Tyrosine Kinas pp60$^{v-src}$: Sterol Sulfates From the Brittle Star *Ophiarachna Incrassata*" *Journal of Natural Products*, vol. 57, No. 11, pp. 1591–1594, Nov. 1994.

Guan et al., "Cloning and expression of a protein–tyrosine-phosphatase" *Proceedings of the National Academy of Sciences*, vol. 87, pp. 1501–1505, Feb. 1990.

Heidaran et al., "Deletion or Substitution within the α Platelet–Derived Growth Factor Receptor Kinase Insert Domain Effect on Functional Coupling with Intracellular Signaling Pathways" *Molecular and Cellular Biology*, vol. 11, No. 1, pp. 134–142, Jan. 1991.

Hu et al., "Interaction of Phosphatidylinositol 3–Kinase–Associated p85 with Epidermal Growth Factor and Platelet-–Derived Growth Factor Receptors" *Molecular and Cellular Biology*, vol. 12, No. 3, pp. 981–990, Mar. 1992.

Hunter, "Protein–Tyrosine Phosphatases: The Other Side of the coin" *Cell*, vol. 58, No. 6, pp. 1013–1016, 22 Sep. 1989.

Hunter, "Synthetic Peptide Substrates for a Tyrosine Protein Kinase" *Journal of Biological Chemistry*, vol. 257, No. 9, pp. 4843–4848, 10 May 1982.

Jayatilake et al., "Kinase Inhibitors From *Polygonum Cuspidatum*" *Journal of Natural Products*, vol.56, No. 10, pp. 1805–1810, Oct. 1993.

Kaplan et al., "Common Elements in Growth Factor Stimulation and Oncogenic Transformation: 85 kd Phosphoprotein and Phosphatidylinositol Kinase Activity" *Cell* vol. 50, No. 7, pp. 1021–1029, 25 Sep. 1987.

Kaplan et al., "PDGF β–Receptor Stimulates Tyrosine Phosphorylation of GAP and Association of GAP with a Signaling Complex" *Cell*, vol. 61, No. 1, pp. 125–133, 6 Apr. 1990.

Kashishian et al., "Phosphorylation sites in th PDGF receptor with different specificities for binding GAP and PI3 Kinase in vivo" *EMBO Journal*, vol. 11, No. 4, pp. 1373–1382, Apr. 1992.

Kazlauskas and Cooper "Autophosphorylation of the PDGF Receptor Kinase Insert Region Regulates Interactions with Cell Proteins" *Cell*, vol. 58, pp. 1121–1133, Sep. 1989.

Kazlauskas and Cooper, "Phosphorylation of the PDGF receptor β subunit creates a tight binding site for phosphatidylinositol 3 kinase" *EMBO Journal*, vol. 9, No. 10, pp. 3279–3286, Oct. 1990.

Kazlauskas et al., "Binding of GAP to Activated PDGF Receptors" *Science*, vol. 247, No. 4950, pp. 1578–1581, 30 Mar. 1990.

Kitas et al., "Alternative Strategies for the Fmoc Solid-–Phase Synthesis of $O^4$–Phospho–L–tyrosine–Containing Peptides" *Helvetica Chimica Acta*, vol. 74, pp. 1314–1328, Oct. 1991.

Koch et al., "SH2 and SH3 Domains: Elements That Control Interactions of Cytoplasmic Signaling Proteins" *Science*, vol. 252, pp. 668–674, 3 May 1991.

Kornbluth et al., "Association of the polyomavirus middle–T antigen with cyes protein" *Nature: Letters to Nature*, vol. 325, No. 7000, pp. 171–173, 8 Jan. 1987.

Kypta et al., "Association between the PDGF Receptor and Members of the src Family of tyrosine Kinases" *Cell*, vol. 62, No. 3, pp. 481–492, 10 Aug. 1990.

Kypta et al., "Identification and characterization of p59$^{fyn}$ (a src-like protein tyrosine kinase) in normal and polyoma virus transformed cells" *EMBO Journal*, vol. 7, No. 12, pp. 3837–3844, 1 Dec. 1988.

Lammers et al., "Differential Activities of Protein Tyrosine Phosphatases in Intact Cells" *Journal of Biological Chemistry*, vol. 268, No. 30, 25 Oct. 1993.

Lev et al., "Interkinase domain of kit contains the binding site for phosphatidylinositol 3' kinase" *PNAS*, vol. 89, No. 2, pp. 678–682, 15 Jan. 1992.

Margolis et al., "EGF Induces Tyrosine Phosphorylation of Phospholipase C–II; A Potential Mechanism for EGF Receptor Signaling" *Cell*, vol. 57, pp. 1101–1107, 30 Jun. 1989.

Marseigne and Roques, "Synthesis of New Amino Acids Mimicking Sulfated and Phosphorylated Tyrosine Residues" *Journal of Organic Chemistry*, vol. 53, No. 15, pp. 3621–3624, 22 Jul. 1988.

Mattar et al., "Inhibition of the epidermal growth factor receptor tyrosine kinase activity by leflunomide" *FEBS*, vol. 334, No. 2, pp. 161–164, Nov. 1993.

Mayer and Hanafusa, "Mutagenic Analysis of the v–crk Oncogene: Requirement for SH2 and SH3 Domains and Correlation between Increased Cellular Phosphotyrosine and Transformation" *Journal of Virology*, vol. 64, No. 8, pp. 3581–3589, Aug. 1990.

Meisenhelder et al., "Phospholipase C–γ Is a Substrate for the PDGF and EGF Receptor Protein–Tyrosine Kinases In Vivo and In Vitro" *Cell*, vol. 57, No. 7, pp. 1109–1122, 30 Jun. 1989.

Mohammadi et al., "A Tyrosine–Phosphorylated Carboxy-–Terminal Peptide of the Fibroblast Growth Factor Receptor (Flg) Is a Binding Site for the SH2 Domain of Phospholipase C–γ1" *Molecular and Cellular Biology*, vol. 11, No. 10, pp. 5068–5078, Oct. 1991.

Moran et al., "Src homology region 2 domain direct protein–protein interactions in signal transduction" *PNAS*, vol. 87, No. 21, pp. 8622–8626, Nov. 1990.

Morrison et al., "Direct Activation of the Serine/Threonine Kinase Activity of Raf–1 through Tyrosine Phosphorylation by the PDGF β–Receeoptor" *Cell*, vol. 58, pp. 649–657, 25 Aug. 1989.

Morrison et al., "Signal transduction from membrane to cytoplasm: Growth factors and membrane–bound oncogene products increase Raf–1 phosphorylation and associated protein kinase activity" *PNAS*, vol. 85, pp. 8855–8859, Dec. 1988.

Okabe et al., "BE–23372M, A Novel Protein Tyrosine Kinase Inhibitor" *Journal of Antibiotics*, vol. 47, No. 3, pp. 289–293, Mar. 1994.

Otsu et al., "Characterization of Two 85 kd Proteins That Associate with Receptor Tyrosine Kinases, Middle–T/pp60$^{c-src}$ Complexes and P13–Kinase" *Cell*, vol. 65, pp. 91–104, 5 Apr. 1991.

Patschinsky et al., "Analysis of the sequence of amino acids surrounding sites of tyrosine phosphorylation" *PNAS*, vol. 79, pp. 973–977, Feb. 1982.

Pawson and Bernstein, "Receptor tyrosine kinases genetic evidence for their role in Drosophila and mouse development" *Trends in Genetics*, vol. 6, No. 11, pp. 350–356, Nov. 1990.

Ramdas et al., "The Degree of Inhibition of Protein Tyrosine Kinase Activity by Tyrphostin 23 and 25 Is Related to Their Instability" *Cancer Research*, vol. 54, pp. 867–869, 15 Feb. 1994.

Reedijk et al., "Tyr721 regulates specific binding of the CSF–1 receptor kinase insert to PI 3'–kinase SH2 domains: a model for SH2–mediated receptor–target interactions" *EMBO Journal*, vol. 11, No. 4, pp. 1365–1372, Apr. 1992.

Serunian et al., "Production of Novel Polyphosphoinositides In Vivo Is Linked to Cell Transformation by Polymavirus Middle T Antigen" *Journal of Virology*, vol. 64, No. 10, pp. 4718–4725, Oct. 1990.

Shoelson et al., "Solid–Phase Synthesis of Nonhydrolyzable Phosphotyrosl Peptide Analogues with N$^{\alpha}$–Fmoc–(O, O–di–t–butyl)phosphono–p–methylphenylalanine" *Tetrahedron*, vol. 32, No. 43, pp. 6061–6064, 21 Oct. 1991.

Siemeister, G, et al., "Recombinant Human Insulin Receptor Substrate–1 Protein" *Journal of Biochemistry and Molecular Biology*, vol. 270, No. 9, pp. 4870–4874, 3 Mar. 1995.

Skolnik et al., "Cloning of P13 Kinase–Associated p85 Utilizing a Novel Method for Expression/Cloning of Target Proteins for Receptor Tyrosine Kinases" *Cell*, vol. 65, No. 1, pp. 83–90, 5 Apr. 1991.

Song, W. et al., "Synthesis and Characterization of N–Parinaryoyl Analogs of Ganglioside G$_{M3}$ and De–N–acetyl G$_{M3}$. Interactions with the EGF Receptor Kinase" *Biochemistry*, vol. 32, pp. 8602–8607, 1993.

Srinivas and Grunberger, "Inhibitors of the Insulin Receptor Tyrosine Kinase" *Pharmac. Ther.*, vol. 64, pp. 23–35, 1994.

Srinivas et al., "Baculoviral Expression of a Natural Inhibitor of the Human Insulin Receptor Tyrosine Kinase" *Biochemical and Biophysical Reseach Communications*, vol. 208, No. 2, pp. 879–885, 17 Mar. 1995.

Stadtmauer and Rosen, "Phosphorylation of Exogenous Substrates by the Insulin Receptor–associated Protein Kinase" *Journal of Biological Chemistry*, vol. 258, No. 11, pp. 6682–6685, Jun. 10, 1983.

Stadtmauer and Rosen, "Phosphorylation of Synthetic Inslin Receptor Peptides by the Insulin Receptor Kinase and Evidence That the Preferred Sequence Containing Tyr–1150 is Phosphorylated in Vivo" *Journal of Biological Chemistry*, vol. 261, No. 21, pp. 10000–10005, 25 Jul. 1986.

Stahl et al., "Sequence similarity of phospholipase C with the non–catalytic region of src" *Nature*, vol. 332, No. 6161, pp. 269–272, 17 Mar. 1988.

Suh et al., "Inositol phospholipid–specific phospholipse C: Complete cDNA and protein sequences and sequence homology to tyrosine kinase–related oncogene products" *PNAS*, vol. 85, No. 15, pp. 5419–5423, Aug. 1988.

Sun et al., "Structure of the Insulin receptor substrate IRS–1 defines a unique signal transduction protein" *Nature*, vol. 352, pp. 73–77, No. 6330, 4 Jul. 1991.

Talmage et al., "Phosphorylation of Middle T by pp60$^{c-src}$: A Switch for Binding of Phosphatidylinositol 3–Kinase and Optimal Tumorigenesis" *Cell*, vol. 59, pp. 55–65, 6 Oct. 1989.

Taniguchi et al., "Inhibition of RET Tyrosine Kinase Activity by Herbimycin A" *Biochemical and Biophysical Research Communications*, vol. 195, No. 1, pp. 208–214, 31 Aug. 1993.

Taylor et al., "The unique insert of cellular and viral fms protein tyrosine kinase domains is dispensable for enzymatic and transforming activities" *EMBO Journal*, vol. 8, No. 7, pp. 2029–2037, Jul. 1989.

Tobe et al., "Identification of a 190–kDa Protein as a Novel Substrate for the Insulin Receptor Kinase Functionally Similar to Insulin Receptor Substrate–1" *J. Biol. Chem.*, vol. 270, No. 11, 17 Mar. 1995.

Tonks, "Introduction: Protein tyrosine phosphatases" *Seminars in Cell Biology*, vol. 4, pp. 373–377, 1993.

Trahey et al., "Molecular Cloning of Two Types of GAP Complementary DNA from Human Placenta" *Science*, vol. 242, pp. 1697–1700, 23 Dec. 1988.

Ullrich et al., "Signal Transduction by Receptors with Tyrosine Kinase Activity" *Cell*, vol. 61, pp. 203–212, Apr. 1990.

Ulug et al., "Phosphatidylinositol Metabolism in Cells Transformed by Polymavirus Moddle T Antigen" *Journal of Virology*, vol. 64, No. 8, pp. 3895–3904, Aug. 1990.

Varticovski et al., "The colony stimulating factor–1 receptor associated with and activates phosphatidylinositol–3 kinase" *Nature*, vol. 342, pp. 699–637, 7 Dec. 1989.

Viñals et al., "Inhibitory effect of fluoride on insulin receptor autophosphorylation and tyrosine kinase activity" *Biochem. J.*, vol. 291, Part 2, pp. 615–622, 1993.

Vogel et al., "cloning of bovine GAP and its interaction with oncogenic ras p21" *Nature*, vol. 335, No. 6135, pp. 90–93, 1 Sep. 1988.

White et al., "A Cascade of Tyrosine Autophosphorylation in the β–Subunit Activates the phosphotransferase of the Insulin Receptor" *Journal of Biological Chemistry*, vol. 263, No. 6, pp. 2969–2980, 25 Feb. 1988.

Whitman et al., "Association of phosphatidylinositol kinase activity with polyoma middle–T competent for transformation" *Nature* vol. 315, pp. 239–242, 16–22 May 1985.

Wong et al., "In Vitro Phosphorylation of Angiotensin Analogs by Tyrosyl Protein Kinase" *Journal of Biological Chemistry*, vol. 258, No. 2, pp. 1022–1025, 25 Jan. 1983.

H—Arg—Asp—Ile—Pmp—Glu—Thr—Asp—Tyr—Tyr—Arg—Lys—OH
SEQUENCE ID Nº:44

H—Arg—Glu—Asn—Glu—Pmp—Met—Pro—Met—Ala—Pro—Glu—Ile—His—OH
SEQUENCE ID Nº:21

INHIBITION OF SIGNAL TRANSDUCTION MOLECULES

RELATED APPLICATIONS

This application is a continuation-in-part of Ser. No. 08/134,558, filed Oct. 8, 1993, now abandoned which is a continuation-in-part of Ser. No. 07/959,949, filed Oct. 9, 1992, now abandoned hereby incorporated by reference, which is a continuation-in-part of Ser. No. 07/722,359, filed Jun. 19, 1991, now abandoned. All of the above-recited applications are hereby incorporated by reference.

BACKGROUND OF THE INVENTION

The invention relates to the inhibition of signal transduction molecules.

Protein tyrosine kinases (PTKs), including, e.g., growth factor receptors, proto-oncogene and oncogene products, and the insulin receptor, catalyze tyrosine phosphorylations within their own sequences as well as on other cellular proteins. These phosphorylations are thought to be essential for transmission of ligand binding signals into cells and for intermolecular interactions within cells. The regulation of tyrosine phosphorylation levels appears to be important for both cellular growth and metabolic control. Protein-tyrosine phosphatases (PTPases), which dephosphorylate PTKs and their substrates, are crucial for attenuating levels of tyrosine phosphorylation. Families of PTPases are now being identified e.g., by cloning and expression of DNA sequences homologous to the catalytic domains of placental PTPase 1B and LCA/CD45 from leukocytes, which are among the best characterized PTPases.

SUMMARY OF THE INVENTION

In general, the invention features peptides, or mimics of these peptides, capable of inhibiting an interaction, preferably a site specific interaction, of an SH2-domain-containing protein, e.g., a signal transduction protein, e.g., a cytoplasmic or a transmembrane signal transduction protein, a receptor protein, e.g., the insulin receptor or the PDGF receptor, or a protein which is active in the regulation of cell proliferation, e.g., an oncogene product, with a second protein, e.g., a protein containing the sequence Tyr-$R^1$-$R^2$-Met (SEQ ID NO: 1) (wherein $R^1$ is Met, Val, Ile, or Glu; and $R^2$ is any amino acid, but is preferably Pro, Met, Asp, Thr, Asn, Glu, or Tyr) e.g., Tyr-Met-$R^2$-Met (SEQ ID NO: 8), or the sequence Tyr-$R^1R^2$-$R^3$ (SEQ ID NO: 2) (wherein $R^1$ is Glu, Asp, Thr, Tyr, His, or Gln; $R^2$ is Glu, Asn, Tyr, or Asp; and $R^3$ is Ile, Met, Leu, or Val) e.g., Tyr-Glu-Glu-Ile, (SEQ ID NO: 3) e.g., a protein capable of altering the state of phosphorylation of a tyrosine residue, e.g., a tyrosine kinase.

Peptides of the invention include the sequence $R^1$-$R^2$-$R^3$-$R^4$ (SEQ ID NO: 4) (wherein $R_1$ is tyrosine, phosphotyrosine, or more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, mono- or difluorophosphonomethylphenlalanine (FPmp or $F_2$Pmp, respectively); $R^2$ is Asp, Thr, Tyr, His, Gln, Met, Val, Ile, Ala, Leu, Ser, Phe, Glu or omitted; $R^3$ is any amino acid, but is preferably Ile, Pro, Met, Asp, Thr, Asn, Glu, Ala, Val, Cys, Arg, Ser, Gln, Lys, Tyr, or omitted; and $R^4$ is Ile, Met, Leu, Pro, Gln, Thr, Ala, Gly, Asp, Tyr, Val, or omitted. In preferred embodiments the peptide includes the sequence $R^1$-$R^2$-$R^3$-Met (SEQ ID NO: 5) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Met, Val, Ile, or Glu; and $R^3$ is any amino acid, but is preferably Pro, Met, Asp, Thr, Asn, Glu, or Tyr) e.g., Pmp-Met-$R^3$-Met (SEQ ID NO: 6), FPmp-Met-$R^3$-Met (SEQ ID NO: 6) or $F_2$Pmp-Met-$R^3$-Met (SEQ ID NO: 6). In other preferred embodiments the peptide includes the sequence $R^1$-$R^2$-$R^3$-$R^4$ (SEQ ID NO: 4) (wherein $R_1$ is phosphotyrosine or, more preferably, an analog of phosphotyrosine having a hydrolysis resistant phosphorous moiety, e.g. phosphonomethylphenylalanine, or a hydrolysis resistant phosphorous moiety which is more electronegative than the phosphate group of phosphotyrosine, for example, FPmp or $F_2$Pmp; $R^2$ is Glu, Asp, Thr, Tyr, His, or Gln; $R^3$ is Glu, Asn, Tyr, or Asp; and $R^4$ is Ile, Met, Leu, or Val) e.g., Pmp-Glu-Glu-Ile (SEQ ID NO: 7), FPmp-Glu-Glu-Ile (SEQ ID NO: 7) or $F_2$Pmp-Glu-Glu-Ile (SEQ ID NO: 7).

In preferred embodiments the peptide includes the sequence $R^1$-$R^2$-$R^3$-$R^4$ (SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile, Thr, Leu, Tyr, or Val; $R^3$ is Tyr, Ala, Val, Cys, Glu, Met, Asn, or Asp; $R^4$ is Val, Ile, Met, or Leu.

In preferred embodiments the peptide includes the sequence $R^1$-$R^2$-$R^3$-$R^4$ (SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile, Thr, Leu, Met, Ala, His, Ser, Asp, or Val; $R^3$ is Tyr, Ala, Val, Cys, Ile, Met, Asn, Arg, or Asp; $R^4$ is Val, Ile, Met, Gln, Thr, Ala, or Pro.

In preferred embodiments the peptide includes the sequence $R^1$-$R^2$-$R^3$-$R^4$ (SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile, Thr, Leu, Met, Ser, or Val; $R^3$ is Tyr, Ala, Val, Cys, Ile, Met, Asn, Arg, Glu, Thr, Pro, or Asp; $R^4$ is Val, Ile, Met, Gln, Thr, Ala, Leu, or Pro.

In preferred embodiments the peptide includes the sequence $R^1$-$R^2$-$R^3$-$R^4$ (SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ser, Ala, Leu, Phe, or omitted; $R^3$ is Val, Ser or omitted; $R^4$ is Met, Ala, or omitted.

In preferred embodiments the peptide includes the sequence $R^1$-$R^2$-$R^3$-$R^4$ (SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile; $R^3$ is Ile, or Asp; $R^4$ is Pro.

In preferred embodiments the peptide includes the sequence $R^1$-$R^2$-$R^3$-$R^4$(SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile, Leu, Val, Ser, Met, Thr, or Ala; $R^3$ is Ile, Val, Asn, Arg, Tyr, Pro, Ala, Cys, Glu, Met, Thr, Ser, or Asp; $R^4$ is Pro, Ile, Gln, Thr, Val, Ala, Met, or Leu.

In preferred embodiments the peptide includes the sequence $R^1$-$R^2$-$R^3$-$R^4$(SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile, or Asp; $R^3$ is Ile, Asp or omitted; $R^4$ is Pro or omitted.

In preferred embodiments the peptide includes the sequence $R^1$-$R^2$-$R^3$-$R^4$(SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Glu; $R^3$ is Glu; $R^4$ is Ile, Leu, Met, Val, or omitted.

In preferred embodiments the peptide includes the sequence $R^1$-$R^2$-$R^3$-$R^4$(SEQ ID NO: 4) (wherein $R_1$ is phosphotyrosine or, more preferably, an analog of phosphotyrosine having a hydrolysis resistant phosphorous moiety, e.g. phosphonomethylphenylaianine (Pmp), or a hydrolysis resistant phosphorous moiety which is more electronegative than the phosphate group of phosphotyrosine, for example, FPmp or $F_2$Pmp; $R^2$ is Ile, Leu, Val, Ser, Met, Thr, Asp, His, Gln, Glu, or Ala; $R^3$ is Ile, Val, Asn, Tyr, Pro, Ala, Cys, Glu, Met, Thr, Ser, Gln, or Asp; $R^4$ is Pro, Ile, Gln, Thr, Val, Ala, Met, Gly, Asp, or Leu.

In preferred embodiments the peptide includes the sequence $R^1$-$R^2$-$R^3$-$R^4$(SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile, Leu, Val, Ser, Met, Thr, Asp, Gln, Glu, or Ala; $R^3$ is Ile, Val, Asn, Tyr, Pro, Ala, Cys, Glu, Met, Thr, Ser, Gln, or Asp; $R^4$ is Pro, Ile, Gln, Tyr, Val, Ala, Met, Gly, Asp, or Leu.

In preferred embodiments the peptide includes the sequence $R^1$-$R^2$-$R^3$-$R^4$(SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile, Leu, Val, Ser, Met, Thr, Asp, Gln, Glu, Tyr, or His; $R^3$ is Asn, Gln, or Lys; $R^4$ is Ile, Gln, Tyr, Val, Ala, Met, Thr, Asp or omitted.

In preferred embodiments the peptide includes the sequence $R^1$-$R^2$-$R^3$-$R^4$(SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile, or Val; $R^3$ is Asp or Asn; $R^4$ is Leu, or Ile.

In preferred embodiments the peptide includes the sequence $R^1$-$R^2$-$R^3$-$R^4$(SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile, or Ala; $R^3$ is Ile, Ala, or omitted; $R^4$ is Pro, Ala, or omitted.

In preferred embodiments the peptide includes the sequence $R^1$-$R^2$-$R^3$-$R^4$(SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Ile, Leu, Val, His, Met, Thr, Gln, Glu, or Ala; $R^3$ is Ile, Val, Asn, Tyr, Pro, Ala, Glu, Ser, or Asp; $R^4$ is Pro, Ile, Gln, Val, Met, Ieu or omitted.

In preferred embodiments the peptide includes the sequence $R^1$-$R^2$-$R^3$-$R^4$(SEQ ID NO: 4) (wherein $R_1$ is phosphotyrosine or, more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp; $R^2$ is Met, or Ala; $R^3$ is Pro, or Ala; $R^4$ is Met. In more preferred embodiments the peptide is at least 3, 5, 10, or 15, amino acid residues in length. In more preferred embodiments the peptide is less than 10, 15, 20, 30 or 40 amino acid residues in length. In preferred embodiments the peptide has an $ED_{50}$ or $IC_{50}$ of less than 500, 100, 10, 1, or 0.1 µM for inhibiting binding of the phosphoprotein to an SH2 domain containing protein or fragment thereof.

The peptide can be one which is at least 50, 60, 70, 80, 90, or 100% homologous with a fragment of a phosphoprotein which interacts with the SH 2 domain-containing protein and which contains a tyrosine residue of the phosphoprotein, e.g., a phosphotyrosine which is at the site which binds the SH 2 domain. In more preferred embodiments the peptide is at least 3, 5, 10, or 15, amino acid residues in length. In more preferred embodiments the peptide is less than 10, 15, 20, 30 or 40 amino acid residues in length. In preferred embodiments the peptide has an $ED_{50}$ or $IC_{50}$ of less than 500, 100, 10, 1, or 0.1 µM for inhibiting binding of the phosphoprotein to an SH2 domain containing protein or fragment thereof. In preferred embodiments the phosphotyrosine can be replaced with an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or $F_2$Pmp.

In preferred embodiments the peptide is at least 60, 70, 80, 90, or 100% homologous with a fragment of the PDGF receptor which contains a tyrosine residue, e.g., Tyr579, Tyr581, Tyr740, Tyr751, Tyr771, Tyr1009, or Tyr1021.

In preferred embodiments the peptide is at least 60, 70, 80, 90, or 100% homologous with a fragment of the EGF receptor which contains a tyrosine residue, e.g., Tyr920, Tyr954, Tyr992, Tyr1068, Tyr1086, Tyr1114, Tyr1148, or Tyr1173.

In preferred embodiments the peptide is at least 60, 70, 80, 90, or 100% homologous with a fragment of IRS-1 which contains a tyrosine residue, e.g., Tyr147, Tyr460, Tyr546, Tyr608, Tyr628, Tyr658, Tyr727, Tyr895, Tyr939, Tyr987, Tyr1010, Tyr1172, or Tyr1222.

In preferred embodiments the peptide is at least 60, 70, 80, 90, or 100% homologous with a fragment of mmT which contains a tyrosine residue, e.g., Tyr250.

In preferred embodiments the peptide is at least 60, 70, 80, 90, or 100% homologous with a fragment of IR which contains a tyrosine residue, e.g., Tyr960.

In preferred embodiments the peptide is at least 60, 70, 80, 90, or 100% homologous with a fragment of TrkA which contains a tyrosine residue, e.g., Tyr490.

In preferred embodiments the peptide is at least 60, 70, 80, 90, or 100% homologous with a fragment of TrkB which contains a tyrosine residue, e.g., Tyr816.

In preferred embodiments the peptide is at least 60, 70, 80, 90, or 100% homologous with a fragment of Cb1 which contains a tyrosine residue, e.g., Tyr774.

In preferred embodiments the peptide is at least 60, 70, 80, 90, or 100% homologous with a fragment of PGFR which contains a tyrosine residue, e.g., Tyr766.

In preferred embodiments the peptide is at least 60, 70, 80, 90, or 100% homologous with a fragment of Src which contains a tyrosine residue, e.g., Tyr527.

In preferred embodiments the peptide is at least 60, 70, 80, 90, or 100% homologous with a fragment of Lck which contains a tyrosine residue, e.g., Tyr505

In preferred embodiments the peptide is at least 60, 70, 80, 90, or 100% homologous with a fragment of hmT which contains a tyrosine residue, e.g., Tyr324.

In preferred embodiments the peptide is at least 60, 70, 80, 90, or 100% homologous with a fragment of Fyn which contains a tyrosine residue, e.g., Tyr530.

In preferred embodiments the peptide is at least 60, 70, 80, 90, or 100% homologous with a fragment of Syp which contains a tyrosine residue, e.g., Tyr304, Tyr542, or Tyr580.

In preferred embodiments the peptide is at least 60, 70, 80, 90, or 100% homologous with a fragment of BCR which contains a tyrosine residue, e.g., Tyr177.

In preferred embodiments the peptide is at least 60, 70, 80, 90, or 100% homologous with a fragment of CD 28 which contains a tyrosine residue, e.g., Tyr191.

In preferred embodiments the peptide is at least 60, 70, 80, 90, or 100% homologous with a fragment of Shc which contains a tyrosine residue, e.g., Tyr239, Tyr240, or Tyr317.

In preferred embodiments the peptide is at least 60, 70, 80, 90, or 100% homologous with a fragment of PLCγ which contains a tyrosine residue, e.g., Tyr1021.

In preferred embodiments the peptide is at least 60, 70, 80, 90, or 100% homologous with a fragment of GAP which contains a tyrosine residue, e.g., Tyr1021.

Peptides of the invention also include peptides having at least 50, 60, 70, 80, 90, or 100% homology with the following sequences:

Pmp-Glu-Glu-Ile (SEQ ID NO: 7), FPmp-Glu-Glu-Ile (SEQ ID NO: 7); F$_2$Pmp-Glu-Glu-Ile (SEQ ID NO: 7); E-D-L-S-pY-D-T-G-P-G-P-A (SEQ ID NO:49); L-S-N-pY-I-C-M-G-G-K-G (SEQ ID NO:50); I-E-E-pY-TE-M-M-P-A-A (SEQ ID NO:51); D-D-G-pY-M-P-M-S-P-G-V (SEQ ID NO:52); G-N-G-D-pY-M-P-M-S-P-K-S (SEQ ID NO:53); P-N-G-pY-M-M-M-S-P-S-G (SEQ ID NO:54); T-G-D-pY-M-N-M-S-P-V-G (SEQ ID NO:55); S-P-G-E-pY-V-N-I-E-F-G-S (SEQ ID NO:56); S-E-E-pY-M-N-M-D-L-P-G (SEQ ID NO:57); R-D-G-pY-M-T-M-Q-I-G (SEQ ID NO:58); P-V-S-pY-A-D-M-R-I-G-I (SEQ ID NO:59); L-N-pY-I-D-L-D-L-V (SEQ ID NO:60); L-S-T-pY-A-S-I-N-F-Q-K (SEQ ID NO:61); Ser-Leu-Asn-pTyr-Ile-Asp-Leu-Asp-Leu-Val-Lys-NH$_2$ (SEQ ID NO:62); Leu-Asn-pIyr-Ile-Asp-Leu-Asp-Leu-NH$_2$ (SEQ ID NO:63); Leu-Asn-pTyr-Ile-Asp-Leu-Asp-NH$_2$ (SEQ ID NO:64); Leu-Asn-pTyr-Ile-Asp-Leu-NH$_2$ (SEQ ID NO:65); Ser-Pro-Gly-Glu-pTyr-Val-Asn-Ile-Glu-Phe-Gly-Ser (SEQ ID NO:66); Ser-Pro-Gly-Glu-pTyr-Val-Asn-Ile-Glu-Asp-Gly-Ser (SEQ ID NO:67); I-D-V-pY-M-I-M-V-K (SEQ ID NO:68); P-Q-R-pY-L-V-I-Q-G-D (SEQ ID NO:69); D-A-D-E-pY-L-I-P-Q-Q-G-F-F (SEQ ID NO:70); V-P-E-pY-I-N-Q-S-V-P-K (SEQ ID NO:71); N-P-V-pY-H-N-Q-P-L-N (SEQ ID NO:72); N-P-E-pY-L-N-T-V-Q-P-T (SEQ ID NO:73); N-P-D-pY-Q-Q-D-F-F-P-K (SEQ ID NO:74); N-A-E-pY-L-R-V-A-P-Q-S (SEQ ID NO:75); G-H-E-pY-I-Y-V-D-P-M (SEQ ID NO:76); G-H-E-Y-I-pY-V-D-P-M (SEQ ID NO :77); G-H-E-pY-I-pY-V-D-P-M (SEQ ID NO:78);A-E-L-pY-S-N-A-L-P-V (SEQ ID NO :79); D-G-G-pY-M-D-M-S-K-D-E (SEQ ID NO:80); S-V-D-pY-V-P-M-L-D-M-K (SEQ ID NO:81); S-S-N-pY-M-A-P-Y-D-N-Y (SEQ ID NO:82); M-A-P-pY-D-N-Y-V-P-S (SEQ ID NO:83); S-V-L-pY-T-A-V-Q-P-N-E (SEQ ID NO:84); D-N-D-pY-I-I-P-L-P-D-P-K (SEQ ID NO:85); E-D-D-G-pY-D-V-P-K-P-P-V (SEQ ID NO:86); Ac-D-pY-D-A-P-A-NH$_2$ (SEQ ID NO:87); P-P-V-pY-L-D-V-L-G (SEQ ID NO:88); S-P-V-pY-L-D-I-L-G (SEQ ID NO:89); E-P-Q-pY-Q-P-G-E-N-L (SEQ ID NO:90); E-P-Q-Y-Q-P-G-E-N-L (SEQ ID NO:91); T-E-G-Q-pY-Q-P-Q-P-A (SEQ ID NO:92); E-G-Q-pY-Q-P-Q-P (SEQ ID NO:93); E-P-Q-pY-E-E-I-P-I-Y-L (SEQ ID NO:94); Glu-Pro-Gln-pTyr-Glu-Glu-Ile-Pro-Ile-Tyr-Leu (SEQ ID NO:95); Ac-Gln-pTyr-Glu-Glu-Ile-Pro-NH$_2$ (SEQ ID NO:96); Ac-pTyr-Glu-Glu-Ile-Pro-NH$_2$ (SEQ ID NO:97); Ac-pTyr-Glu-Glu-Ile-NH$_2$ (SEQ ID NO:98); Ac-pTyr-Glu-Glu-NH$_2$ (SEQ ID NO:99); Glu-Pro-Gln-pTyr-Glu-Glu-Ile-Pro-Ile-Tyr-Leu (SEQ ID NO:100); Glu-Pro-Gln-pTyr-Glu-Glu-Leu-Pro-Ile-Tyr-Leu (SEQ ID NO:101); Glu-Pro-Gln-pTyr-Glu-Glu-Met-Pro-Ile-Tyr-Leu (SEQ ID NO:102); Glu-Pro-Gln-pTyr-Glu-Glu-Val-Pro-Ile-Tyr-Leu (SEQ ID NO:103); Ac-pTyr-Glu-Glu-Ile-Pro-NH$_2$ (SEQ ID NO:104); Ac-pTyr-Glu-Glu-Ile-Ala-NH$_2$ (SEQ ID NO:105); E-P-Q-pY-Q-P-G-E-N-L (SEQ ID NO:106); E-P-Q-Y-Q-P-G-E-N-L (SEQ ID NO:107); V-S-D-pY-I-N-A-N-I-I (SEQ ID NO:108); G-H-E-pY-T-N-I-K-Y-S-L (SEQ ID NO:109); A-R-V-pY-E-N-V-G-L-M-Q (SEQ ID NO:110); K-P-F-pY-V-N-V-E-F (SEQ ID NO:111); H-S-D-pY-M-N-M-T-P-R (SEQ ID NO:112); D-N-D-pY-I-I-P-L-P-D-P-K (SEQ ID NO:113); Ac-N-D-pY-I-I-P-L-P-D-NH$_2$ (SEQ ID NO:114); Ac-D-pY-I-I-P-L-P-D-NH$_2$ (SEQ ID NO:115); Ac-D-pY-I-I-P-L-P-NH$_2$ (SEQ ID NO:116); Ac-D-pY-I-I-P-L-NH$_2$ (SEQ ID NO:117); Ac-A-pY-I-I-P-L-NH$_2$ (SEQ ID NO:118); Ac-D-Pmp-I-I-P-L-NH$_2$ (SEQ ID NO:119); Ac-D-pY-I-I-P-NH$_2$ (SEQ ID NO:120); Ac-D-pY-I-I-NH$_2$ (SEQ ID NO:121); Ac-D-pY-I-NH$_2$ (SEQ ID NO:122); Ac-pY-I-I-P-NH$_2$ (SEQ ID NO:123); Ac-pY-I-I-NH$_2$ (SEQ ID NO:124); Ac-D-pY-I-I-P-I-P-R-NH$_2$ (SEQ ID NO:125); Ac-D-pY-I-I-P-L-D-D-NH$_2$ (SEQ ID NO:126); Ac-D-pY-I-I-P-D-P-D-NH$_2$ (SEQ ID NO:127); Ac-D-pY-I-I-D-L-P-D-NH$_2$ (SEQ ID NO:128); Ac-D-pY-I-D-P-L-P-D-NH$_2$ (SEQ ID NO:129); Ac-D-pY-D-I-P-L-P-D-NH$_2$ (SEQ ID NO:130); LLSNPT-pYSVMRSK (SEQ ID NO:131);LSNPTpYSVMRSK (SEQ ID NO:132); LLSNPTpYSV (SEQ ID NO:133); LLSNPT-pYS (SEQ ID NO:134); LLSNPTpY-NH$_2$ (SEQ ID NO:135); LSNPTpYSV (SEQ ID NO:136); LSNPTpYAV (SEQ ID NO:137); LSNATpYSV (SEQ ID NO:138);

LANPTpYSV (SEQ ID NO:139); ASNPTpYSV (SEQ ID NO:140); LYASSNPEpYLSASDV (SEQ ID NO:141); YASSNPEpYLSASDV (SEQ ID NO:142); LYASSNPA-pYLSASDV (SEQ ID NO:143); LYASSNAEpYLSASDV (SEQ ID NO:144); LYASSAPEpYLSASDV (SEQ ID NO:145); LYASANPEpYLSASDV (SEQ ID NO:146); LYAASNPEpYLSASDV (SEQ ID NO:147); LYVSSNPEp-YLSASDV (SEQ ID NO:148); LAASSNPEpYLSASDV (SEQ ID NO:149); AYASSNPEpYLSASDV (SEQ ID NO:150); IENPQpYFS (SEQ ID NO:151); E-P-Q-pY-E-E-I-P-I-Y-L (SEQ ID NO:152); E-P-Q-pY-E-E-L-P-I-Y-L (SEQ ID NO:153); E-P-Q-pY-E-E-M-P-I-Y-L (SEQ ID NO:154); E-P-Q-pY-E-E-V-P-I-Y-L (SEQ ID NO:155); E-P-Q-pY-E-E-I-N-I-Y-L (SEQ ID NO:156); Ac-Q-pY-E-E-I-P-NH$_2$ (SEQ ID NO:157); Ac-Q-(D/L)F$_2$Pmp-E-E-I-P-NH$_2$ (SEQ ID NO:158); Ac-Q-(L)F$_2$Pmp-E-E-I-P-NH$_2$ (SEQ ID NO:159); Ac-pY-E-E-I-P-NH$_2$ (SEQ ID NO:160); Ac-pY-E-E-I-A-NH$_2$ (SEQ ID NO:161); Ac-Q-pY-E-E-I-NH$_2$ (SEQ ID NO:162); Ac-pY-E-E-I-NH$_2$ (SEQ ID NO:163); K-E-P-Q-pY-E-E-I-P-I-Y-L (SEQ ID NO:164); K-H-Q-pY-E-E-I-P-I-Y-L (SEQ ID NO:165); E-P-Q-sY-E-E-I-P-I-Y-L (SEQ ID NO:166); D-H-Q-pY-Y-N-D-M-P-G-K (SEQ ID NO:167); D-H-Q-Y-pY-N-D-M-P-G-K (SEQ ID NO:168); ELFDDPSpYVNVQNLDK (SEQ ID NO:169); P-S-pY-V-Q-V-Q-N-L (SEQ ID NO:170); P-S-pY-V-N-V-Q-N-L (SEQ ID NO:171); P-S-pY-V-N-V-Q-N (SEQ ID NO:172); Ac-pY-V-N-V-Q-NH$_2$ (SEQ ID NO:173); Ac-S-pY-V-N-V-NH$_2$ (SEQ ID NO:174); S-pY-V-N-V-NH$_2$ (SEQ ID NO:175); Ac-pY-V-N-V-NH$_2$ (SEQ ID NO:176); Ac-S-pY-V-N-NH$_2$ (SEQ ID NO:177); S-pY-V-N-NH$_2$ (SEQ ID NO:178); Ac-pY-V-N-NH$_2$ (SEQ ID NO:179); L-N-pY-I-D-L-D-L-V-NH$_2$ (SEQ ID NO:180); L-N-pY-I-D-L-D-L-NH$_2$ (SEQ ID NO:181); L-N-pY-I-D-LD-NH$_2$ (SEQ ID NO:182); L-N-pY-I-D-L-NH$_2$ (SEQ ID NO:183); L-N-pY-I-D-NH$_2$ (SEQ ID NO:184); Ac-N-pY-I-D-L-D-L-NH$_2$ (SEQ ID NO:185); N-pY-I-D-L-D-L-NH$_2$ (SEQ ID NO:186); Ac-pY-I-D-L-D-L-NH$_2$ (SEQ ID NO:187); Ac-Asp-pTyr-Ile-Ile-Pro-Leu-Pro-Asp-NH$_2$ (SEQ ID NO:188); Ac-Asp-pTyr-Ile-Ile-Pro-Leu-Pro-Arg-NH$_2$ (SEQ ID NO:189); Ac-Asp-pTyr-Ile-Ile-Pro-Leu-Asp-Asp-NH$_2$ (SEQ ID NO:190); Ac-Asp-pTyr-Ile-Ile-Pro-Asp-Pro-Asp-NH$_2$ (SEQ ID NO:191); Ac-Asp-pTyr-Ile-Ile-Asp-Leu-Pro-Asp-NH$_2$ (SEQ ID NO:192); Ac-Asp-pTyr-Ile-Asp-Pro-Leu-Pro-Asp-NH$_2$ (SEQ ID NO:193); Ac-Asp-pTyr-Asp-Ile-Pro-Leu-Pro-Asp-NH$_2$ (SEQ ID NO:194); Ac-Ala-pTyr-Asp-Ile-Pro-Leu-Pro-Asp-NH$_2$ (SEQ ID NO:195); Asn-Gly-Asp-pTyr-Met-Pro-Met-Ser-Pro-Lys-Ser-OH (SEQ ID NO:196); Gly-Asp-pTyr-Met-Pro-Met-Ser-Pro-Lys-Ser-OH (SEQ ID NO:197); Ac-Asp-pTyr-Met-Pro-Met-Ser-ProLys-Ser-OH (SEQ ID NO:198); Asp-pTyr-Met-Pro-Met-Ser-Pro-Lys-Ser-OH (SEQ ID NO:199); Ac-pTyr-Met-Pro-Met-Ser-Pro-Lys-Ser-OH (SEQ ID NO:200); pTyr-Met-Pro-Met-Ser-Pro-Lys-Ser-OH (SEQ ID NO:201); Ac-pTyr-Met-Pro-Met-Ser-Pro-NH$_2$ (SEQ ID NO:202); Ac-pTyrMet-Pro-Met-Ser-NH$_2$ (SEQ ID NO:203); Ac-pTyr-Met-Pro-Met-NH$_2$ (SEQ ID NO:204); Ac-pTyr-Met-Pro-Met-Ser-Pro-Lys-Ser-OH (SEQ ID NO:205); Ac-pTyr-Met-Pro-Met-Ser-Pro-Ala-Ser-OH (SEQ ID NO:206); Ac-pTyr-Met-Pro-Met-Ser-Ala-Lys-Ser-OH (SEQ ID NO:207); Ac-pTyr-Met-Pro-Met-Ala-Pro-Lys-Ser-OH (SEQ ID NO:208); Ac-pTyr-Met-Ala-Met-Ser-Pro-Lys-Ser-OH (SEQ ID NO:209); Ac-pTyr-Ala-Pro-Met-Ser-Pro-Lys-Ser-OH (SEQ ID NO:210); S-L-N-pY-I-D-L-D-L-V-K (SEQ ID NO:211).

In preferred embodiments the peptide has an ED$_{50}$ of less than 500, 100, 10, or 1 μM for inhibiting binding of the phosphoprotein to an SH2 domain containing protein or fragment thereof. In preferred embodiments the phosphotyrosine can be replaced with an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, FPmp or F$_2$Pmp. Fragments of these peptides as short as three residues in length can also be used in the invention.

In another aspect, the invention features a method of inhibiting an interaction, preferably a site specific interaction, between a first molecule which includes an SH2 domain, e.g., a signal transduction protein, e.g., a cytoplasmic or a transmembrane signal transduction protein, a receptor protein, e.g., the insulin receptor or the PDGF receptor, or a protein which is active in the regulation of cell proliferation, e.g., an oncogene product, and a second molecule, e.g., a protein containing the sequence Tyr-R$^1$-R$^2$-Met (SEQ ID NO: 1) (wherein R$_1$ is Met, Val, Ile, or Glu; and R$^2$ is any amino acid, but is preferably Pro, Met, Asp, Thr, Asn, Glu, or Tyr) e.g., Tyr-Met-R$^2$-Met (SEQ ID NO: 8), or the sequence Tyr-R$^1$-R$^2$-R$^3$ (SEQ ID NO: 2) (wherein R$^1$ is Glu, Asp, Thr, Tyr, His, or Gln; R$^2$ is Glu, Asn, Tyr, or Asp; and R$^3$ is Ile, Met, Leu, or Val) e.g., Tyr-Glu-Glu-Ile (SEQ ID NO: 3), e.g., a protein capable of altering the state of phosphorylation of a tyrosine residue, e.g., a tyrosine kinase. The method includes contacting the first molecule with an inhibitor molecule which includes a peptide (or mimic if a peptide) of the invention.

Preferred embodiments include those in which: the first molecule is a molecule which transmits a signal, e.g., an extracellular signal, across a membrane and the second molecule is an enzyme which can alter the phosphorylation state of tyrosine, e.g., a tyrosine kinase; the first molecule is an oncogene protein and the second molecule is an enzyme which can alter the phosphorylation state of tyrosine, e.g., a tyrosine kinase; the first molecule is the insulin receptor and the second molecule is an enzyme which can alter the phosphorylation state of tyrosine, e.g., a tyrosine kinase; the inhibitor molecule inhibits the first molecule from binding to the second molecule; the inhibitor molecule inhibits the phosphorylation of the first molecule; the inhibitor inhibits the binding of the first molecule to a third molecule; the inhibitor results in an alteration of a catalytic activity of the first molecule, e.g., the inhibitor alters the ability of the first molecule to alter the phosphorylation state of itself or another molecule.

In another aspect, the invention features a method of treating a mammal, e.g., a human, having a condition characterized by unwanted cell proliferation including administering to the mammal an amount of a peptide of the invention sufficient to prevent or inhibit the unwanted cell proliferation. In a preferred embodiment the peptide prevents the association of an SH2 domain containing oncogene with a second molecule, e.g., a protein containing the sequence Tyr-R$^1$-R$^2$-Met (SEQ ID NO: 1) (wherein R$^1$ is Met, Val, Ile, or Glu; and R$^2$ is any amino acid, but is preferably Pro, Met, Asp, Thr, Asn, Glu, or Tyr) e.g., Tyr-Met-R$^2$-Met (SEQ ID NO: 8), or the sequence Tyr-R$^1$-R$^2$-R$^3$ (SEQ ID NO: 2) (wherein R$^1$ is Glu, Asp, Thr, Tyr, His, or Gln; R$^2$ is Glu, Asn, Tyr, or Asp; and R$^3$ is Ile, Met, Leu, or Val) e.g., Tyr-Glu-Glu-Ile (SEQ ID NO: 3), e.g., a protein capable of altering the state of phosphorylation of a tyrosine residue, e.g., a tyrosine kinase.

In another aspect the invention features a method of synthesizing a peptide, e.g., a peptide of the invention, containing a phosphonomethylphenylalanine residue including:

providing a phosphonomethylphenylalanine preferably, with a protected phosphonate side chain; and incorporating the phosphonomethylphenylalanine into the peptide.

In preferred embodiments: the method further includes removing the protection group from the phosphonate side chain after the phosphonomethylphenylalanine has been incorporated into the peptide; and the protected phosphonate side chain is protected by a t-butyl group present as a t-butyl ester.

In another aspect, the invention features a peptide analog of a protein tyrosine phosphatase substrate, the substrate including a tyrosine residue. The analog includes an analog of phosphotyrosine having a hydrolysis resistant phosphorous moiety, e.g., a phosphonomethylphenylalanine residue, or a hydrolysis resistant phosphorous moiety which is more electronegative than the phosphate group of phosphotyrosine, for example, FPmp or $F_2$Pmp; in place of a tyrosine residue and is capable of inhibiting dephosphorylation of the substrate by a tyrosine phosphatase.

In preferred embodiments, the analog includes one of the peptides of the invention described above, e.g., the sequence Pmp-Met-$R^1$-Met (SEQ ID NO: 6), FPmp-Met-$R^1$-Met (SEQ ID NO: 6) or $F_2$Pmp-Met-$R^1$-Met (SEQ ID NO: 6), wherein Pmp is phosphonomethylphenylalanine $R_1$ is any amino acid; the analog is between 4 and 30, and more preferably between 4 and 15, amino acids in length.

In other preferred embodiments, the analog is at least 40%, preferably at least 80%, and more preferably at least 95% homologous with a naturally occurring tyrosine phosphatase substrate.

In yet another preferred embodiment, the analog has the sequence RDIPmpETDYYRK (SEQ ID NO: 9), RDIYETDPmpYRK (SEQ ID NO: 10), RDIYETDYPmpRK (SEQ ID NO: 11), TEPEPmpQPGE (SEQ ID NO: 12), KDESIDPmpVPMI,DMKGD (SEQ ID NO: 13), RENEPmpMPMAPQIH (SEQ ID NO: 14), TDDGPmpMPMSPGV (SEQ ID NO: 15), GNGDPmpMPMSPKS (SEQ ID NO: 16), RDI[L-Pmp]ETDYYRK (SEQ ID NO: 17), RDI[D-Pmp]ETDYYRK (SEQ ID NO: 18), RDIPmpETDPmpPmpRK (SEQ ID NO: 19), RDIF$_2$PmpETDYYRK (SEQ ID NO: 9), RDIYETDF$_2$PmpYRK (SEQ ID NO: 10), RDIYETDYF$_2$PmpRK (SEQ ID NO: 11), TEPEF$_2$PmpQPGE (SEQ ID NO: 12), KDESIDF$_2$PmpVPMLDMKGD (SEQ ID NO: 13), RENEF$_2$PmpMPMAPQIH (SEQ ID NO: 14), TDDGF$_2$PmpMPMSPGV (SEQ ID NO: 15), GNGDF$_2$PmpMPMSPKS (SEQ ID NO: 16), RDI[L-F$_2$Pmp]ETDYYRK (SEQ ID NO: 17), RDI[D-F$_2$Pmp]ETDYYRK (SEQ ID NO: 18), RDIF$_2$PmpETDF$_2$PmpF$_2$PmpRK (SEQ ID NO: 19), RDIFPmpETFDYYRK (SEQ ID NO: 9), RDIYETDFPmpYRK (SEQ ID NO: 10), RDIYETDYFPmpRK (SEQ ID NO: 11), TEPEFPmpQPGE (SEQ ID NO: 12), KDESIDFPmpVPMLDMKGD (SEQ ID NO: 13), RENEFPmpMPMAPQIH (SEQ ID NO: 14), TDDGFPmpMPMSPGV (SEQ ID NO: 15), GNGDFPmpMPMSPKS (SEQ ID NO: 16), RDI[L-FPmp]ETDYYRK (SEQ ID NO: 17), RDI[D-FPmp]ETDYYRK (SEQ ID NO: 18), or RDIFPmpETDFPmpFPmpRK (SEQ ID NO: 19).

The invention also includes a method of inhibiting the dephosphorylation of a substrate by a protein tyrosine phosphatase. The method includes contacting the protein tyrosine phosphatase with an inhibiting amount of an analog of a naturally occurring protein tyrosine phosphatase substrate, the analog including an analog of phosphotyrosine having a hydrolysis resistant phosphorous moiety, e.g., phosphonomethylphenylalanine or a hydrolysis resistant phosphorous moiety which is more electronegative than the phosphate group of phosphotyrosine, for example, FPmp or $F_2$Pmp.

The analog can be one which is at least 50, 60, 70, 80, 90, or 100% homologous with a fragment of a phosphoprotein which interacts with the SH2 domain-containing protein and which contains a tyrosine residue of the phosphoprotein, e.g., a phosphotyrosine which is at the site which binds the SH2 domain. In more preferred embodiments the analog is at least 3, 5, 10, or 15, amino acid residues in length. In more preferred embodiments the analog is less than 10, 15, 20, 30 or 40 amino acid residues in length. In preferred embodiments the analog has an $ED_{50}$ or $IC_{50}$ of less than 500, 100, 10, 1, or 0.1 µM for inhibiting binding of the phosphoprotein to an SH2 domain containing protein or fragment thereof.

The invention also includes a method of treating a mammal e.g., a human, afflicted with a disease or disorder characterized by the dephosphorylation of a protein tyrosine phosphatase substrate. The method includes administering to the mammal an inhibiting amount of a peptide analog of a naturally occurring protein tyrosine phosphatase substrate, the analog including an analog of phosphotyrosine having a hydrolysis resistant phosphorous moiety, e.g., phosphonomethylphenylalanine or a hydrolysis resistant phosphorous moiety which is more electronegative than the phosphate group of phosphotyrosine, for example, FPmp or $F_2$Pmp.

The invention includes methods of increasing the affinity of a phosphopeptide for its substrate, e.g., a protein containing a SH2-domain. The method includes replacing the phosphate moiety of a phosphotyrosine with a moiety which is more electronegative than the phosphate moiety of phosphotyrosine such as in $R^1$—$OPO_3H_2$ where $R^1$ can be CHF, $CF_2$, CHCl, $CCl_2$, or CClF.

The invention includes peptides which have been modified to make them more resistant to proteolytic degradation and include e.g., depsipeptide derivatives of the peptides disclosed herein, e.g., peptides which have been modified by the reduction of amide bonds, the inclusion of D-amino acids, or end methylation.

Signal transduction protein, as used herein, refers to a protein involved in transferring, a signal from the cell surface into the cell and includes, e.g., membrane bound receptors, e.g., cell surface receptors, ligands of such receptors, and intracellular proteins which interact with either with a receptor, or with another intracellular protein to transfer a signal.

SH2 domain, as used herein, refers to a conserved apparently noncatalytic sequence of approximately 100 amino acids found in many signal transduction proteins including Fps, Stc, AbI, GAP, PLCλ, v-Crk, Nck, p85, and Vav. See Koch et al., 1991, Science 252:668, hereby incorporated by reference. The amino acid sequences of the SH2 domain of 27 proteins is given in Koch et al., 1991. The SH2 domain mediates protein-protein interactions between the SH2 containing protein and other proteins by recognition of a specific site on a second protein. The SH2/second protein site interaction usually results in an association of the SH2 contacting protein and the second protein. As used herein, SH2 domain refers to any sequence with at least 70%, preferably at least 80%, and more preferably at least 90% sequence homology with a naturally occurring SH2 domain, and to any analog or fragment of an SH2 domain which exhibits at least 50% of the binding activity of a naturally occurring variant of that domain, when binding is measured as the ability to bind a YMXM (SEQ ID NO: 20) containing peptide.

An interaction between an SH2 domain containing protein and a second molecule e.g., a protein, as used herein, refers to any of: binding characterized by noncovalent or covalent interactions; an interaction which includes the alteration of the phosphorylation state of either the SH2 domain containing or another molecule, e.g., the second molecule; or to an interaction which includes an alteration of a catalytic ability of the SH2 domain containing proteins, or another molecule, e.g., the second molecule.

Analog of phosphotyrosine having a hydrolysis resistant phosphorous moiety, as used herein, refers to an amino acid with a side chain having a moiety of the formula

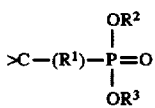

wherein $R^1$ is a moiety which renders the phosphate group more resistant to enzymatic hydrolysis than would be the case if the $R^1$ was O. $R^2$ and $R^3$ are preferably H. A preferred example of $R^1$ is $CR^4R^5$, wherein $R^4$ is H, or a small electronegative atom, e.g., F or Cl, and $R^5$ is H or a small electronegative atom, e.g., F or Cl.

Particularly preferred embodiments of the invention include hydrolysis resistant phosphorous moieties that are more electronegative than the phosphate moiety of phosphotyrosine, for example, where $R^1$ is —CHF, —CF$_2$, —CClF, —CHCl, or CCl$_2$.

Increasing the electronegativity of the phosphate moiety in an analog of phosphotyrosine increases the binding affinity of peptides containing the analog to a substrate such as protein containing an SH2 domain. In some cases, the affinity can exceed that of peptides containing phosphotyrosine.

The invention also includes mimics, e.g., small molecules, e.g., peptomimetics, of the peptides of the invention. The invention provides for reduction of the subject peptides to generate mimetics, e.g. peptide or non-peptide agents or other small molecules, which are able to mimic binding of a peptide described herein to an SH2 domain containing protein.

For instance, non-hydrolyzable peptide analogs of certain amino acid residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Eluffinan et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), b-turn dipeptide cores (Nagai et al. (1985) *Tetrahedron Lett* 26:647; and Sato et al. (1986) *J Chem Soc Perkin Trans* 1:1231), and b-aminoalcohols (Gordon et al. (1985) *Biochem Biophys Res Commun* 126:419; and Dann et al. (1986) *Biochem Biophys Res Commun* 134:71).

Abbreviations: mT, polyoma virus middle T antigen; mT/pp60$^{c-src}$, polyoma virus middle T antigen/pp60$^{c-src}$ complex; PtdIns 3-kinase, phosphatidylinositol 3-(hydroxy) kinase; PtdIns, phosphatidylinositol; PtdIns-3-P, phosphatidylinositol 3-phosphate; PtdIns-4-P, phosphatidylinositol 4-phosphate; PtdIns-4,5-P$_2$, phosphatidylinositol 4,5-bisphosphate; PtdIns-3,4-P$_2$, phosphatidylinositol 3,4-bisphosphate; PtdIns-3,4,5-P$_3$, phosphatidylinositol 3,4,5-triphosphate; PtdInsP, phosphatidylinositol phosphate; PtdInsP$_2$, phosphatidylinositol bisphosphate HEPES, 4-(hydroxyethyl)-1-piperazineethanesulfonic acid; HPLC, high performance liquid chromatography; PAGE, polyacrylamide gel electrophoresis; IRS-1, insulin receptor substrate 1.

SH2 domain containing proteins are involved in cellular signaling, e.g., in the signal transduction mediated by insulin and the insulin receptor and by several classes of oncogenes. The invention provides for inhibitors of these cellular signal transduction systems by inhibiting an interaction between the SH2 domain of the signal transduction protein and a YMXM (SEQ ID NO: 20) motif present on another protein. In the case of oncogenes, the invention provides for interference with the transduction of growth signals and thereby allows for control of unwanted cellular proliferation.

The invention also provides peptide inhibitors of PTPases. The peptide inhibitors, or analogs, which may or may not have homology with naturally occurring protein tyrosine phosphatase substrates, include an analog of phosphotyrosine having a hydrolysis resistant phosphorous moiety, e.g., phosphonomethylphenylalanine or a hydrolysis resistant phosphorous moiety which is more electronegative than the phosphate group of phosphotyrosine, for example, FPmp or F$_2$PmP. The phosphotyrosine analog includes a phenyl group substituted with an —O—PO$_3$H$_2$ analog, e.g., —R—PO$_3$H$_2$, where R can be any group which confers greater resistance to hydrolysis than does —O—, e.g, $CR^4R^5$ wherein $R^4$ can be H. F or Cl and $R^5$ can be H, F or Cl. Preferred phosphotyrosine analogs are phosphonomethylphenylalanine and mono- or difluorophosphonomethylphenylalanine.

Peptide inhibitors of the invention can have homology with PTPase substrates. The sequence of these inhibitors can be based on the amino acid sequences of kinase autophosphorylation and endogenous substrate phosphorylation sites.

The invention provides for the incorporation of Pmp into peptides using derivatives of Fmoc-Pmp in which the P—OH groups are protected as t-butyl esters. This procedure minimizes the yield of impurities arising from side reactions with free P—OH groups. Pmp-peptides are useful, e.g., as nonhydrolyzable inhibitors and affinity ligands of proteins having phosphotyrosine as part of a recognition element.

Phosphonomethylphenylalanyl peptides and mono- and difluorophosphonomethylphenylalanyl peptides constitute new classes of compounds that potently inhibit PTPase activity. Pmp-peptides appear to act as direct substrate mimics, as binding affinity closely matches that of the corresponding phosphopeptides and inhibition is competitive. F$_2$Pmp peptides also appear to act as direct substrate mimics. However, binding affinity of the F$_2$Pmp-peptides can match or exceed that of the corresponding phosphopeptides. Inhibitors of the invention allow the inhibition of cellular PTPases and can be used in controlling metabolic processes, e.g., abnormal processes associated with diabetes, and as therapeutic modalities for selected malignancies. The inhibitors are also useful to study the enzymatic mechanisms of PTPase activity and to investigate the metabolic and biochemical roles of PTPases.

Other features and advantages of the invention will be apparent from the following description of the preferred embodiments and from the claims.

DETAILED DESCRIPTION

Figures 1A, 1B, 1C:
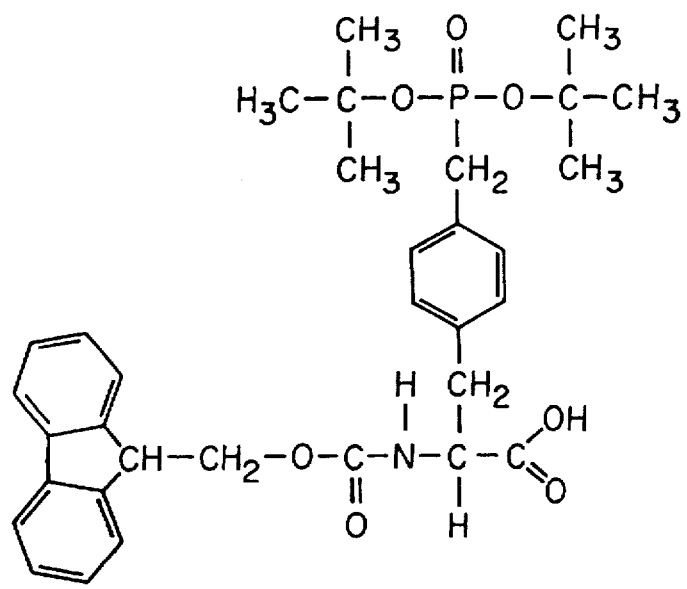

The drawings are first briefly described,

Drawings FIG. 1 is a diagram of Fmoc-Pmp (tBU)$_2$—OH (FIG. 1A) and two Pmp-containing peptides (FIG. 1B (SEQ ID NO: 44) and 1C (SEQ ID NO: 21)).

Figure 2:
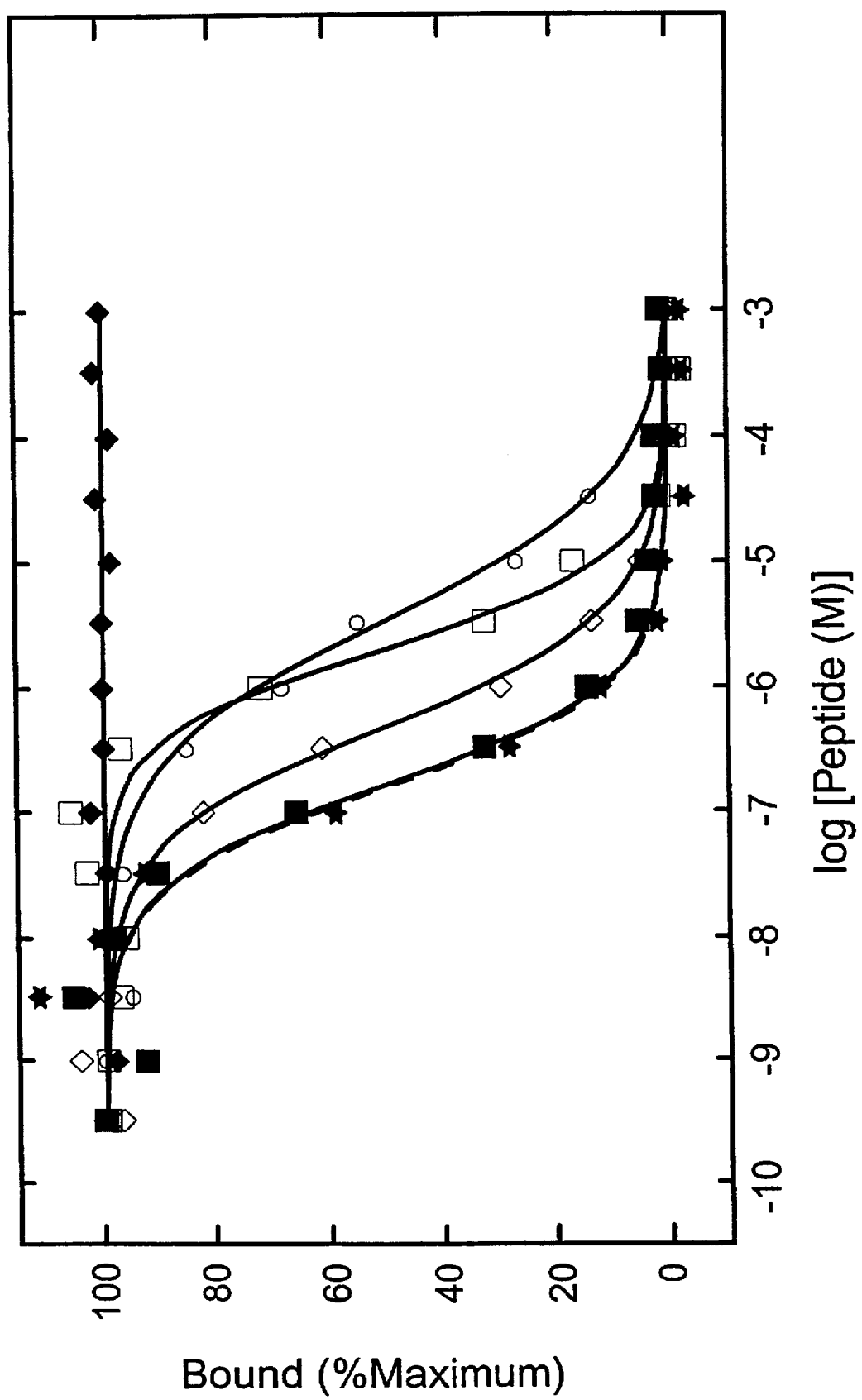

FIG. 2 is a graph of the results of a binding study. Phosphotyrosine (■) was replaced in the peptide GXVPML (SEQ ID NO: 45) by Pmp (□), monofluorophosphonomethylphenylalanine (FPmp) (◊), $F_2$Pmp, (star), hydroxyfluorophosphonomethylphenylalanine (HPmp) (○), and tyrosine (Tyr) (♦). The $ED_{50}$ values were 0.17±0.02 μM for pTyr, 1.0±0.1 μM for Pmp, 0.50±0.03 μM for FPmp, 0.17±0.02 μM for $F_2$Pmp, 3.3±0.5 μM for HPmp, and >1,000 μM for Tyr.

Figure 3A:
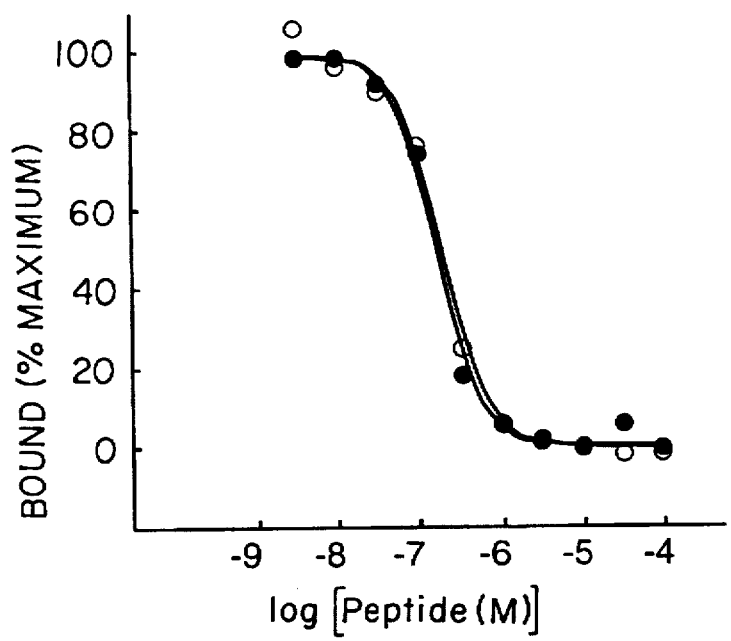
Figure 3B:
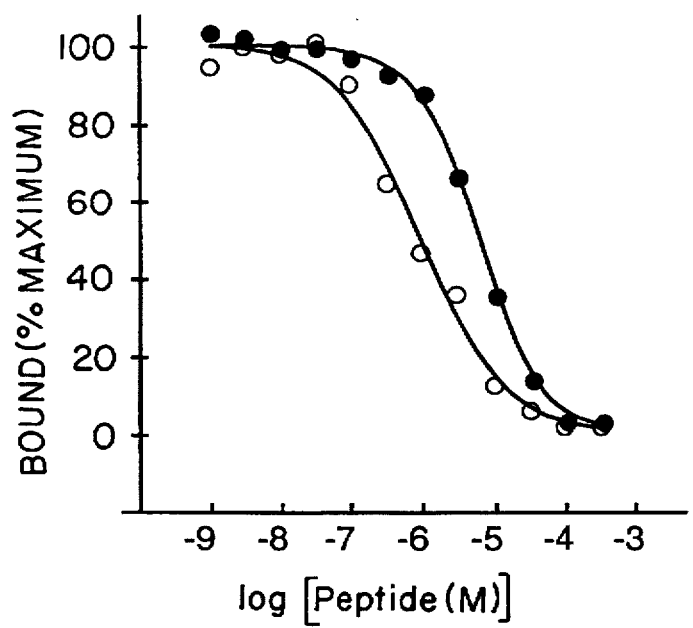
Figure 3C:
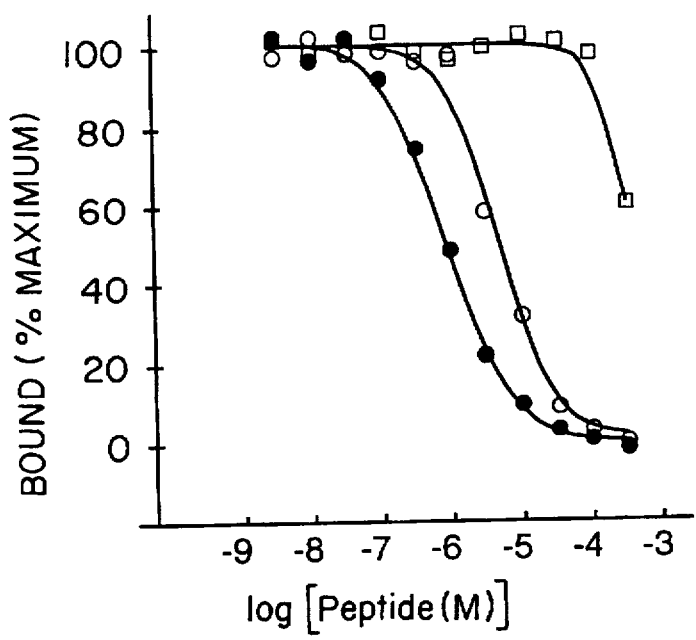

FIG. 3 is a depiction of: panel A, the binding affinity of the peptide DXVPML (SEQ ID NO:46) for the $SH_2$ domain of PI 3-kinase where X was pTyr (●) or $F_2$Pmp (○), the $ED_{50}$ values were 0.15±0.03 μM pTyr and 0.17±0.02 μM for $F_2$Pmp; panel B, the binding affinity of the peptide QXEEIP (SEQ ID NO:47) for the $SH_2$ domain of Src where X was pTyr (●) or $F_2$Pmp (○), the $ED_{50}$ values were 5.7±0.7 μM for pTyr and 1.0±0.2 μM for $F_2$Pmp: panel C, the binding affinity of the peptide NXVNIE (SEQ ID NO: 48) for the $SH_2$ region of Grb2 where X was pTyr (●), L-$F_2$Pmp(○), or D-$F_2$Pmp(□), the $ED_{50}$ values were 0.9±0.1 μM for pTyr, 4.7±0.7 μM for L-$F_2$Pmp, and >300 μM for D-$F_2$Pmp.

Figure 4:
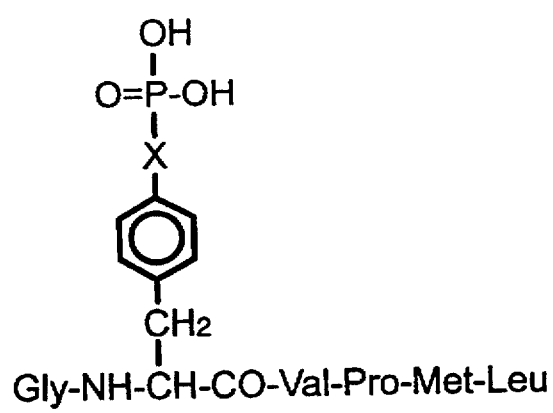

FIG. 4 is a diagram of the peptide GXVPML (SEQ ID NO: 45) where X in the diagram can be $CH_2$, CHF, $CF_2$, CHOH. The phosphate group (—$XPO_3H_2$) can be OH.

Solid-phase synthesis of nonhydrolyzable phosphotyrosyl peptide analogues with $N^\alpha$-Fmoc-(O,O-di-t-butyl) phosphono-p-methylphenylalanine Phosphonomethylphenylalanine (Pmp) is a non-natural analogue of phosphotyrosine in which the >C—O—$PO_3H_2$ moiety of is replaced by >C—$CH_2$—$PO_3H_2$. Unlike the phenyl phosphate ester of phosphotyrosine, the carbon-phosphorus bond of Pmp is stable to chemical and enzyme-catalyzed hydrolysis. Incorporation of Pmp into specific peptide sequences yields phosphopeptide analogs which are stable to the actions of cellular PTPases. Pmp has been prepared previously, Marseigne et al., 1988, J. Org. Chem. 53:3621, and incorporated into small peptides with the phosphonate side chain unprotected, Chatterjee et al., 1991, 12th Amer. Peptide Symp. Elsevier Press. The incorporation of Pmp into peptides using a newly developed derivative of Fmoc-Pmp in which the P—OH groups are protected as t-butyl esters is described below. This procedure minimizes impurities arising from side reactions with free P—OH groups.

Racemic $N^\alpha$-Fmoc-(O,O-di-t-butyl)phosphono-p-methylphenylalanine (Fmoc-Pmp(tBu)$_2$—OH) (see FIG. 1A) was prepared in three steps from α-(O,O-di-t-butylphosphono)-p-tolualdehyde, Burke et al., 1991, J. Med. Chem., 34:1577, in 48% overall yield, Burke et al., Synthesis. The new derivative was used to synthesize inhibitory peptides, e.g., the 11-amino acid peptide corresponding to a mono-phosphorylated sequence of the insulin receptor (residues 1155–1165), Ebina et al., 1985, Cell, 40:747; White et al., 1988, J. Biol. Chem., 263:2969, (see FIG. 1B) (SEQ ID NO: 44) and the 13-amino acid peptide corresponding to a putative phosphorylation site of the hamster polyoma virus transforming protein, middle T, Delmas et al., 1985, EMBO J., 4:1279, (see FIG. 1C) (SEQ ID NO: 21).

Syntheses were conducted on a Milligen/Biosearch 9600 synthesizer using 4-alkoxybenzyl alcohol polystyrene resin (PAC, Milligen/Biosearch) with the first residues attached to the resin at 0.35 to 0.37 mmol/g substitution levels. Acylation reactions preceding incorporation of Pmp were for 1 h at 22° C. with 4 equivalents each of $N^\alpha$-Fmoc amino acid, 1-hydroxybenzotriazole and diisopropylcarbodiimide in DMF, while coupling reactions for residues following Pmp were for 4 h (side chain protecting groups were Asn(Trt), Arg(Pmc), Asp(tBu), Glu(tBu), His(Trt), Lys(Boc), Thr(tBu)). Peptide bond forming reactions with Fmoc-Pmp(tBu)$_2$—OH were conducted manually for 2 h with 3 equivalents of each reagent; couplings were complete by ninhydrin test and no additional precautions were taken with Fmoc-Pmp(tBU)$_2$—OH. $N^\alpha$-Fmoc deprotections were carried out with a mixture of piperidine, toluene and DMF (30:35:35), v/v/v) for seven minutes. Peptides were cleaved from the resin and side chain protecting groups removed by treatment with a mixture of trifluoroacetic acid, thioanisole, ethanedithiol and anisole (90:5:3:2 by volume) for 2 h at 4° C. Cleaved peptides were precipitated in diethyl ether, desalted on a column (2.6×100 cm) of Bio-Gel P2 which had been equilibrated in 3M acetic acid, and lyophilized.

Peptide products were separated by analytical HPLC into two major components which correspond to the expected enantiomeric products resulting from use of racemic Fmoc-Pmp(tBu)$_2$—OH. The reversed-phase HPLC analyses of the crude products was obtained following synthesis of inhibitory peptides; a Bio-Rad RP-318 column (4.6×250 mm) was eluted at 1.0 ml/min with 0–70% acetonitrile in 0.05% trifluoroacetic acid. Peptides containing D- and L-Pmp were readily separated from one another by release of L-Pmp only following treatment with leucine aminopeptidase, Miller et al., 1988, Proc. Natl. Acad. Sci., USA, 85:5429, (IUB 3.4.11.1; Worthington); in each case shown this was the earlier-eluting peptide. Peptides from both HPLC fractions gave identical results by plasma desorption mass spectrometry, (results from plasma desorption mass spectrometry (ABI Biolon): D- and L-isomers, the insulin receptor peptide (SEQ ID NO: 9) molecular ions at m/z 1601.7 and 1601.8; D- and L-isomers. The polyoma virus peptide (SEQ ID NO: 20), molecular ions at m/z 1696.3 and 1694.8), and amino acid analysis, which were entirely consistent with the expected compositions.

These results show that Fmoc-Pmp(tBu)$_2$—OH can be incorporated into peptide sequences and the t-butyl protecting groups can be removed under standard conditions of peptide synthesis in the absence of substantial side reactions. Although a solid-phase synthetic strategy using carbodiimide-based peptide bond formation was used here, the protected derivative will be useful for additional synthetic strategies, as well. Resulting Pmp-peptides are useful, e.g., as nonhydrolyzable inhibitors and affinity ligands of proteins having phosphotyrosine as part of a recognition element, including PTPases, Cohen et al., 1989, J. Biol. Chem., 264:21435; Hunter, 1989, Cell, 58:1013; Fischer et al., 1991, Cell, 64:281 and additional proteins involved in cellular pathways of signal transduction, Ullrich et al., 1990, Cell, 61:203; Hunter, 1989, Curr. Opin. Cell Biol., 1168; Koch et al., 1991, Science, 252:668; Cantley et al., 1991, Cell, 64:281.

Inhibition of the interaction between IRS-1 and PtdIns 3-kinase

IRS-1 is an endogenous substrate of the insulin receptor that associates with PI 3-kinase following insulin stimulation of intact cells, Sun et al., 1991, Nature 352:73. Peptides corresponding to suspected IRS-1 phosphorylation sites were prepared. YMXM (SEQ ID NO: 20) sequences were found to be phosphorylated much more efficiently than other sequences. Methionine residues at the Y+1 and Y+3 positions of the YMXM (SEQ ID NO: 6) motif are necessary for directing insulin kinase action efficiently. Phosphopeptides corresponding to YMXM (SEQ ID NO: 20) sequences and autophosphorylation sites of the insulin receptor and src were prepared. Phosphorylated YMXM (SEQ ID NO: 20) peptides had the unique ability to inhibit interaction of IRS-1 with PI 3-kinase activity. Unphosphorylated YMXM (SEQ ID NO: 01) sequences and other phosphopeptides had no effect. These experiments are discussed in detail below.

Binding of peptides to IRS-1 Initial kinase experiments were performed with peptides corresponding to sequences of IRS-1 surrounding tyrosine residues (Table 1).

TABLE 1

Peptide Sequences of IRS-1

Position/Name  Sequence

A. Double Tyr

Y46    R—L—E—Y—Y—E—N—E—K—K (SEQ ID NO: 22)

B. YXXM Motifs

Y460   K—R—G—E—E—E—I—S—N—Y—I—C—M—G—G—K (SEQ ID NO: 23)
Y546   K—K—V—S—I—E—E—Y—T—E—M—M—P—A—K (SEQ ID NO: 24)

C. YMXM Motifs

Y608   K—K—H—T—D—D—G—Y—M—P—M—S—P—G—V—A (SEQ ID NO: 25)
Y628   R—K—G—N—G—D—G—Y—M—P—M—S—P—K—S—V (SEQ ID NO: 26)
Y658   K—K—R—V—D—P—N—G—Y—M—M—M—S—P—S—G—S (SEQ ID NO: 27)
Y727   K—K—L—P—A—T—G—D—Y—M—N—M—S—P—V—G—D (SEQ ID NO: 28)
Y939   K—K—G—S—E—E—Y—M—N—M—D—L—G—P—G—R (SEQ ID NO: 29)
Y987   K—K—S—R—G—D—Y—M—T—M—Q—I—G (SEQ ID NO: 30)

D. Non-Specific Sequence

Y998   K—P—R—N—S—Y—V—D—T—S—P—V—A—P—K (SEQ ID NO: 31)

Peptides were phosphorylated by insulin and ATP-activated receptors in a time and temperature dependent fashion to display saturable kinetics and linear Lineweaver-Burk plots. Great variations in rates of peptide phosphorylation ($V_{max}$) and peptide concentrations required for half-maximal saturation ($K_m$) were found. Slopes of double reciprocal plots, which are proportional to $K_m/V_{max}$ (the inverse of catalytic efficiency), clustered into two groups. Native sequences having entire YMXM (SEQ ID NO: 6) motifs displayed the smallest slopes and were therefore, phosphorylated most efficiently. By contrast, YXXM-peptides and other sequences not containing complete YMXM motifs all displayed steeper slopes, demonstrating that they were phosphorylated less efficiently.

Calculation of rate constants revealed that Km values for YMXM-peptides ranged from 13 to 92 μM, lower than values previously reported for peptide substrates of the insulin receptor. Values for $V_{max}$, which range from 0.9 to 1.7 pmol/min (69 to 131 nmol/min/mg), are difficult to compare to previous studies as this number varies with kinase specific activity.

Values for $k_{cat}/K_m$ range from 0.6–3.6×10$^4$M$^{-1}$s$^{-1}$. Therefore, in terms of substrate binding (estimated by $K_m$), turnover rates ($V_{max}$ or $k_{cat}$), and overall catalytic efficiency ($k_{cat}/K_m$) all of the YMXM peptide sequences are excellent substrates of the insulin receptor kinase. YXYM-peptides were phosphorylated less efficiently. To test why, positions within peptide Y987 were substituted and subjected to similar kinase assays. Met$^{Y+1}$ substitutions (Ile, Thr) reduced catalytic efficiency ($k_{cat}/K_m$) nearly 5-fold, while norleucine, whose side chain mimics that of methionine regarding both hydrophobicity and flexibility, had no observable effect. Surprisingly, a Met$^{Y+3}$→Thr substitution had an even greater effect on phosphorylation efficiency, with a 12-fold reduction in $k_{cat}/K_m$ resulting exclusively from an increase in $K_m$. The only acidic residue in the Y987 sequence was substituted (Asp→Asn) to assess the isolated effect of having no negative charge on N-terminal to tyrosine; $k_{cat}/K_m$ was reduced 2.5-fold, surprisingly less deleterious than substituting Met residues at either Y+1 or Y+3 positions. These results suggest that methionine at the +1 and +3 position plays a very special role in directing action of the insulin receptor kinase. The combined hydrophobic and flexible character of Met appears to be crucial for this effect.

Fmoc-pTyr(OMe)$_2$ or Fmoc-pTyr(OBzl)$_2$ can be used to prepare phosphorylated forms of YMXM peptides. Phosphopeptides having a mouse middle T antigen sequence (pY-midT, EEEpYMPMEDLY (SEQ ID NO: 32)), sequences from the kinase insert of the PDGF receptor (pY708, DGGpYMDMSKDE (SEQ ID NO: 33); pY719, SIDpYVPMLDMK (SEQ ID NO: 34)) and IRS-1 YMXM (SEQ ID NO: 20) sequences pY608 (SEQ ID NO: 25), pY628 (SEQ ID NO: 26), pY658 (SEQ ID NO: 27), pY727 (SEQ ID NO: 13), pY939 (SEQ ID NO: 29) and pY987 (SEQ ID NO: 30) (Table 1) have all been prepared, purified and characterized by amino acid analysis and FAB-MS.

Inhibiting interactions between IRS-1 and PI 3-kinase IRS-1 produced in a baculovirus expression system was adsorbed to anti-peptide (IRS-1) antibodies and phosphorylated by solubilized insulin receptors (which were then washed away). PI 3-kinase activity was obtained by solubilizing CHO cells with Triton X-100 and adding the mixture directly to the immunoprecipitated IRS-1. After incubation and additional washing, PI 3-kinase activity associated with the immobilized IRS-1 was determined as described, Auger et al. PI 3-kinase activity associated with IRS-1 only after phosphorylation by the insulin receptor. Various peptides were added during incubation of immobilized IRS-1 with the ChO cell extract (PI 3-kinase) to determine their ability to block association. Concentration dependent effects of phosphorylated vs. unphosphorylated middle T and IRS-1 Y628 YMXM sequences were determined. Only phosphorylated YMXM-peptides block IRS-1/PI 3-kinase association, and near total inhibition occurs even at 1 μM phosphopeptide. Recent doseresponse studies show that pY628 inhibits IRS-1/PI 3-kinase association with an $ED_{50} \leq 50$ nM. Corresponding unphosphorylated YMXM-peptides and additional phosphopeptides corresponding to the insulin receptor and src phosphorylation sites had no effect in this assay, suggesting a high degree of sequence specificity for phosphotyrosine within a YMXM sequence. A detailed study of these effects is a major target of this proposal.

Inhibition of the Interaction between PtdIns 3-Kinase and mT/pp60$^{c-src}$

Overview Purified PtdIns 3-kinase was reconstituted with recombinant, baculovirus-expressed, immunopurified mT/pp60$^{c-src}$ in vitro. The PtdIns 3-kinase associated with protein-tyrosine kinase-active mT/pp60$^{c-src}$ but failed to associate with an inactive mutant. ATP was not required during the precipitation indicating that phosphorylation of PtdIns 3-kinase itself was not needed for tight complex formation. Previous work has shown that the baculovirus-expressed mT/pp60$^{c-src}$ complex purified from sf9 cells is phosphorylated on tyr residues of mT while the kinase-inactive mutant is not, Piwnica-Worms et al., 1990, J. Virol. 64:61. The ability of the wild-type mT/pp60$^{c-src}$ complex but not the mutant to associate with PtdIns 3-kinase thus suggests that tyrosine phosphorylation of the mT/pp60$^{c-src}$ complex is needed for the association. This result is consistent with the observation that mT must be phosphorylated on tyr in order to blot the 85 kDa subunit of PtdIns 3-kinase using the western blot procedure, Carpenter et al., 1990, J. Biol. Chem. 265:19704; Cohen et al., 1990, Proc. Natl. Acad. Sci., USA 87:4458.

Consistent with this idea, a phosphotyrosine-containing peptide based on a region highly conserved between hamster and murine polyoma mT (Table 2) blocked association of PtdIns 3-kinase with mT/pp60$^{c-src}$.

TABLE 2

| PROTEIN | SEQUENCE | PHOSPHORYLATED TYROSINE (predicted*) |
|---|---|---|
| Hamster mT | RENEYMPMAPQIH (SEQ ID NO: 35) | 298 |
| Murine mT | EEEEYMPMEDLYL (SEQ ID NO: 36) | 315 |
| Rat IRS-1 | TDDGYMPMSPGVA (SEQ ID NO: 37) | 608* |
| Rat IRS-1 | GNGDYMPMSPKSV (SEQ ID NO: 38) | 628* |
| Rat IRS-1 | APVSYADMRTGIA (SEQ ID NO: 39) | 1010* |
| Human PDGF Rec. β | ESVDYVPMLDMKG (SEQ ID NO: 40) | 751 |
| Human PDGF Rec. β | SDGGYMDMSKDES (SEQ ID NO: 41) | 740 |

The non-phosphorylated peptide had no effect on the association. The phosphotyrosine of this sequence is analogous to tyr-315 of murine mT, the major site of tyrosine phosphorylation in vivo. A mutation of tyr-315 to phe reduced (but did not eliminate) association with PtdIns 3-kinase in vivo, Whitman et al., 1985, Nature 315:239 and an antibody against this region preferentially immunoprecipitates the fraction of mT that does not associate with PtdIns 3-kinase, Talmage et al., 1989, Cell, 59:55. Mutations in the region of tyr-315 also compromise the transforming ability of polyoma virus without affecting the tyrosine kinase activity of the mT/pp60$^{c-src}$ complex, indicating that this region is critical for in vivo targeting of the protein-tyrosine kinase, Cantley et al., 1991, Cell, 64:281. (These experiments are discussed in detail below).

As pointed out previously, receptor-type tyrosine kinases that bind PtdIns 3-kinase have short stretches of sequences with similarity to the tyr-315 region of mT, Cantley et al., 1991, supra. In the PDGF receptor, the sequences around tyr-740 and tyr-751 obey these rules (Table 2) and the latter site is known to be phosphorylated in response to PDGF binding, Kazlauskas et al., 1989, Cell, 58:1121. Both Tyr 751 and Tyr 740 have been implicated in binding PtdIns 3-kinase, Kazlauskas et al., 1989, supra; Kazlauskas et al., 1990, EMBO J., 9:3279; Heidaran et al., 1991, Mol. Cell. Biol., 11:134; Escobedo et al., 1991, Mol. Cell. Biol., 11:1125, and peptides phosphorylated at tyr-740 or tyr-751 have been shown to block association of purified PDGF receptor with PtdIns 3-kinase from cell lysates, Escobedo et al., 1991, supra. Thus, our results with mT/pp60$^{c-src}$ are analogous to the results with the PDGF receptor and extend these studies to show that purified PtdIns 3-kinase will complex with mT/pp60$^{c-src}$ without the need of other cellular factors.

In addition to receptor-type tyrosine kinase, a major substrate of the insulin receptor tyrosine (IRS-1) contains several repeats of sequences similar to the tyr-315 region of polyoma mT, Sun et al., 1991, Nature, 352:73, (Table 2). This protein is not a tyrosine kinase but associates with PtdIns 3-kinase in insulin-stimulated (but not unstimulated) cells, Sun et al., 1991, supra. IRS-1 has two regions of sequence that are quite similar to the hamster mt phosphopeptide used for competition studies reported herein (Table 2).

The results presented here provide the first evidence that the 110 kDa subunit of PtdIns 3-kinase associates with the mT/pp60$^{c-src}$ complex. The 110 kDa subunit was not phosphorylated as well as the 85 kDa subunit in the reconstituted complex and was not previously detected in $^{32}$PO$_4$3—labeled proteins associated with mT immunoprecipitates from polyoma-infected cells, Kaplan et al., 1987, Cell, 50:1021. However, using [$^{35}$S]-methionine labeled cells, the major proteins that associated with baculovirus-expressed mT/pp60$^{c-src}$ complex and failed to associate with the kinase-defective mutant migrated at the positions of the 110 kDa and 85 kDa subunits of the PtdIns 3-kinase. A third unidentified protein of higher molecular weight was also selectively immunoprecipitated with wild-type mT/pp60$^{c-src}$. The phosphopeptide specifically blocked association of the 85 kDa and 110 kDa proteins and the PtdIns 3-kinase activity. These results are consistent with the idea that both the 86 kDa and 110 kDa subunits of PtdIns 3-kinase associate with the mT/pp60$^{c-src}$ complex in polyoma infected cell and that these are the major cellular proteins that associate with the complex in a tyrosine-kinase dependent manner.

On the basis of previous results it is likely that the 85 kDa subunit of PtdIns 3-kinase is regulatory and provides the link between mT and the 110 kDa subunit. The 110 kDa subunit is probably the catalytic subunit, Shibasaki et al., 1991, J. Biol. Chem. 266:8108. The 85 kDa protein has two ~80 amino acid stretches of homology to the amino-terminal non-catalytic domain of pp60$_{c-src}$ (SH-2 domain), Ostu et al., 1991, Cell, 65:91; Escobedo et al., 1991, Cell, 65:75; Skolnik et al., 1991, Cell, 65:83. SH-2 domains have been shown to bind to tyrosine-phosphorylated regions of target proteins to form tight complexes both in vivo and in vitro (Anderson et al. (Pawson) 1990, reviewed in Cantley et al., 1991, supra, and (Pawson's Science review 1991)). Tyrosine-phosphorylated mT specifically blots the 85 kDa (but not the 110 kDa) subunit of PtdIns 3-kinase using a Western blot procedure, Carpenter et al., 1990, .supra; Cohen et al., 1990, supra.

Finally, constitution of PtdIns 3-kinase with mT/pp60$^{c-src}$ did not have a major affect on substrate specificity. The purified enzyme utilizes three substrates in vitro (PtdIns, PtdIns-4-P and PtdIns-4,5-P$_2$) and the relative activities toward these substrates are very sensitive to assay conditions, Carpenter et al., 1990, supra. Cells transformed with polyoma mT or stimulated with PDGF have increased levels of PtdIns-3,4-$P_2$ and PtdIns-3,4,5-$P_3$ but little change in PtdIns-3-P suggesting that transformation by polyoma or activation by PDGF enhances phosphorylation of PtdIns-4-P and/or PtdIns-4,5-$P_2$ by PtdIns 3-kinase, Auger et al., 1989, Cell, 57:167; Serunian et al., 1990, J. Virol., 64:4718; Ulug et al., 1990, J. Virol., 64:3895. Using standard assay conditions the ratio of products formed when a mixture of all three substrates is presented is similar whether pure enzyme, or reconstituted mT/pp60$^{c-src}$/PtdIns 3-kinase complex is used. The ratio is also similar to that found in mT immunoprecipitates from mT-transformed cells, Serunian et al., 1990, supra.

Association of immunopurified mT/pp60$^{c-src}$ with purified phosphatidylinositol 3-Kinase is dependent on protein-tyrosine kinase activity PtdIns 3-kinase associates with the mT/pp60$^{c-src}$ complex in vivo and can be immunoprecipitated from mT transformed cells using antibodies against mT or pp60$^{c-src}$, Whitman et al., 1985, supra; Kaplan et al., 1986, Proc. Natl. Acad. Sci., USA, 83:3624; Whitman et al., 1988, Nature, 332:644. The mT/pp60$^{c-src}$ complex has been generated in insect Sf9 cells by co-infection with baculovirus constructs that express the mT and c-src genes, Piwnica-Worms et al., 1990, supra. This complex has been shown to have protein-tyrosine kinase activity. Both mT and pp60$^{c-src}$ in the insect cell and the purified complex has tyrosine kinase activity toward exogenous substrates. A kinase-defective complex, mT/pp60$^{295c-src}$, has also been previously characterized. The pp60$^{295c-src}$ mutant protein associates with mT, but does not have protein tyrosine kinase activity, Piwnica-Worms et al., 1990, supra. The mT/pp60$^{c-src}$ and mT/pp60$^{295c-src}$ complexes were purified from baculovirus infected Sf9 cells using anti-middle T (α-mT) antibodies conjugated to protein-A Sepharose beads. The purified complexes lacked PtdIns 3-kinase activity, although a small amount of PtdInsP kinase activity was detected.

In order to test for in vitro association between the mT/pp60$^{c-src}$ complex and PtdIns 3-kinase, purified rat liver PtdIns 3-kinase, Carpenter et al., 1990, supra was incubated with the baculovirus-expressed mT/pp60$_{c-src}$. After incubation at 4° C., the beads containing the complex were washed and then assayed for lipid kinase activity. Gel electrophoresis experiments showed that PtdIns, PtdIns-4-P and PtdIns-4,5-$P_2$ kinase activities associated with the mT/pp60$^{c-src}$ complex when purified PtdIns 3-kinase was present. However, very little PtdIns kinase activity associated with the protein kinase deficient mutant mT/pp60$^{295c-src}$ complex. Thus, the in vitro association of PtdIns 3-kinase with the mT/pp60$^{c-src}$ complex appears to be dependent on the protein-tyrosine kinase activity of pp60$^{c-src}$ in the complex.

To confirm that the differences in PtdIns 3-kinase association with the mT/pp60$^{c-src}$ complex and mT/pp60$^{295c-src}$ complex were not simply due to the amount of complex immunoprecipitated, immunoprecipitations from Tran[35]S-labelled Sf9 cells were analyzed by SDS-polyacrylamide gel electrophoresis and autoradiography. Very similar if not identical amounts of 58 kDa (mT) and 60 kDa (src) proteins were immunoprecipitated in the mT/pp60$^{c-src}$ and mT/pp60$^{295c-src}$ complexes. Because equivalent amounts of the complexes were available for association with the PtdIns 3-kinase, these results suggest that the important difference is protein-tyrosine kinase activity. These results are consistent with previous in vivo findings that mT must associate with and activate pp$_{60}^{c-src}$ in order for PtdIns kinase to associate, Kaplan et al., 1986, supra; Talmage et al., 1989, supra.

These results demonstrate the ability of immunopurified mT/pp60$^{c-src}$ and purified PtdIns 3-kinase to associate in vivo. This association was also demonstrated by adding purified PtdIns 3-kinase directly to the insect cell lysate and incubating this mixture at 4° C. After incubation, α-mT antiserum was added and the immune complexes were collected on protein A-Sepharose, and then washed. Lipid kinase assays demonstrated that purified PtdIns 3-kinase still associated with the mT/pp60$^{c-src}$ complex in the crude insect cell lysate. A monoclonal antibody (EC10) directed against pp60$^{c-src}$ also immunoprecipitated the mT/pp60$^{c-src}$ complex and associated lipid kinase activity.

The gel electrophoresis analysis of phosphatidylinositol kinase reactions after association of purified rat liver PtdIns 3-kinase with baculovirus-expressed, immunopurified mT/pp60$^{c-src}$ and mT/pp60$^{295c-src}$ was performed as follows. The mT complexes were immunopurified as described herein and incubated with or without purified PtdIns 3-kinase at 4° C. for 2 hours in standard lysis buffer. Phosphatidylinositol kinase assays were done with a mixture of PtdS, PtdIns, PtdIns-4-P, and PtdIns-4,5-$P_2$ as lipid substrates (1:1:1:2). Immunopurified, baculovirus-expressed mT/pp60$^{c-src}$ and mT/pp60$^{295c-src}$ were used. Purified PtdIns 3-kinase was added or was omitted as herein and incubated with or without purified PtdIns 3-kinase at 4° C. for 2 hours in standard lysis buffer. Phosphatidylinositol kinase assays were done with a mixture of PtdS, PtdIns, PtdIns-4-P, and PtdIns-4,5-$P_2$ as lipid substrates (1:1:1:2). Immunopurified, baculovirus-expressed mT/pp60$^{c-src}$ and mT/pp60$^{295c-src}$ were used. Purified PtdIns 3-kinase was added or was omitted.

Preparation of Sf9 cell pellets, lysates, and immunoprecipitates was as follows. Sf9 cells were scrape-harvested from the cell culture plates in phosphate buffered saline (PBS) and collected by centrifugation. The cell pellet was washed once with cold PBS and aliquoted to 1.5 ml microcentrifuge tubes and again separated by centrifugation. The supernatant was aspirated from the cells and the pellets were quick-frozen in dry ice/ethanol and stored at −70° C. until the lysates were prepared.

Lysates were generated by addition of 1.0 ml of standard lysis buffer (137 mM NaCl, 20 mM Tris-HCl (pH 7.4), 1 mM MgCl$_2$, 1 mM CaCl$_2$, 10% glycerol, 1% NP-40, 150 μg/ml aprotinin and leupeptin) and incubated at 4° C. with constant rocking for 15 minutes. Lysates were cleared by centrifugation at 12,000×g for 5 minutes at 4° C. The mT/pp60$^{c-src}$ complex was purified by immunoprecipitation essentially as described, Auger et al., 1990, Methods in Inositide Research, 159. Briefly, α-mT antibodies were added to the lysates and incubated at 4° C. for 2 hours with constant agitation. The immune complexes were collected on protein A-Sepharose (CL 4B; Sigma) that had been pre-washed in 1% BSA and then stored in a 50% suspension with PBS. Immune complexes were washed 2 times with 1% NP-40 in PBS, 2 times with RIPA (20 mM HEPES (pH 7.5), 137 mM NaCl, 2 mM EDTA, 10% glycerol, 1% NP-40, 0.1% SDS, 0.5% deoxycholate), twice with 0.5M LiCl in 0.1M Tris-HCl (pH 7.4) and finally 2 times with TNE (10 mM Tris-HCl (pH 7.4), 100 mM NaCl, 1 mM EDTA). The immunoprecipitates were used immediately for in vitro phosphorylation and association assays.

Purification of phosphatidylinositol 3-kinase was as follows. PtdIns 3-kinase was purified to homogeneity from rat liver as previously described, Carpenter et al., 1990, supra. The purified enzyme had a specific activity of approximately 500 nmol/mg/min when assayed as described below with PtdIns as the substrate. The enzyme was stored to 4° C. in 50 mM MES (pH 6.7), 100 mM KCl, 0.5 mM DTT, 1 μg/ml of leupeptin and pepstatin A and used within two weeks of purification.

In vitro association of phosphatidylinositol 3-kinase with immunopurified mT/pp60$^{c-src}$ was assayed as follows. Washed mT/pp60$^{c-src}$ immune complexes were incubated with purified PtdIns 3-kinase in 750 μl to 1 ml of standard lysis buffer (see above) at 4° C. on a platform rocker. The typical incubation was for 2–3 hours after which the complexes were collected by a brief centrifugation and washed twice with 1% NP-in 40 PBS, twice with 0.5M LiCl in 0.1M Tris-HCl, and twice with TNE.

Mammalian whole cell lysates were prepared from confluent 10 cm cell culture plates. The monolayer was washed once with 4° C. PBS and lysed in 1.0 ml of standard lysis buffer. After 10 minutes of incubation on a rocker platform at 4° C., the cells were scrape harvested and lysates cleared by centrifugation at 12,000×g for 5 minutes at 4° C. Lysates were used immediately for association experiments with the immunopurified mT/pp60$^{c-src}$ complex.

Phosphatidylinositol kinase assays and protein kinase assays were performed as follows. Phosphatidylinositol kinase assays were performed directly on the immune complex as described, Whitman et al., 1985, supra; Auger et al., 1989, supra. Sonicated phospholipids were added to the washed beads and the reaction was initiated with the addition of 50 μM ATP, 5–25 μCi [γ$^{32}$P]ATP (3000/Ci/mmole), 5 mM MgCl2 in 20 mM HEPES (pH 7.5). Reactions were incubated for 5 minutes at room temperature. The 50 μl reactions were stopped by the addition of 80 μl of 1M HCl and 1 μl of 500 mM EDTA. The lipids were extracted with 160 μl of methanol:chloroform (1:1) and the organic layer was collected for analysis.

Protein kinase assay were also performed directly on the immune complex with or without added PtdIns 3-kinase. The reaction was done in 20 mM HEPES (pH 7.4), 10 mM MgCl$_2$, 1–5 μM ATP and typically 10–50 μCi [γ$^{32}$P]ATP (3000/Ci/mmole) per assay. Experiments for the time course of phosphorylation of PtdIns 3-kinase by the mT/pp60$^{c-src}$ complex were done with 100 μM ATP. To analyze the phosphorylation of purified PtdIns 3-kinase, the purified enzyme was added directly to the washed immune complex prior to the protein kinase reaction. The reaction was stopped by the addition of 2× SDS-gel loading buffer and samples were boiled for 5 minutes prior to SDS-PAGE.

Phosphoamino acid analysis was performed as follows. Phosphoamino acid analysis of the [$^{32}$P]-labelled proteins from the SDS-gel was performed as described, Parker et al., 1991, Embo J., 10:1255. Briefly, radioactive gel slices were excised after autoradiography, fixed in 30% methanol for several hours and dried to roto-evaporation. The gel slices were treated with TPCK trypsin (Worthington Biochemical Corporation) in 50 mM ammonium bicarbonate at 37° C. overnight. The supernatants were collected and dried; and washed with successively decreasing volumes of H$_2$O (e.g., 1 ml, 500 μl, 300 μl, 200 μl, 100 μl). The tryptic fragments were hydrolyzed with 6M HCl at 100° C. for 90 minutes. Samples were then dried and washed with H$_2$O. The samples were dissolved and analyzed by electrophoresis in pyridine : acetic acid : water (1:10:189; v:v:v) for 90 minutes at 800 volts with nonradioactive standards. The standards were visualized by spraying with 0.2% ninhydrin in acetone, and radiolabelled samples were visualized by autoradiography.

Two dimensional analysis was also performed as described, Parker et al., 1991, supra. Electrophoretic separation in the first dimension was done in formic acid : acetic acid : H$_2$O (25:78:897; v:v:v). Plates were thoroughly dried and then developed by ascending chromatography for the second dimension in an isopropanol:HCl: H$_2$O (70:15:15; v:v:v) solvent system. Standards and samples were visualized as described above.

Tran$^{35}$S-labelling of NIH/3T3 cells, Rat-1 cells, and Sf9 cells was performed as follows. NIH/3T3 cells were grown to approximately 80–90% confluence in 10 cm plates in DME supplemented to contain 10% CS. The culture medium was removed and replaced with 5 ml of DME minus methionine (Gibco) that contained 500μCi Tran$^{35}$S-label (ICN,>1000 Ci/mmole) supplemented with one third of the amount of unlabeled methionine normally used. The cells were cultured for 12–48 hours and then harvested as follows: Radioactive culture medium was aspirated and the cell monolayer was washed 2 times with ice-cold PBS.

The cells were lysed by the addition of 1 ml of standard lysis buffer (see above) and incubated on a rocker platform for 15–20 minutes at 4° C. The lysate was harvested with the aid of a cell scraper and cleared of insoluble material by centrifugation at 12,000×g for 5 minutes at 4° C. The lysates were used immediately for association assays. Sf9 cells were labelled at 38–40 hours post-infection with Tran$^{35}$S-label as described, Piwnica-Worms et al., 1990, supra.

Thin layer chromatography, deacylation of phospholipids, and HPLC analysis were performed as follows. Intact phospholipids were analyzed on oxalate treated silica gel 60 plates (E. Merck) in a solvent system of n-propanol:2M acetic acid (65:35, v:v). For experiments in which only PtdInsP and/or PtdInsP2 were analyzed, the faster chloroform methanol:2.2M NH$_4$OH (9:7:2; v:v:v) solvent system was utilized. Phospholipids were deacylated and analyzed by HPLC as previously described, Auger et al., 1990, supra. [$^3$H]-labelled phosphoinositides and inositol standards were obtained from DuPont New England Nuclear and the lipids were deacylated by the same methods used for the $^{32}$P-labelled samples. The standards and samples were co-injected with the nonradioactive nucleotides ADP and ATP for each HPLC analysis.

Cell culture was performed as follows. NIH/3T3 and Rat-1 fibroblasts were maintained by standard cell culture techniques in DME supplemented to contain 10% calf serum (CS). Spodopterafrugiperda (Sf9) cells were cultured and used as described by Piwnica-Worms et al., 1990, supra. Sf9 cells were seeded into 60-mm plates (3×10$^6$ cells), allowed to attach, and then were co-infected with baculovirus-mT and baculovirus-pp60$^{c-src}$, or baculovirus-pp60$^{295c-src}$ as described, Piwnica-Worms et al., 1990, supra. Cell pellets were prepared 40 hours post-infection as described below.

Phosphorylation and phosphoamino acid analysis of the phosphatidylinositol 3-kinase Purified PtdIns 3-kinase is a heterodimer of 85 kDa and 110 kDa proteins, Carpenter et al., 1990, supra. The 85 kDa subunit has been shown to be phosphorylated on tyrosine in vivo in mT transformed cells, Kaplan et al., 1987, supra; Carpenter et al., 1990, supra. In order to determine if one or both of the subunits was phosphorylated on tyrosine residues in vitro by mT/pp60$^{c-src}$, protein kinase reactions were performed directly with the immunoprecipitated complex. Protein kinase reactions were performed using immunopurified mT/pp60$^{c-src}$ complex in the presence or absence of purified PtdIns 3-kinase. The protein kinase reaction was initiated with the addition of [λ-$^{32}$P]ATP and stopped after 10 minutes with the addition of 2×gel loading buffer. Polyacrylamide gel electrophoresis (PAGE) of the proteins after the phosphorylation reaction established that both the 110 kDa and 85 kDa polypeptides were phosphorylated. More label was incorporated into the 85 kDa subunit than into the 110 kDa subunit. This result reflects preferential phosphorylation of the 85 kDa subunit as PtdIns 3-kinase purified from rat liver has equi-molar amounts of the 85 kDa and 110 kDa subunits, Carpenter et al., 1990, supra. The purified enzyme has two distinct but homologous 110 kDa subunits with slightly difference mobilities on SDS-PAGE. The upper band of the doublet appeared to be preferentially phosphorylated. [$^{35}$S]-Labelling studies (discussed below) indicated that the difference in phosphorylation between the 85 and 110 kDa subunits is not due to differential immunoprecipitation or release from the immune complex, as similar amounts of metabolically labelled protein remain in the complex. For both the 110 kDa and 85 kDa polypeptides the phosphorylation was saturable and plateaued after 30 minutes. The stoichiometry of phosphorylation was calculated to be 1.2 moles of phosphate per mole of 85 kDa protein added to the assay. The stoichiometry was 0.38 moles of phosphate per mole of 110 kDa protein.

Phosphoamino acid analysis demonstrated that both the 85 kDa and 110 kDa subunits were phosphorylated on tyrosine residues, as expected for phosphorylation by mT/pp60$^{c-src}$.

Complex formation of mT/pp60$^{c-src}$ with phosphatidylinositol 3-kinase from whole cell lysates The immunopurified mT/pp60$^{c-src}$ will also associate with PtdIns 3-kinase from fibroblast lysates. NIH/3T3 or Rat-1 Lysates were prepared from confluent cells in standard lysis buffer as described above. Immunopurified mT/pp60$^{c-src}$ complexes were added to the whole cell lysates and incubated at 4° C. The protein A Sepharose-conjugate mT/pp60$^{c-src}$ complex was then washed with detergent and salt, and assayed for associated phospholipid kinase activity. The resultant samples were extracted and deacylated for analysis by HPLC anion exchange chromatography. PtdIns, PtdIns-4-P, and PtdIns-4,5-P$_2$ kinase activities were present. The HPLC migration positions of the three products were consistent with the structure PtdIns-3-P, PtdIns-3,4-P$_2$, and PtdIns-3,4,5-P$_3$.

Immunopurified mT/pp60$^{295c-src}$ (the kinase inactive mutant) was unable to associate with the endogenous PtdIns 3-kinase activity of fibroblast whole cell lysates as would be expected from the results with purified PtdIns 3-kinase. A small amount of PtdIns4,5-P$_2$ was generated in the immunoprecipitates from both mT/pp60$^{c-src}$ complexes. This is consistent with the results in which some PtdInsP kinase activity was found associated with both of these complexes in the absence of added PtdIns 3-kinase. Thus, the ability of the mT/pp60$^{c-src}$ to associate with PtdIns 3-kinase from whole cell lysates is also dependent on an active protein-tyrosine kinase as demonstrated with the purified enzyme.

The amount of PtdIns 3-kinase activity that associated with the mT/pp60$^{c-src}$ complex was dependent on the amount of lysate in the incubation. Titration of Rat-1 lysates against a fixed amount of mT/pp60$^{c-src}$ complex revealed the immune complex was in excess and lysate from approximately 2.5×10$^6$ cells represented 50% saturation.

Proteins associated with baculovirus expressed mT/pp60$^{c-src}$ from whole cell lysates PtdIns 3-kinase activity was shown to associate with immunopurified baculovirus-expressed mT/pp60$^{c-src}$, but not with the protein-kinase deficient mutant (mT/pp60$^{295c-src}$). To define the specific proteins which associated with the protein-kinase active complex, but which were not seen in the protein-kinase in the protein-kinase deficient complex, NIH/3T3 cells were labelled with Tran$^{35}$S-label and whole cell lysates were prepared.

Immunopurified protein A-conjugated mT/pp60$^{c-src}$ and mT/pp60$^{295c-src}$ were added to separate radiolabelled lysates and incubated at 4° C. for 3 hours. The complexes were washed with NP-40, LiCl, and TNE. The associated proteins were analyzed by SDS-PAGE. Although a number of radiolabelled peptides associate with both the active and inactive protein-kinase complexes, the most striking difference was observed in the 85 KDa and the 110 kDa regions. A band at 153 kDa also preferentially associated with the active mT/pp60$^{c-src}$. These results are analogous to the results obtained with the purified PtdIns 3-kinase, in that both the 110 kDa doublet and the 85 kDa polypeptide associate with the mT/pp60$^{c-src}$ complex in vitro.

Peptides that block the association of PtdIns 3-kinase with the mT/pp60$^{c-src}$ complex Data presented herein demonstrates that tyrosine kinase activity in the mT/pp60$^{c-src}$ complex is required for association of PtdIns 3-kinase. The major site of tyrosine phosphorylation on mT by pp60$^{c-src}$ is tyrosine 315. Amino acid sequence in this region of the peptide is conserved in various protein-tyrosine kinases that have been observed to associate with PtdIns 3-kinase, Cantley et al., 1991, supra. To further characterize the in vitro association and directly test the importance of phosphorylation of this sequence, competition experiments with a phosphorylated and unphosphorylated version of a synthetic 12 amino acid peptide based on the region of hamster mT that is homologous to murine mT around tyrosine 315 (see Table 2) were performed.

Pre-incubation of the phosphorylated peptide with whole cell lysates blocked association with the immunopurified mT/pp60$^{c-src}$ complex. Pre-incubation of the unphosphorylated version of the peptide with cell lysates did not affect the association. The phosphorylated version of the peptide could also block the association of PtdIns 3-kinase activity with the immunopurified mT/pp60$^{c-src}$ when purified PtdIns 3-kinase was used for the association assay.

Proteins that were prevented from associating with the mT/pp60$^{c-src}$ complex by the phosphorylated peptide were also determined. Whole cell lysates from Tran$^{35}$S-labelled (as shown by gel electrophoresis experiments) Rat-1 cells were pre-incubated with phosphorylated peptide, unphosphorylated peptide, or no peptide, and then association with exogenously added mT/pp60$^{c-src}$ was done as described in materials and methods. Gel electrophoresis experiments showed that bands consistent with PtdIns 3-kinase (a doublet around 110 kDa and an 85 kDa band) associate with the kinase active complex but not with the protein kinase deficient mT/pp60$^{295c-src}$. The unphosphorylated peptide did not affect this association. However, the phosphorylated peptide specifically blocked three proteins from associating with the kinase active mT/pp60$^{c-src}$ complex. Other, higher molecular weight proteins that associated in a protein kinase dependent manner were not blocked by the phosphorylated peptide.

Inhibition of SH2 Domain-Phosphoprotein Association By A Nonhydrolyzable Phosphonopeptide The association between the pp60$^{c-src}$/polyoma virus middle T antigen (mT) complex and phosphatidylinositol 3-kinase (PI 3-kinase) can be used as a prototype for phosphoprotein-SH2 domain interactions. It can be used to test whether a peptide, e.g., a non-hydrolyzable phosphonopeptide, can inhibit the association between an SH2 domain containing protein and a YMXM (SEQ ID NO: 20) containing protein. As discussed above, phosphonomethylphenylalanine (Pmp) is a non-natural analogue of phosphotyrosine in which the >C—O—PO$_3$H$_2$ moiety is replaced by >C—CH$_2$—PO$_3$H$_2$. A thirteen amino acid phosphonopeptide (mT-Pmp315), a related phosphopeptide (mT-pY315) and an unmodified sequence (mT-Y315) all corresponding to the pp60$^{c\text{-}src}$-phosphorylated site of the mT which is within a YMXM (SEQ ID NO: 20) motif common to proteins that bind to and activate PI 3-kinase where synthesized. As is discussed below, only the phosphonopeptide persistently blocked the in vitro association of baculovirus-expressed pp60$^{c\text{-}src}$/mT complex with cytosolic PI 3-kinase activity. Sustained inhibition of association by the phosphopeptide required the additional presence of vanadate, a potent protein tyrosine phosphatase (PTPase) inhibitor. The phosphopeptide and L-phosphonopeptide bound tightly ($K_D \cong 10$–20 nM) and specifically to isolated SH2 domains of PI 3-kinase p85, demonstrating that the mechanism of inhibited association is competitive binding to PI 3-kinase SH2 domains. Thus, the appropriate phosphonopeptide sequence inhibits the interaction between a tyrosinephosphorylated protein and a cognate SH2 domain-containing protein, and is resistant to the actions of PTPases. Proteolytically stable phosphonopeptide derivatives are useful inhibitors of protein-protein interactions when introduced into cells, and provide a basis for the rational design of a new class of chemotherapeutic agent.

By incorporating a non-hydrolyzable analogue of phosphotyrosine within the same peptide sequences a new class of peptides which retain the capacity to bind to p85 SH2 domains and, in addition, which are resistant to the actions of cellular PTPases was generated. Three peptides having the same linear sequence corresponding to residues surrounding Tyr315 of the mouse polyoma virus middle T antigen (mT) were synthesized. The sequence of the peptides is H-Glu-Glu-Glu-Xxx-Met-Pro-Met-Glu-Asp-Leu-Tyr-OH, (SEQ ID NO: 43) wherein Xxx is the targeted tyrosine residue and is substituted at the para position with any of a free hydroxyl, a phosphate or the non-hydrolyzable, methylene-bridged phosphonate. Both the phosphopeptide and the phosphonopeptide were found to bind to isolated SH2 domains of the P85 subunit of PI 3-kinase. However, the in the absence of PTPase inhibitors only the phosphonopeptide inhibited pp60$^{c\text{-}src}$/mT complex association with cytosolic PI 3-kinase activity.

Peptide Synthesis was performed as follows. Syntheses of peptides E-E-E-X-M-P-M-E-D-L-Y (SEQ ID NO: 43), where X=Pmp, phosphotyrosine or tyrosine, were conducted on a Milligen/Biosearch 9600 synthesizer using 4-alkoxybenzyl alcohol polystyrene resin (PAC, Milligen/Biosearch). The N$^\alpha$-Fmoc protecting group was used throughout in conjunction with t-butyl group side chain protection of Asp, Glu and Tyr. Racemic N$^\alpha$-Fmoc-(O,O-di-t-butyl)phosphono-p-methylphenylalanine (Fmoc-Pmp (tBu)$_2$—OH) (see Shoelson et al, 1991, *Tetrahedron Lett.* 32:6061–6064; see Burke et al., 1991, *Synthesis* 11:1019–1020) and N$^\alpha$-Fmoc-O-(O,O-dimethoxyphosphoryl)-L-tyrosine (Fmoc-Tyr(OP(OCH$_3$)$_2$) (Kitas et al., 1991, *Helv. Chim. Acta* 74:1314–1328) were used as protected synthons for incorporation of Pmp and phosphotyrosine, respectively. Peptide bond-forming reactions with 0.2M N$^\alpha$-Fmoc amino acid, 1-hydroxybenzotriazole (HOB$_t$) and benzotriazoyloxy tris-(dimethylamino)phosphonium hexafluorophosphate (BOP) were conducted for 1 h prior to incorporation of Fmoc-Pmp (tBu)$_2$—OH or Fmoc-Tyr(OP(OCH$_3$)$_2$ were coupled manually with a two-fold excess of Fmoc-amino acid, HOBT and BOP. Peptides were cleaved from the resin and side chain protecting groups were simultaneously removed by treatment with trifluoroacetic acid, thioanisole, ethanedithiol and anisole (90:5:3:2) for 2 h at 22° C. Methyl protecting groups on phosphotyrosine were removed during a second stage of deprotection with trimethylsilyl bromide (Kitas et al., 1991, *Helv. Chim. Acta* 74:1314–1328). All peptides were precipitated with diethyl ether (4° C.) and desalted on a column of Bio-gel P2. Peptides were further purified and D- and L-forms of the Pmp peptides were separated using a Waters' Prep 4000 HPLC equipped with a Dynamax-300A 12 μm C8 column (41.4×250 mm). Amino acid analyses (ABI 420) and results obtained from plasma desorption mass spectrometry (ABI Biolon) were as expected (Shoelson et al., 1991, *Tetrahedron Lett.* 32:6061–6064).

Inhibition of the in vitro Association of PI 3-Kinase Activity With Immunopurified pp60$^{c\text{-}src}$/mT. Baculovirus-expressed pp60$^{c\text{-}src}$/mT complex was immunopurified from infection Sf9 insect cell (Piwnica-Worms et al., 1990, J. Virol. 64:61–68) lysates as described (Auger et al., 1990, 1992, J. Biol. Chem. 267:5408–5415). PI 3-kinase activity was obtained directly from crude Balb/3T3 cell lysates as follows. After washing confluent 10 cm dishes with phosphate-buffered saline, Balb/3T3 cells were treated with lysis buffer (137 mM NaCl, 20 mM Hepes, 1 mM MgCl$_2$, 1 mM CaCl$_2$, 10% glycerol, 1% Nonidet P-40, and 1 μg/ml each of leupeptin, pepstatin A and aprotinin, pH 7.25) in the presence or absence of 0.15 mM sodium vanadate. Following a 10 min incubation with lysis buffer, cells were scrape-harvested and particulate debris was removed from the lysates by centrifugation at 12,000×g for 5 min. at 4° C. Varying concentrations of peptides were added directly to the lysates and incubated at 4° C. for 30 min.

Lysate-peptide mixtures were combined with protein A-Sepharose beads containing immunoprecipitated pp60$^{c\text{-}src}$/mT complexes. After washing, the beads were used to catalyze phosphatidylinositol phosphorylation as described (Whitman et al., 1985, *Nature* 315:239–242; Auger et al., 1989, *Cell* 57:167–175, 1990, *Methods in Inositide Res*. pp. 159–166). Sonicated phospholipids were added to the beads and phosphorylation reactions were initiated with 50 μM [λ-$^{32}$P]ATP, 5 mM MgCl$_2$ in 20 mM HEPES, pH 7.5. Following 5 min incubations at 22° C. the 50 μl reactions were terminated by addition of 80 μl of 1N HCl and 1 μl of 0.5 mM ethylenediamine tetra acetic acid. Lipids were extracted with 0.16 ml of methanol/chloroform (1:1) and separated by thin layer chromatography (Auger et al., 1990, *Methods in Inositide Res*. pp. 159–166).

Peptide Binding to Isolated Glutathione S-Transferase/SH2 Domain Fusion Proteins was determined as follows. N-terminal p85 SH2/GST fusion proteins (100 nM) (Hu et al., 1992, *Mol. Cell. Biol.* 12:981–990), 35 fmol of HPLC-purified, [$^{125}$I]Bolton-Hunter-treated phosphopeptide (67 nCi) and varying concentrations of unlabeled peptides were combined in 200 μl total volume of 20 mM tris-HCl, 250 mM NaCl, 0.1% bovine serum albumin, 10 mM dithiothreitol, pH 7.4. Glutathione-agarose (25 μl of a 1:4 aqueous slurry, Molecular Probes) was added and the samples were incubated at 22° C. for 4 h. Following centrifugation for 5 min at 12,000×g, supernatant solutions were removed by aspiration and [$^{125}$I]radioactivity associated with the pellets was determined with a λ-counter.

Amino Acid Side Chain pK was determined as follows. Phosphonomethylphenylalanine and phosphotyrosine were suspended in water and brought into solution by addition of sodium hydroxide to yield an 0.2M solution, pH>10.3. Aliquots (10 μl) of 6N HCl were added with mixing and the pH was recorded.

Inhibition of PI 3-kinase association with the pp60$^{c\text{-}src}$/mT complex was determined as follows. Cytosolic PI 3-kinase activity associates with pp60$^{c\text{-}src}$/mT complexes and can be immunoprecipitated with antibodies against either pp60$^{c\text{-}src}$ or mT. This association occurs only if the pp60$^{c-src}$ is an active protein tyrosine kinase, suggesting that a key feature of the recognition involves tyrosine phosphorylation. Furthermore, the association can be blocked by a phosphopeptide corresponding to the sequence surrounding Ty298 of hamsterpolyomamT(Auger et al., 1992, *J. Biol. Chem.* 267:5408–5415).

A phosphopeptide and matched non-hydrolyzable phosphonopeptide corresponding to the sequence surrounding Tyr315 of mouse polyoma mT were prepared as described herein. In the presence of 200 μM sodium vanadate both peptides inhibited association between pp60$^{c-src}$/mT and PI 3-kinase, with ID$_{50}$ values of ≈100 nM and ≈800 nM for the phosphopeptide and racemic phosphonopeptide, respectively. (For the determination of concentration dependencies for inhibition of the association between baculovirus-expressed mT/pp60$^{c-src}$ complex and cytosolic PI 3-kinase activity by phosphopeptide mT-pY315 and racemic phosphonopeptide mT-Pmp315 peptides were incubated with cytosol from Balb/3T3 cells in the presence of 200 μM sodium vanadate and combined with baculovirus-expressed mT/pp60 $^{src}$ complex, anti-mT antibodies and protein A-Sepharose. Precipitated protein complexes were used to catalyze phosphorylation of phosphatidylinositol as described herein.) An unphosphorylated peptide having the same hamster mT sequence had no detectable activity under these conditions (Auger et al., 1992, *J Biol. Chem.* 267:5408–5415).

Similar experiments were conducted in the absence of sodium vanadate to determine whether inhibition would persist in the presence of active protein tyrosine phosphatases (PTPases). Concentrations of peptides were chosen to give ≈50% inhibition of association between pp60$^{c-src}$/mT and PI 3-kinase activity. (To determine phosphopeptide vs. phosphonopeptide inhibition of association between baculovirus-expressed mT/pp60$^{src}$ complex and cytosolic PI 3-kinase activity in the presence and absence of sodium vanadate peptides were incubated first with cytosol from Balb/3T3 cells at 4° C. for 30 min in the presence and absence of 200 μM sodium vanadate, were combined with baculovirus-expressed mT/pp60$^{src}$ complex, anti-mT antibodies and protein A-Sepharose for an additional 2 h; peptide concentrations were chosen to inhibit ≈one-half of associated PI 3-kinase activity (e.g., 75–100 nM mT-pY315; 0.75–1.0 μM mT-Pmp315). Following washes, precipitated proteins were used to catalyze phosphorylation of phosphatidylinositol as described herein.) (Chatterjee et al., 1992, *Peptides: Chemistry and Biology* pp. 553–555) Phosphopeptide-mediated inhibition of association was obliterated in the absence of vanadate due to tyrosine dephosphorylation. By contrast, inhibition by the phosphonopeptide persisted even in the absence of PTPase inhibition, which demonstrates the inability of PTPases to hydrolyze the C-P bond of Pmp. In fact, Pmp is unaltered by prolonged incubation with high concentrations of expressed PTPases and is stable under much harsher hydrolytic conditions (e.g., boiling 6.0N HCl for 18 h; Marseigne & Roques, 1988, *J Org. Chem.* 53:3621).

Phosphopeptide and phosphonopeptide binding to p85 SH2 domains. To investigate the mechanism of phosphonopeptide inhibition of association direct binding to an isolated SH2 domain of the p85 of PI 3-kinase was analyzed. In the assay, tracer amounts of [$^{125}$I]-labeled phosphopeptide, SH2 domain/GST fusion protein, and varying concentrations of unlabeled peptides were incubated together along with glutathione-agarose. In the absence of unlabeled phosphopeptide 15–30% of total added radioactivity was precipitated specifically with the glutathione beads; in the presence of excess phosphopeptide or in the absence of SH2/GST fusion protein 2–5% of total radioactivity was found to associate (nonspecifically) with the glutathione beads. ID$_{50}$ values were determined as the concentration of unlabeled peptide required to inhibit 50% of specific [$^{125}$I]phosphopeptide binding. Binding data were best-fit to the sigmoid dose-response equation y=((a)/(1+e$^{(x-c)}$))+d as described (DeLean et al., 1978, *Am. J Physiol.* 235:E97–102). A calculated ID$_{50}$ value for the phosphopeptide mT-pY315 was 3.6 μM. (Competition of binding between peptides and p85 SH2/GST fusion protein was determined as follows. N-terminal p85 SH2/GST fusion protein, [$^{125}$I]phosphopeptide and varying concentrations of unlabeled peptides were combined in 200 μl total volume of 20 mM Tris-HCl, 250 mM NaCl, 0.1% bovine serum albumin, 10 mM dithiothreitol, pH 7.4. Glutathione-agarose (25 μl of a 1:8 aqueous slurry) was added and the samples were incubated at 22° C. for 4 h. Following centrifugation for 5 min at 12,000×g, supernatant solutions were removed by aspiration and [$^{125}$I]radioactivity associated with the pellets was determined with a λ-counter.)

Different affinities were observed for the two isomers of the phosphonopeptide: ID$_{50}$ values for the L- and D-isomers were 7.2 μM and 131 μM, respectively. Therefore, L-mT-Pmp315 binds to the N-terminal SH2 domain of p85 2-fold weaker than the corresponding phosphopeptide (which contains L-phosphotyrosine), whereas D-mT-Pmp315 binds to the N-terminal SH2 of p85 much more weakly with a relative ID$_{50}$ value≈30- to 40-fold higher than the phosphopeptide. As the D- and L-forms of the phosphonopeptide were separated by HPLC and eluted closely together (Shoelson et al., 1991, *Tetrahedron Lett.* 32:6061–6064), traces of the opposite isomer might contaminate the HPLC-separated isomers. Therefore, D-mT-Pmp315 could bind with even weaker relative affinity. The non-phosphorylated peptide mT-Y315 exhibited no binding.

Whereas accurate relative affinities can be obtained from the competition assay, accurate absolute values for K$_D$ are not obtained due, in part, to the high concentration of SH2 domain/GST fusion protein compared to K$_D$ (Piccione et al, manuscript in preparation).

Therefore, mT-pY315 binding to p85 SH2 domains was analyzed using biospecific interaction analysis as previously described to obtain a more accurate estimate for K$_D$. Series of data were obtained during real-time binding experiments with different concentrations of SH2/GST fusion protein (data not shown). The data, extrapolated to infinite time to estimate values for "steady-state" binding, were analyzed as bound/free vs. bound analogous to a Scatchard plot to obtain an estimated K$_D$ of 10 nM. By comparison, estimated K$_D$ values for L- and D-mT-Pmp315 are 20 nM and ≧0.3–0.4 μM, respectively.

Phosphonate vs. phosphate pK. To assess possible reasons for reduced affinity of the phosphonopeptide vs. the phosphopeptide side chain pK$_a$ values were determined. For phosphotyrosine pK$_3$ (—OPO$_3$H←→—OPO$_3$H$_2$) was 5.7, in close agreement with a reported value (Cooper et al., 1983, *Met. in Enzymol.* 99:387–402). The corresponding pK$_3$ value for Pmp was 7.1. Therefore, at neutral pH the phosphate side chain of phosphotyrosine is mostly charged whereas the phosphonate side chain of Pmp is approximately one-half charged, which may explain the different affinities observed for the phosphopeptide vs. the L-phosphonopeptide.

Inhibition of protein tyrosine kinases

Peptide Synthesis Phosphopeptides were synthesized by solid-phase methods known to those skilled in the art (DIPCDI/HOBt couplings in DMF) using Fmoc-pTyr with an unprotected phosphate side chain. In many cases the desired products were obtained as single major products, particularly when pTyr was incorporated toward the amino-terminus of the peptide. PTPase inhibitors were synthesized by similar methods with Fmoc-Pmp, see Marseigne et al., 1988, J. Org. Chem. 53:3621–3624, hereby incorporated by reference. Phosphopeptides and phosphonopeptides were readily purified by HPLC, and gave the expected amino acid composition and FAB-MS values.

PTPase Substrates The major phosphorylation sites of the insulin receptor(IR), PDGF receptor (PDGF-F), pp60$^{c-src}$, the polyoma virus transforming protein, middle t, and putative phosphorylation sites of the endogenous insulin receptor substrate (IRS-1) were synthesized as phosphotyrosine peptides. Most of these sequences have only one Tyr residue. However, activation of the insulin receptor requires phosphorylation of three proximate Tyr residues (White et al., 1988, J.Biol. Chem. 263:2969) and all three monophosphopeptides were prepared.

The phosphopeptides were used as substrates of PTPase 1B, a single catalytic domain PTPase with a side tissue distribution (Hunter et al., 1989, cell 58:1013). Rat PTPase 1B (Guan et al., 1990, Proc. Natl., Acad. Sci. USA 87:1501) was obtained by PCR and cloning the full-length cDNA into the bacterial expression vector, PKK233-2.

Sequence specificity for peptide dephosphorylation was observed, with apparent Km values ranging from <2 µM for the phospho-middle t sequence to >2 mM for pTyr itself (Table 3). $K_m$ values are lower and specificity different than that observed with similar peptides and LAR (leukocyte antigen-related PTPase), suggesting that substrate "fingerprinting" might be useful for categorizing PTPases within families. Notably, with PTPase 1B the three insulin receptor monophosphosiptides exhibited similar $K_m$ values in the 30 µM range, in contrast to results with LAR where regiospecificity was observed.

rated into two components by HPLC which corresponded to peptides having D- and L-Pmp, respectively.

Several phosphono peptides were tested for the ability to inhibit PTPase 1B activity and $K_I$ values determined by methods known to those skilled in the art. Peptides containing L-pTyr and L-Pmp had similar affinities for PTPase 1B, suggesting that our inhibitor design strategy is appropriate (Table 3). Interestingly, the D-Pmp insulin receptor sequence had similar affinity for PTPase 1B. A related peptide, prepared with all three Tyr residues substituted with Pmp showed over a 15-fold increased affinity (with 3 chiral centers this was a mixture of nine unresolved optical isomers).

Inhibitor Assays The activity of a peptide inhibitor can be assayed by determining the ability of the inhibitor to inhibit the dephosphorylation of a naturally occurring or synthetic substrate. These assays can be performed in cultured cells or in cell free systems e.g., by adding an inhibitor and following the phosphorylation of a predetermined component. Alternatively, purified or partially purified components can be tested in vitro to determine the ability of an inhibitor to inhibit dephosphorylation by a specific PTPase, e.g., placental PTPase, Tonks et al., 1988 J. Biol. Chem 263:6731, CD45, Tonks et al., 1988, Biochem. 27:8696, LAR, Streuli et al., 1988, S. Exp. Med. 168:1523, or human T cell PTPase, Cool et al., 1989, Proc. Natl. Acad. Sci USA 86:5257. The substrate tested can be a naturally occurring substrate or a synthetic substrate.

Hydrolysis Resistant Phosphotyrosine Analogs with Enhanced Binding Affinities

Increasing the electronegativity of the phosphate moiety in an analog of phosphotyrosine increases the binding affinity of peptides containing the analog to a substrate such as protein containing an $SH_2$ domain, and in some cases can exceed that of peptides containing phosphotyrosine.

The electronegativity of the phosphate moiety can be increased by substituting the hydrogens on the carbon

TABLE 3

Sequences and Potencies of PTPase Substrates and Inhibitors

| Name | Sequence/Structure | $K_m$ or $K_i$ (µM) |
|---|---|---|
| Phosphotyrosine & pY-peptides | | |
| IR1155-1165(pY1158) | RDIpYETDYYRK (SEQ ID NO: 9) | 30 |
| IR1155-1165(pY1162) | RDIYETDpYYRK (SEQ ID NO: 10) | 40 |
| IR1155-1165(pY1163) | RDIYETDYpYRK (SEQ ID NO: 11) | 30 |
| pp60$^{c-src}$(pYS27) | TEPEpYQPGE (SEQ ID NO: 12) | 8 |
| mPDGF-Rβ(pY719) | KDESIDpYVPMLDMKGD (SEQ ID NO: 13) | 8 |
| middle t(pY298) | RENEpYMPMAPQIH (SEQ ID NO: 14) | <2 |
| IRS-1(pY608) | TDDGpYMPMSPGV (SEQ ID NO: 15) | 30 |
| IRS-1(pY628) | GNGDpYMPMSPKS (SEQ ID NO: 16) | 100 |
| phosphotyrosine | $NH_2CH(CO_2H)CH_2C_6H_4OPO_3H_2$ | >2,000 |
| Phosphonomethylphenylalanine & Pmp-peptides | | |
| IR1155-1165(L-Pmp1158) | RDI[L-Pmp]ETDYYRK (SEQ ID NO: 9) | 30 |
| IR1155-1165(d-Pmp1158) | RDI[D-Pmp]ETDYYRK | 30 |
| IR1155-1165(D,L-Pmp3) | RDIPmpETDPmpPmpRK (SEQ ID NO: 42) | <2 |
| Pmp | $NH_2CH(CO_2H)CH_2C_6H_4CH_2PO_3H_2$ | >500 |

A = Ala; R = Arg; N-Asn; D = Asp; C = Cys; Q = Gln; E = Glu; G = Gly; I = Ile; L = Leu; K = Lys; M = Met; F = Phe; P = Pro; S = Ser; T = Thr; Y = Tyr; V = Val.

PTPase Inhibitors Representative phosphopeptide substrate sequences were prepared as phosphonopeptides for use as inhibitors. Pmp was synthesized chemically as a racemic mixture which was not resolved prior to peptide synthesis. Synthetic products were, however, readily separated into two components by HPLC which corresponded to peptides having D- and L-Pmp, respectively.

between the phenyl ring and the phosphonate group with small, electronegative atoms such as fluorine or chlorine. Fluorine atoms are particularly desirable because they increase the electronegativity of the phosphate moiety without significantly adding to the bulk of the molecule.

Hydrolysis resistant phosphotyrosine analogs such as monofluorophosphonomethylphenylalanine and difluorophosphonomethylphenylalanine can be used in peptides and methods of the invention, e.g., in place of Pmp.

Those of ordinary skill in the art will be able to synthesize difluorophosphonomethylphenylalanine using methods known in the art.

The increased affinity of fluorinated analogs was shown in studies which examined the binding of various analogs to the SH2 domains of P13-kinase P85, Src and Grb2, PLC-γ, Syp/SHPTP2, Shc, and Lck. In these experiments, one or both hydrogen atoms were replaced on Pmp at the carbon position between the phenyl ring and the phosphonate.

Phosphotyrosine or its analogs were inserted in a peptide and the binding ability of the analog peptides was compared to that of phosphotyrosine. FIG. 2 shows the results of this study. In FIG. 2, phosphotyrosineis indicated by filled squares (■). Phosphotyrosine (■) was replaced in the peptide by Pmp (□), monofluorophosphonomethylphenylalanine (FPmp) (◇), $F_2$Pmp (star), hydroxyfluorophosphonomethylphenylalanine (HPmp) (○), and tyrosine (Tyr) (♦). The $ED_{50}$ values were 0.17±0.02 μM for pTyr, 1.0±0.1 μM for Pmp, 0.50±0.03 μM for FPmp, 0.17±0.02 μM for $F_2$Pmp, 3.3±0.5 μM for HPmp, and >1,000 μM for Tyr. The $Ed_{50}$ of $F_2$Pmp matched that of phosphotyrosine while FPmp, Pmp, HPmp, and tyrosine each had higher $ED_{50}$ values. As fluorines were added to the carbon between the phenyl ring and the phosphonate the $ED_{50}$ of the analog decreased from 1.0 μM(Pmp) to 0.5 μM(FPmp) to 0.17 μM($F_2$Pmp) indicating that as the electronegativity of the phosphonate moiety increases, the binding affinity of the phosphopeptide increases.

FIG. 3 is a depiction of: panel A, the binding affinity of the peptide DXVPML (SEQ ID NO:46) for the $SH_2$ domain of PI 3-kinase where X was pTyr (●) or $F_2$Pmp (○), the $ED_{50}$ values were 0.15±0.03 μM pTyr and 0.17±0.02 μM for $F_2$Pmp; panel B, the binding affinity of the peptide QXEEIP (SEQ ID NO:47) for the $SH_2$ domain of Src where X was pTyr (●) or $F_2$Pmp (○), the $ED_{50}$ values were 5.7±0.7 μM for pTyr and 1.0±0.2 μM for $F_2$Pmp; panel C, the binding affinity of the peptide NXVNIE (SEQ ID NO: 48) for the $SH_2$ region of Grb2 where X was pTyr (●), L-$F_2$Pmp(○), or D-$F_2$Pmp(□), the $ED_{50}$ values were 0.9±0 μM for pTyr, 4.7±0.7 μM for L-$F_2$Pmp, and >300 μM for D-$F_2$Pmp. FIG. 3 indicates that in some cases $F_2$Pmp can bind more potently to the $SH_2$ domain of a protein than phosphotyrosine. Panel B of FIG. 3 shows that Ac-Q-$F_2$Pmp-E-E-I-P-$NH_2$ (SEQ ID NO: 47) binds more avidly to the $SH_2$ domain of Src than phosphotyrosine.

In addition, $F_2$Pmp peptides have been microinjected into living cells and have been effective in inhibiting ligand-stimulated effects.

Use

The peptides of the invention may be administered to a mammal, particularly a human, on any suitable fashion, e.g., in one of the traditional modes (e.g., orally, parenterally, transdermally, or transmucosally), in a sustained release formulation using a biodegradable biocompatible polymer, or by on-site delivery using micelles, gels and liposomes.

Dosages will vary, depending on factors such as, the disease being treated, the half life of the substance, potency, route of administration, and the condition of the patient.

Other embodiments are within the following claims.

---

What is claimed is:

1. A method of inhibiting a site specific interaction between a first molecule which comprises an SH2 domain and a second molecule which inters with said SH2 domain comprising contacting said first molecule with an inhibitor molecule which comprises a peptide comprising the sequence $R^1$-$R^2$-$R^3$-$R^4$ wherein:

$R^1$, phosphotyrosine, or an analog of phosphotyrosine having a hydrolysis resistant phosphorous moiety;

$R^2$ is Met;

$R^3$ is any amino acid;

$R^4$ is Met; and wherein said peptide is between 4 and 30 amino acid residues in length.

2. The method of claim 1, wherein $R^1$ is a phosphonomethylphenylalanine residue or a mono or difluorophosphonomethylphenylalanine residue.

3. The method of claim 1, wherein said first molecule is a transmembrane protein.

4. The method of claim 1, wherein said first molecule is an oncogene protein.

5. The method of claim 1, wherein said second molecule is an enzyme which can alter the degree of phosphorylation of a tyrosine.

6. The method of claim 1, wherein said peptide has an $ED_{50}$ or $IC_{50}$ of less than 100 µM for inhibiting binding of the second molecule to an SH2 domain containing protein.

7. The method of claim 6, wherein said peptide is a fragment of the platelet-derived growth factor receptor which contains a phosphotyrosine residue or an analog of phosphotyrosine having a hydrolysis resistant phosphorous moiety.

8. The method of claim 7, wherein the Tyr is chosen from the group of Tyr740.

9. The method of claim 6, wherein said peptide is a fragment of the epidermal growth factor receptor which contains a phosphotyrosine residue or an analog of phosphotyrosine having a hydrolysis resistant phosphorous moiety.

10. The method of claim 9, wherein the Tyr is chosen from the group of Tyr920.

11. The method of claim 6, wherein said peptide is a fragment of the Insulin Receptor Substrate-1 which contains a phosphotyrosine residue or an analog of phosphotyrosine having a hydrolysis resistant phosphorous moiety.

12. The method of claim 6, wherein said peptide is a fragment of the middle T protein which contains a phosphotyrosine residue or an analog of phosphotyrosine having a hydrolysis resistant phosphorous moiety.

13. The method of claim 6, wherein said peptide is a fragment CD 28 which contains a phosphotyrosine residue or an analog of phosphotyrosine having a hydrolysis resistant phosphorous moiety.

14. The method of claim 6, wherein the Tyr is Tyr191.

15. The method of claim 6, wherein the pTyr of said peptide is replaced with an analog of phosphotyrosine having a hydrolysis resistant phosphorous moiety.

16. A method of inhibiting a site specific interaction between a first molecule which comprises an SH2 domain and a second molecule which interacts with said SH2 domain comprising contacting said first molecule with an inhibitor molecule which comprises a peptide which has an $ED_{50}$ or $IC_{50}$ of less than 100 µM for inhibiting binding of the second molecule to an SH2 domain containing protein or fragment thereof and which is one of the following peptides:

D-D-G-pY-M-P-M-S-P-G-V (SEQ ID NO:52); G-N-G-D-pY-M-P-M-S-P-K-S (SEQ ID NO:53); P-N-G-pY-M-M-M-S-P-S-G (SEQ ID NO:54); T-G-D-pY-M-N-M-S-P-V-G (SEQ ID NO:55); S-E-E-pY-M-N-M-D-L-P-G (SEQ ID NO:57); R-D-G-pY-M-T-M-Q-I-G (SEQ ID NO:58); I-D-V-pY-M-I-M-V-K (SEQ ID NO:68); D-G-G-pY-M-D-M-S-K-D-E (SEQ ID NO:80); H-S-D-pY-M-N-M-T-P-R (SEQ ID NO:112); Asn-Gly-Asp-pTyr-Met-Prm-Met-Ser-Pro-Lys-Ser-OH (SEQ ID NO:196); Gly-Asp-pTyr-Met-Pro-Met-Ser-Pro-Lys-Ser-OH (SEQ ID NO:197); Ac-Asp-pTyr-Met-Pro-Met-Ser-Pro-Lys-Ser-OH (SEQ ID NO:198); Asp-pTyr-Met-Pro-Met-Ser-Pro-Lys-Ser-OH (SEQ ID NO:199); Ac-pTyr-Met-Pro-Met-Ser-Pro-Lys-Ser-OH (SEQ ID NO:200); pTyr-Met-Pro-Met-Ser-Pro-Lys-Ser-OH (SEQ ID NO:201); Ac-pTyr-Met-Pro-Mer-Ser-Pro-NH$_2$ (SEQ ID NO:202); Ac-pTyr-Met-Pro-Met-Ser-NH$_2$ (SEQ ID NO:203); Ac-pTyr-Met-Pro-Met-NH$_2$ (SEQ ID NO:204); Ac-pTyr-Met-Pro-Met-Ser-Pro-Lys-Ser-OH (SEQ ID NO:205); Ac-pTyr-Met-Pro-Met-Ser-Pro-Ala-Ser-OH (SEQ ID NO:206); Ac-pTyr-Met-Pro-Met-Ser-Ala-Lys-Ser-OH (SEQ ID NO:207); Ac-pTyr-Met-Pro-Met-Ala-Pro-Lys-Ser-OH (SEQ ID NO:208); Ac-pTyr-Met-Ala-Met-Ser-Pro-Lys-Ser-OH (SEQ ID NO:209).

\* \* \* \* \*

SEQUENCE LISTING ( 1 ) GENERAL INFORMATION:

( i i i ) NUMBER OF SEQUENCES: 211

( 2 ) INFORMATION FOR SEQ ID NO:1:

( i ) SEQUENCE CHARACTERISTICS:
        ( A ) LENGTH: 4
        ( B ) TYPE: amino acid
        ( C ) STRANDEDNESS: single
        ( D ) TOPOLOGY: linear ( x i ) SEQUENCE DESCRIPTION: SEQ ID NO:1:

Tyr Xaa Xaa Met
 1

( 2 ) INFORMATION FOR SEQ ID NO:2:

( i ) SEQUENCE CHARACTERISTICS:
        ( A ) LENGTH: 4
        ( B ) TYPE: amino acid
        ( C ) STRANDEDNESS: single
        ( D ) TOPOLOGY: linear ( x i ) SEQUENCE DESCRIPTION: SEQ ID NO:2:

Tyr Xaa Xaa Xaa
 1

( 2 ) INFORMATION FOR SEQ ID NO:3:

( i ) SEQUENCE CHARACTERISTICS:

( A ) LENGTH: 4
            ( B ) TYPE: amino acid
            ( C ) STRANDEDNESS: single
            ( D ) TOPOLOGY: linear ( x i ) SEQUENCE DESCRIPTION: SEQ ID NO:3:

Tyr Glu Glu Ile
1

( 2 ) INFORMATION FOR SEQ ID NO:4:

( i ) SEQUENCE CHARACTERISTICS:
            ( A ) LENGTH: 4
            ( B ) TYPE: amino acid
            ( C ) STRANDEDNESS: single
            ( D ) TOPOLOGY: linear ( x i ) SEQUENCE DESCRIPTION: SEQ ID NO:4:

Xaa Xaa Xaa Xaa
1

( 2 ) INFORMATION FOR SEQ ID NO:5:

( i ) SEQUENCE CHARACTERISTICS:
            ( A ) LENGTH: 4
            ( B ) TYPE: amino acid
            ( C ) STRANDEDNESS: single
            ( D ) TOPOLOGY: linear ( x i ) SEQUENCE DESCRIPTION: SEQ ID NO:5:

Xaa Xaa Xaa Met
1

( 2 ) INFORMATION FOR SEQ ID NO:6:

( i ) SEQUENCE CHARACTERISTICS:
            ( A ) LENGTH: 4
            ( B ) TYPE: amino acid
            ( C ) STRANDEDNESS: single
            ( D ) TOPOLOGY: linear ( x i ) SEQUENCE DESCRIPTION: SEQ ID NO:6:

Xaa Met Xaa Met
1

( 2 ) INFORMATION FOR SEQ ID NO:7:

( i ) SEQUENCE CHARACTERISTICS:
            ( A ) LENGTH: 4
            ( B ) TYPE: amino acid
            ( C ) STRANDEDNESS: single
            ( D ) TOPOLOGY: linear ( x i ) SEQUENCE DESCRIPTION: SEQ ID NO:7:

Xaa Glu Glu Ile
1

( 2 ) INFORMATION FOR SEQ ID NO:8:

( i ) SEQUENCE CHARACTERISTICS:
            ( A ) LENGTH: 4
            ( B ) TYPE: amino acid
            ( C ) STRANDEDNESS: single
            ( D ) TOPOLOGY: linear ( x i ) SEQUENCE DESCRIPTION: SEQ ID NO:8:

Tyr Met Xaa Met
1

( 2 ) INFORMATION FOR SEQ ID NO:9:

( i ) SEQUENCE CHARACTERISTICS:
        ( A ) LENGTH: 13
        ( B ) TYPE: amino acid
        ( C ) STRANDEDNESS: single
        ( D ) TOPOLOGY: linear ( x i ) SEQUENCE DESCRIPTION: SEQ ID NO:9:

```
Arg  Asp  Ile  Xaa  Met  Pro  Glu  Thr  Asp  Tyr  Tyr  Arg  Lys
 1              5                        10
```

( 2 ) INFORMATION FOR SEQ ID NO:10:

( i ) SEQUENCE CHARACTERISTICS:
        ( A ) LENGTH: 13
        ( B ) TYPE: amino acid
        ( C ) STRANDEDNESS: single
        ( D ) TOPOLOGY: linear ( x i ) SEQUENCE DESCRIPTION: SEQ ID NO:10:

```
Arg  Asp  Ile  Tyr  Glu  Thr  Asp  Pro  Met  Xaa  Tyr  Arg  Lys
 1              5                        10
```

( 2 ) INFORMATION FOR SEQ ID NO:11:

( i ) SEQUENCE CHARACTERISTICS:
        ( A ) LENGTH: 13
        ( B ) TYPE: amino acid
        ( C ) STRANDEDNESS: single
        ( D ) TOPOLOGY: linear ( x i ) SEQUENCE DESCRIPTION: SEQ ID NO:11:

```
Arg  Asp  Ile  Tyr  Glu  Thr  Asp  Tyr  Pro  Met  Xaa  Arg  Lys
 1              5                        10
```

( 2 ) INFORMATION FOR SEQ ID NO:12:

( i ) SEQUENCE CHARACTERISTICS:
        ( A ) LENGTH: 11
        ( B ) TYPE: amino acid
        ( C ) STRANDEDNESS: single
        ( D ) TOPOLOGY: linear ( x i ) SEQUENCE DESCRIPTION: SEQ ID NO:12:

```
Thr  Glu  Pro  Glu  Xaa  Met  Pro  Gln  Pro  Gly  Glu
 1              5                        10
```

( 2 ) INFORMATION FOR SEQ ID NO:13:

( i ) SEQUENCE CHARACTERISTICS:
        ( A ) LENGTH: 18
        ( B ) TYPE: amino acid
        ( C ) STRANDEDNESS: single
        ( D ) TOPOLOGY: linear ( x i ) SEQUENCE DESCRIPTION: SEQ ID NO:13:

```
Lys  Asp  Glu  Ser  Ile  Asp  Xaa  Met  Pro  Val  Pro  Met  Leu  Asp  Met  Lys
 1              5                        10                            15
Gly  Asp
```

( 2 ) INFORMATION FOR SEQ ID NO:14:

( i ) SEQUENCE CHARACTERISTICS:
        ( A ) LENGTH: 15
        ( B ) TYPE: amino acid
        ( C ) STRANDEDNESS: single
        ( D ) TOPOLOGY: linear ( x i ) SEQUENCE DESCRIPTION: SEQ ID NO:14:

Arg Glu Asn Glu Pro Met Xaa Met Pro Met Ala Pro Gln Ile His
1               5                   10                      15

( 2 ) INFORMATION FOR SEQ ID NO:15:

( i ) SEQUENCE CHARACTERISTICS:
        ( A ) LENGTH: 14
        ( B ) TYPE: amino acid
        ( C ) STRANDEDNESS: single
        ( D ) TOPOLOGY: linear ( x i ) SEQUENCE DESCRIPTION: SEQ ID NO:15:

Thr Asp Asp Gly Xaa Met Pro Met Pro Met Ser Pro Gly Val
1               5                   10

( 2 ) INFORMATION FOR SEQ ID NO:16:

( i ) SEQUENCE CHARACTERISTICS:
        ( A ) LENGTH: 14
        ( B ) TYPE: amino acid
        ( C ) STRANDEDNESS: single
        ( D ) TOPOLOGY: linear ( x i ) SEQUENCE DESCRIPTION: SEQ ID NO:16:

Gly Asn Gly Asp Xaa Met Pro Met Pro Met Ser Pro Lys Ser
1               5                   10

( 2 ) INFORMATION FOR SEQ ID NO:17:

( i ) SEQUENCE CHARACTERISTICS:
        ( A ) LENGTH: 11
        ( B ) TYPE: amino acid
        ( C ) STRANDEDNESS: single
        ( D ) TOPOLOGY: linear ( x i ) SEQUENCE DESCRIPTION: SEQ ID NO:17:

Arg Asp Ile Xaa Glu Thr Asp Tyr Tyr Arg Lys
1               5                   10

( 2 ) INFORMATION FOR SEQ ID NO:18:

( i ) SEQUENCE CHARACTERISTICS:
        ( A ) LENGTH: 11
        ( B ) TYPE: amino acid
        ( C ) STRANDEDNESS: single
        ( D ) TOPOLOGY: linear ( x i ) SEQUENCE DESCRIPTION: SEQ ID NO:18:

Arg Asp Ile Xaa Glu Thr Asp Tyr Tyr Arg Lys
1               5                   10

( 2 ) INFORMATION FOR SEQ ID NO:19:

( i ) SEQUENCE CHARACTERISTICS:
        ( A ) LENGTH: 11
        ( B ) TYPE: amino acid
        ( C ) STRANDEDNESS: single
        ( D ) TOPOLOGY: linear ( x i ) SEQUENCE DESCRIPTION: SEQ ID NO:19:

Arg Asp Ile Xaa Glu Thr Asp Xaa Xaa Arg
1               5                   10
Lys ( 2 ) INFORMATION FOR SEQ ID NO:20:

( i ) SEQUENCE CHARACTERISTICS:
    ( A ) LENGTH: 4
    ( B ) TYPE: amino acid
    ( C ) STRANDEDNESS: single
    ( D ) TOPOLOGY: linear ( x i ) SEQUENCE DESCRIPTION: SEQ ID NO:20:

Tyr Met Xaa Met
              4

( 2 ) INFORMATION FOR SEQ ID NO:21:

( i ) SEQUENCE CHARACTERISTICS:
        ( A ) LENGTH: 14
        ( B ) TYPE: amino acid
        ( C ) STRANDEDNESS: single
        ( D ) TOPOLOGY: linear ( x i ) SEQUENCE DESCRIPTION: SEQ ID NO:21:

His Arg Glu Asn Glu Xaa Met Pro Met Ala Pro Glu Ile His
 1               5                  10

( 2 ) INFORMATION FOR SEQ ID NO:22:

( i ) SEQUENCE CHARACTERISTICS:
        ( A ) LENGTH: 10
        ( B ) TYPE: amino acid
        ( C ) STRANDEDNESS: single
        ( D ) TOPOLOGY: linear ( x i ) SEQUENCE DESCRIPTION: SEQ ID NO:22:

Arg Leu Glu Tyr Tyr Glu Asn Glu Lys Lys
 1               5                   10

( 2 ) INFORMATION FOR SEQ ID NO:23:

( i ) SEQUENCE CHARACTERISTICS:
        ( A ) LENGTH: 16
        ( B ) TYPE: amino acid
        ( C ) STRANDEDNESS: single
        ( D ) TOPOLOGY: linear ( x i ) SEQUENCE DESCRIPTION: SEQ ID NO:23:

Lys Arg Gly Glu Glu Glu Leu Ser Asn Tyr Ile Cys Met Gly Gly Lys
 1               5                  10                      15

( 2 ) INFORMATION FOR SEQ ID NO:24:

( i ) SEQUENCE CHARACTERISTICS:
        ( A ) LENGTH: 15
        ( B ) TYPE: amino acid
        ( C ) STRANDEDNESS: single
        ( D ) TOPOLOGY: linear ( x i ) SEQUENCE DESCRIPTION: SEQ ID NO:24:

Lys Lys Val Ser Ile Glu Glu Tyr Thr Glu Met Met Pro Ala Lys
 1               5                  10                  15

( 2 ) INFORMATION FOR SEQ ID NO:25:

( i ) SEQUENCE CHARACTERISTICS:
        ( A ) LENGTH: 16
        ( B ) TYPE: amino acid
        ( C ) STRANDEDNESS: single
        ( D ) TOPOLOGY: linear ( x i ) SEQUENCE DESCRIPTION: SEQ ID NO:25:

Lys Lys His Thr Asp Asp Gly Val Met Pro Met Ser Pro Gly Val Ala (2) INFORMATION FOR SEQ ID NO:26:

(i) SEQUENCE CHARACTERISTICS:
        (A) LENGTH: 16
        (B) TYPE: amino acid
        (C) STRANDEDNESS: single
        (D) TOPOLOGY: linear (xi) SEQUENCE DESCRIPTION: SEQ ID NO:26:

```
Arg Lys Gly Asn Gly Asp Gly Tyr Met Pro Met Ser Pro Lys Ser Val
 1               5                  10                  15
```

(2) INFORMATION FOR SEQ ID NO:27:

(i) SEQUENCE CHARACTERISTICS:
        (A) LENGTH: 17
        (B) TYPE: amino acid
        (C) STRANDEDNESS: single
        (D) TOPOLOGY: linear (xi) SEQUENCE DESCRIPTION: SEQ ID NO:27:

```
Lys Lys Arg Val Asp Pro Asn Gly Tyr Met Met Met Ser Pro Ser Gly
 1               5                  10                  15
Ser
```

(2) INFORMATION FOR SEQ ID NO:28:

(i) SEQUENCE CHARACTERISTICS:
        (A) LENGTH: 18
        (B) TYPE: amino acid
        (C) STRANDEDNESS: single
        (D) TOPOLOGY: linear (xi) SEQUENCE DESCRIPTION: SEQ ID NO:28:

```
Lys Lys Lys Leu Pro Ala Thr Gly Asp Tyr Met Asn Met Ser Pro Val
 1               5                  10                  15
Gly Asp
```

(2) INFORMATION FOR SEQ ID NO:29:

(i) SEQUENCE CHARACTERISTICS:
        (A) LENGTH: 16
        (B) TYPE: amino acid
        (C) STRANDEDNESS: single
        (D) TOPOLOGY: linear (xi) SEQUENCE DESCRIPTION: SEQ ID NO: 29:

```
Lys Lys Gly Ser Glu Glu Tyr Met Asn Met Asp Leu Gly Pro Gly Arg
 1               5                  10                  15
```

(2) INFORMATION FOR SEQ ID NO:30:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO:30:

```
Lys Lys Ser Arg Gly Asp Tyr Met Thr Met Gln Ile Gly
 1               5                  10
```

(2) INFORMATION FOR SEQ ID NO:31:

(i) SEQUENCE CHARACTERISTICS:

(A) LENGTH: 15
(B) TYPE: amino acid
(C) STRANDEDNESS: single
(D) TOPOLOGY: linear (xi) SEQUENCE DESCRIPTION: SEQ ID NO:31:

Lys Pro Arg Asn Ser Tyr Val Asp Thr Ser Pro Val Ala Pro Lys
1               5                   10                  15

(2) INFORMATION FOR SEQ ID NO:32:

(i) SEQUENCE CHARACTERISTICS:
(A) LENGTH: 11
(B) TYPE: amino acid
(C) STRANDEDNESS: single
(D) TOPOLOGY: linear (xi) SEQUENCE DESCRIPTION: SEQ ID NO:32:

Glu Glu Glu Tyr Met Pro Met Glu Asp Leu Tyr
1               5                   10

(2) INFORMATION FOR SEQ ID NO:33:

(i) SEQUENCE CHARACTERISTICS:
(A) LENGTH: 11
(B) TYPE: amino acid
(C) STRANDEDNESS: single
(D) TOPOLOGY: linear (xi) SEQUENCE DESCRIPTION: SEQ ID NO:33:

Asp Gly Gly Tyr Met Asp Met Ser Lys Asp Glu
1               5                   10

(2) INFORMATION FOR SEQ ID NO:34:

(i) SEQUENCE CHARACTERISTICS:
(A) LENGTH: 11
(B) TYPE: amino acid
(C) STRANDEDNESS: single
(D) TOPOLOGY: linear (xi) SEQUENCE DESCRIPTION: SEQ ID NO:34:

Ser Ile Asp Tyr Val Pro Met Leu Asp Met Lys
1               5                   10

(2) INFORMATION FOR SEQ ID NO:35:

(i) SEQUENCE CHARACTERISTICS:
(A) LENGTH: 13
(B) TYPE: amino acid
(C) STRANDEDNESS: single
(D) TOPOLOGY: linear (xi) SEQUENCE DESCRIPTION: SEQ ID NO:35:

Arg Glu Asn Glu Tyr Met Pro Met Ala Pro Gln Ile His
1               5                   10

(2) INFORMATION FOR SEQ ID NO:36:

(i) SEQUENCE CHARACTERISTICS:
(A) LENGTH: 13
(B) TYPE: amino acid
(C) STRANDEDNESS: single
(D) TOPOLOGY: linear (xi) SEQUENCE DESCRIPTION: SEQ ID NO:36:

Glu Glu Glu Glu Tyr Met Pro Met Glu Asp Leu Tyr Leu
1               5                   10

(2) INFORMATION FOR SEQ ID NO:37:

(i) SEQUENCE CHARACTERISTICS:
       (A) LENGTH: 13
       (B) TYPE: amino acid
       (C) STRANDEDNESS: single
       (D) TOPOLOGY: linear (xi) SEQUENCE DESCRIPTION: SEQ ID NO:37:

```
Thr Asp Asp Gly Tyr Met Pro Met Ser Pro Gly Val Ala
 1               5                   10
```

(2) INFORMATION FOR SEQ ID NO:38:

(i) SEQUENCE CHARACTERISTICS:
       (A) LENGTH: 13
       (B) TYPE: amino acid
       (C) STRANDEDNESS: single
       (D) TOPOLOGY: linear (xi) SEQUENCE DESCRIPTION: SEQ ID NO:38:

```
Gly Asn Gly Asp Tyr Met Pro Met Ser Pro Lys Ser Val
 1               5                   10
```

(2) INFORMATION FOR SEQ ID NO:39:

(i) SEQUENCE CHARACTERISTICS:
       (A) LENGTH: 13
       (B) TYPE: amino acid
       (C) STRANDEDNESS: single
       (D) TOPOLOGY: linear (xi) SEQUENCE DESCRIPTION: SEQ ID NO:39:

```
Ala Pro Val Ser Tyr Ala Asp Met Arg Thr Gly Ile Ala
 1               5                   10
```

(2) INFORMATION FOR SEQ ID NO:40:

(i) SEQUENCE CHARACTERISTICS:
       (A) LENGTH: 13
       (B) TYPE: amino acid
       (C) STRANDEDNESS: single
       (D) TOPOLOGY: linear (xi) SEQUENCE DESCRIPTION: SEQ ID NO:40:

```
Glu Ser Val Asp Tyr Val Pro Met Leu Asp Met Lys Gly
 1               5                   10
```

(2) INFORMATION FOR SEQ ID NO:41:

(i) SEQUENCE CHARACTERISTICS:
       (A) LENGTH: 13
       (B) TYPE: amino acid
       (C) STRANDEDNESS: single
       (D) TOPOLOGY: linear (xi) SEQUENCE DESCRIPTION: SEQ ID NO:41:

```
Ser Asp Gly Gly Tyr Met Asp Met Ser Lys Asp Glu Ser
 1               5                   10
```

(2) INFORMATION FOR SEQ ID NO:42:

(i) SEQUENCE CHARACTERISTICS:
       (A) LENGTH: 11
       (B) TYPE: amino acid
       (C) STRANDEDNESS: single
       (D) TOPOLOGY: linear (xi) SEQUENCE DESCRIPTION: SEQ ID NO:42:

```
Arg Asp Ile Xaa Glu Thr Asp Xaa Xaa Arg Lys
 1               5                        10
```

( 2 ) INFORMATION FOR SEQ ID NO:43:

( i ) SEQUENCE CHARACTERISTICS:
        ( A ) LENGTH: 11
        ( B ) TYPE: amino acid
        ( C ) STRANDEDNESS: single
        ( D ) TOPOLOGY: linear ( x i ) SEQUENCE DESCRIPTION: SEQ ID NO:43:

```
Glu Glu Glu Xaa Met Pro Met Glu Asp Leu Tyr
 1               5                        10
```

( 2 ) INFORMATION FOR SEQ ID NO:44:

( i ) SEQUENCE CHARACTERISTICS:
        ( A ) LENGTH: 11
        ( B ) TYPE: amino acid
        ( C ) STRANDEDNESS: single
        ( D ) TOPOLOGY: linear ( x i ) SEQUENCE DESCRIPTION: SEQ ID NO:44:

```
Arg Asp Ile Xaa Glu Thr Asp Tyr Tyr Arg Lys
 1               5                        10
```

( 2 ) INFORMATION FOR SEQ ID NO:45:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:45:

```
    Gly Xaa Val Pro Met Leu
     1               5
```

( 2 ) INFORMATION FOR SEQ ID NO:46:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:46:

```
Asp Xaa Val Pro Met Leu
 1               5
```

( 2 ) INFORMATION FOR SEQ ID NO:47:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:47:

```
            Gln  Xaa  Glu  Glu  Ile  Pro
            1                  5
```

(2) INFORMATION FOR SEQ ID NO:48:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:48:

```
            Asn  Xaa  Val  Asn  Ile  Glu
            1                  5
```

(2) INFORMATION FOR SEQ ID NO:49:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:49:

```
            Glu  Asp  Leu  Ser  Xaa  Asp  Thr  Gly  Pro  Gly  Pro  Ala
            1                  5                       10
```

(2) INFORMATION FOR SEQ ID NO:50:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:50:

```
            Leu  Ser  Asn  Xaa  Ile  Cys  Met  Gly  Gly  Lys  Gly
            1                  5                       10
```

(2) INFORMATION FOR SEQ ID NO:51:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:51:

```
            Ile  Glu  Glu  Xaa  Thr  Glu  Met  Met  Pro  Ala  Ala
            1                  5                       10
```

(2) INFORMATION FOR SEQ ID NO:52:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:52:

Asp Asp Gly Xaa Met Pro Met Ser Pro Gly Val
1               5                   10

(2) INFORMATION FOR SEQ ID NO:53:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:53:

Gly Asn Gly Asp Xaa Met Pro Met Ser Pro Lys Ser
1               5                   10

(2) INFORMATION FOR SEQ ID NO:54:

(i) SEQUENCE CHARACTERISTICS:
      (A) LENGTH: 11 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:54:

Pro Asn Gly Xaa Met Met Met Ser Pro Ser Gly
1               5                   10

(2) INFORMATION FOR SEQ ID NO:55:

(i) SEQUENCE CHARACTERISTICS:
      (A) LENGTH: 11 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:55:

Thr Gly Asp Xaa Met Asn Met Ser Pro Val Gly
1               5                   10

(2) INFORMATION FOR SEQ ID NO:56:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:56:

Ser Pro Gly Glu Xaa Val Asn Ile Glu Phe Gly Ser
1               5                   10

(2) INFORMATION FOR SEQ ID NO:57:

(i) SEQUENCE CHARACTERISTICS:

(A) LENGTH: 11 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:57:

Ser Glu Glu Xaa Met Asn Met Asp Leu Pro Gly
1               5                   10

(2) INFORMATION FOR SEQ ID NO:58:

(i) SEQUENCE CHARACTERISTICS:
(A) LENGTH: 10 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:58:

Arg Asp Gly Xaa Met Thr Met Gln Ile Gly
1               5                   10

(2) INFORMATION FOR SEQ ID NO:59:

(i) SEQUENCE CHARACTERISTICS:
(A) LENGTH: 11 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:59:

Pro Val Ser Xaa Ala Asp Met Arg Thr Gly Ile
1               5                   10

(2) INFORMATION FOR SEQ ID NO:60:

(i) SEQUENCE CHARACTERISTICS:
(A) LENGTH: 9 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:60:

Leu Asn Xaa Ile Asp Leu Asp Leu Val
1             5

(2) INFORMATION FOR SEQ ID NO:61:

(i) SEQUENCE CHARACTERISTICS:
(A) LENGTH: 11 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:61:

Leu Ser Thr Xaa Ala Ser Ile Asn Phe Gln Lys
1               5                   10

( 2 ) INFORMATION FOR SEQ ID NO:62:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:62:

```
Ser Leu Asn Xaa Ile Asp Leu Asp Leu Val Xaa
1               5                   10
```

( 2 ) INFORMATION FOR SEQ ID NO:63:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:63:

```
Leu Asn Xaa Ile Asp Leu Asp Xaa
1               5
```

( 2 ) INFORMATION FOR SEQ ID NO:64:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:64:

```
Leu Asn Xaa Ile Asp Leu Xaa
1               5
```

( 2 ) INFORMATION FOR SEQ ID NO:65:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:65:

```
Leu Asn Xaa Ile Asp Xaa
1               5
```

( 2 ) INFORMATION FOR SEQ ID NO:66:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:66:

Ser Pro Gly Glu Xaa Val Asn Ile Glu Asp Gly Ser
1               5                   10

( 2 ) INFORMATION FOR SEQ ID NO:67:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:67:

Ile Asp Val Xaa Met Ile Met Val Lys
1               5

( 2 ) INFORMATION FOR SEQ ID NO:68:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:68:

Pro Gln Arg Xaa Leu Val Ile Gln Gly Asp
1               5                   10

( 2 ) INFORMATION FOR SEQ ID NO:69:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:69:

Asp Ala Asp Glu Xaa Leu Ile Pro Gln Gln Gly Phe Phe
1               5                   10

( 2 ) INFORMATION FOR SEQ ID NO:70:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:70:

Val Pro Glu Xaa Ile Asn Gln Ser Val Pro Lys
1               5                   10

( 2 ) INFORMATION FOR SEQ ID NO:71:

( i ) SEQUENCE CHARACTERISTICS:
        ( A ) LENGTH: 10 amino acids
        ( B ) TYPE: amino acid (D) TOPOLOGY: linear (ii) MOLECULE TYPE: peptide (v) FRAGMENT TYPE: internal (xi) SEQUENCE DESCRIPTION: SEQ ID NO:71:

Asn Pro Val Xaa His Asn Gln Pro Leu Asn
    1               5                   10

(2) INFORMATION FOR SEQ ID NO:72:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:72:

Asn Pro Glu Xaa Leu Asn Thr Val Gln Pro Thr
    1               5                   10

(2) INFORMATION FOR SEQ ID NO:73:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:73:

Asn Pro Asp Xaa Gln Gln Asp Phe Phe Pro Lys
    1               5                   10

(2) INFORMATION FOR SEQ ID NO:74:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:74:

Asn Ala Glu Xaa Leu Arg Val Ala Pro Gln Ser
    1               5                   10

(2) INFORMATION FOR SEQ ID NO:75:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:75:

Gly His Glu Xaa Ile Tyr Val Asp Pro Met
    1               5                   10

( 2 ) INFORMATION FOR SEQ ID NO:76:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:76:

```
Gly His Glu Tyr Ile Xaa Val Asp Pro Met
1               5                   10
```

( 2 ) INFORMATION FOR SEQ ID NO:77:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:77:

```
Gly His Glu Xaa Ile Xaa Val Asp Pro Met
1               5                   10
```

( 2 ) INFORMATION FOR SEQ ID NO:78:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:78:

```
Ala Glu Leu Xaa Ser Asn Ala Leu Pro Val
1               5                   10
```

( 2 ) INFORMATION FOR SEQ ID NO:79:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:79:

```
Asp Gly Gly Xaa Met Asp Met Ser Lys Asp Glu
1               5                   10
```

( 2 ) INFORMATION FOR SEQ ID NO:80:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:80:

```
    Ser  Val  Asp  Xaa  Val  Pro  Met  Leu  Asp  Met  Lys
    1              5                        10
```

( 2 ) INFORMATION FOR SEQ ID NO:81:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:81:

```
    Ser  Ser  Asn  Xaa  Met  Ala  Pro  Tyr  Asp  Asn  Tyr
    1              5                        10
```

( 2 ) INFORMATION FOR SEQ ID NO:82:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:82:

```
    Met  Ala  Pro  Xaa  Asp  Asn  Tyr  Val  Pro  Ser
    1              5                        10
```

( 2 ) INFORMATION FOR SEQ ID NO:83:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:83:

```
    Ser  Val  Leu  Xaa  Thr  Ala  Val  Gln  Pro  Asn  Glu
    1              5                        10
```

( 2 ) INFORMATION FOR SEQ ID NO:84:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:84:

```
    Asp  Asn  Asp  Xaa  Ile  Ile  Pro  Leu  Pro  Asp  Pro  Lys
    1              5                        10
```

( 2 ) INFORMATION FOR SEQ ID NO:85:

( i ) SEQUENCE CHARACTERISTICS:
        ( A ) LENGTH: 12 amino acids
        ( B ) TYPE: amino acid
        ( D ) TOPOLOGY: linear (i i) MOLECULE TYPE: peptide (v) FRAGMENT TYPE: internal (x i) SEQUENCE DESCRIPTION: SEQ ID NO:85:

```
Glu  Asp  Asp  Gly  Xaa  Asp  Val  Pro  Lys  Pro  Pro  Val
1                  5                        10
```

(2) INFORMATION FOR SEQ ID NO:86:

(i) SEQUENCE CHARACTERISTICS:
   (A) LENGTH: 6 amino acids
   (B) TYPE: amino acid
   (D) TOPOLOGY: linear (i i) MOLECULE TYPE: peptide (v) FRAGMENT TYPE: internal (x i) SEQUENCE DESCRIPTION: SEQ ID NO:86:

```
Xaa  Xaa  Asp  Ala  Pro  Xaa
1                  5
```

(2) INFORMATION FOR SEQ ID NO:87:

(i) SEQUENCE CHARACTERISTICS:
   (A) LENGTH: 9 amino acids
   (B) TYPE: amino acid
   (D) TOPOLOGY: linear (i i) MOLECULE TYPE: peptide (v) FRAGMENT TYPE: internal (x i) SEQUENCE DESCRIPTION: SEQ ID NO:87:

```
Pro  Pro  Val  Xaa  Leu  Asp  Val  Leu  Gly
1                  5
```

(2) INFORMATION FOR SEQ ID NO:88:

(i) SEQUENCE CHARACTERISTICS:
   (A) LENGTH: 9 amino acids
   (B) TYPE: amino acid
   (D) TOPOLOGY: linear (i i) MOLECULE TYPE: peptide (v) FRAGMENT TYPE: internal (x i) SEQUENCE DESCRIPTION: SEQ ID NO:88:

```
Ser  Pro  Val  Xaa  Leu  Asp  Ile  Leu  Gly
1                  5
```

(2) INFORMATION FOR SEQ ID NO:89:

(i) SEQUENCE CHARACTERISTICS:
   (A) LENGTH: 10 amino acids
   (B) TYPE: amino acid
   (D) TOPOLOGY: linear (i i) MOLECULE TYPE: cDNA (v) FRAGMENT TYPE: internal (x i) SEQUENCE DESCRIPTION: SEQ ID NO:89:

```
Glu  Pro  Gln  Xaa  Gln  Pro  Gly  Glu  Asn  Leu
1                  5                        10
```

(2) INFORMATION FOR SEQ ID NO:90:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( v ) FRAGMENT TYPE: internal ( x i ) SEQUENCE DESCRIPTION: SEQ ID NO:90:

```
Glu Pro Gln Tyr Gln Pro Gly Glu Asn Leu
1               5                   10
```

( 2 ) INFORMATION FOR SEQ ID NO:91:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:91:

```
Thr Glu Gly Gln Xaa Gln Pro Gln Pro Ala
1               5                   10
```

( 2 ) INFORMATION FOR SEQ ID NO:92:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:92:

```
Glu Gly Gln Xaa Gln Pro Gln Pro
1               5
```

( 2 ) INFORMATION FOR SEQ ID NO:93:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: misc_feature
    ( B ) LOCATION: Residue No. 4
    ( C ) OTHER INFORMATION: Xaa =pY ( x i ) SEQUENCE DESCRIPTION: SEQ ID NO:93:

```
Glu Pro Gln Xaa Glu Glu Ile Pro Ile Tyr Leu
1               5                   10
```

( 2 ) INFORMATION FOR SEQ ID NO:94:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: misc_feature
    ( B ) LOCATION: Residue No. 1
    ( C ) OTHER INFORMATION: Xaa = Ac- Glutamine ( i x ) FEATURE:
    ( A ) NAME/KEY: misc_feature
    ( B ) LOCATION: Residue No. 2
    ( C ) OTHER INFORMATION: Xaa =pY ( i x ) FEATURE:
    ( A ) NAME/KEY: misc_feature
    ( B ) LOCATION: Residue No. 6
    ( C ) OTHER INFORMATION: Xaa = Pro- NH2

( x i ) SEQUENCE DESCRIPTION: SEQ ID NO:94:

Xaa  Xaa  Glu  Glu  Ile  Xaa
1                        5

( 2 ) INFORMATION FOR SEQ ID NO:95:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:95:

Xaa  Glu  Glu  Ile  Xaa
1                   5

( 2 ) INFORMATION FOR SEQ ID NO:96:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:96:

Xaa  Glu  Glu  Xaa
1

( 2 ) INFORMATION FOR SEQ ID NO:97:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:97:

Xaa  Glu  Xaa
1

( 2 ) INFORMATION FOR SEQ ID NO:98:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:98:

```
Glu Pro Gln Xaa Glu Glu Leu Pro Ile Tyr Leu
1               5                   10
```

( 2 ) INFORMATION FOR SEQ ID NO:99:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:99:

```
Glu Pro Gln Xaa Glu Glu Met Pro Ile Tyr Leu
1               5                   10
```

( 2 ) INFORMATION FOR SEQ ID NO:100:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:100:

```
Glu Pro Gln Xaa Glu Glu Val Pro Ile Tyr Leu
1               5                   10
```

( 2 ) INFORMATION FOR SEQ ID NO:101:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:101:

```
Xaa Glu Glu Ile Xaa
1               5
```

( 2 ) INFORMATION FOR SEQ ID NO:102:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:102:

```
Val Ser Asp Xaa Ile Asn Ala Asn Ile Ile
1               5                   10
```

( 2 ) INFORMATION FOR SEQ ID NO:103:

( i ) SEQUENCE CHARACTERISTICS:
(A) LENGTH: 11 amino acids
(B) TYPE: amino acid
(D) TOPOLOGY: linear ( i i ) MOLECULE TYPE: peptide ( v ) FRAGMENT TYPE: internal ( x i ) SEQUENCE DESCRIPTION: SEQ ID NO:103:

Gly His Glu Xaa Thr Asn Ile Lys Tyr Ser Leu
1               5                   10

( 2 ) INFORMATION FOR SEQ ID NO:104:

( i ) SEQUENCE CHARACTERISTICS:
(A) LENGTH: 11 amino acids
(B) TYPE: amino acid
(D) TOPOLOGY: linear ( i i ) MOLECULE TYPE: peptide ( v ) FRAGMENT TYPE: internal ( x i ) SEQUENCE DESCRIPTION: SEQ ID NO:104:

Ala Arg Val Xaa Glu Asn Val Gly Leu Met Gln
1               5                   10

( 2 ) INFORMATION FOR SEQ ID NO:105:

( i ) SEQUENCE CHARACTERISTICS:
(A) LENGTH: 9 amino acids
(B) TYPE: amino acid
(D) TOPOLOGY: linear ( i i ) MOLECULE TYPE: peptide ( v ) FRAGMENT TYPE: internal ( x i ) SEQUENCE DESCRIPTION: SEQ ID NO:105:

Lys Pro Phe Xaa Val Asn Val Glu Phe
1               5

( 2 ) INFORMATION FOR SEQ ID NO:106:

( i ) SEQUENCE CHARACTERISTICS:
(A) LENGTH: 10 amino acids
(B) TYPE: amino acid
(D) TOPOLOGY: linear ( i i ) MOLECULE TYPE: peptide ( v ) FRAGMENT TYPE: internal ( x i ) SEQUENCE DESCRIPTION: SEQ ID NO:106:

His Ser Asp Xaa Met Asn Met Thr Pro Arg
1               5                   10

( 2 ) INFORMATION FOR SEQ ID NO:107:

( i ) SEQUENCE CHARACTERISTICS:
(A) LENGTH: 9 amino acids
(B) TYPE: amino acid
(D) TOPOLOGY: linear ( i i ) MOLECULE TYPE: peptide ( v ) FRAGMENT TYPE: internal ( x i ) SEQUENCE DESCRIPTION: SEQ ID NO:107:

```
Xaa Asp Xaa Ile Ile Pro Leu Pro Xaa
1               5
```

( 2 ) INFORMATION FOR SEQ ID NO:108:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: misc_feature
        ( B ) LOCATION: Residue No. 1
        ( C ) OTHER INFORMATION: Xaa = Ac- D ( i x ) FEATURE:
        ( A ) NAME/KEY: misc_feature
        ( B ) LOCATION: Residue No. 2
        ( C ) OTHER INFORMATION: Xaa =pY ( i x ) FEATURE:
        ( A ) NAME/KEY: misc_feature
        ( B ) LOCATION: Residue No. 8
        ( C ) OTHER INFORMATION: Xaa = D- NH2

( x i ) SEQUENCE DESCRIPTION: SEQ ID NO:108:

```
Xaa Xaa Ile Ile Pro Leu Pro Xaa
1               5
```

( 2 ) INFORMATION FOR SEQ ID NO:109:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:109:

```
Xaa Xaa Ile Ile Pro Leu Xaa
1               5
```

( 2 ) INFORMATION FOR SEQ ID NO:110:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: misc_feature
        ( B ) LOCATION: Residue No. 1
        ( C ) OTHER INFORMATION: Xaa = Ac- D ( i x ) FEATURE:
        ( A ) NAME/KEY: misc_feature
        ( B ) LOCATION: Residue No. 2
        ( C ) OTHER INFORMATION: Xaa =pY ( i x ) FEATURE:
        ( A ) NAME/KEY: misc_feature
        ( B ) LOCATION: Residue No. 6
        ( C ) OTHER INFORMATION: Xaa = L- NH2

( x i ) SEQUENCE DESCRIPTION: SEQ ID NO:110:

```
Xaa Xaa Ile Ile Pro Xaa
 1               5
```

( 2 ) INFORMATION FOR SEQ ID NO:111:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: misc_feature
        ( B ) LOCATION: Residue No. 1
        ( C ) OTHER INFORMATION: Xaa = Ac- A ( i x ) FEATURE:
        ( A ) NAME/KEY: misc_feature
        ( B ) LOCATION: Residue No. 2
        ( C ) OTHER INFORMATION: Xaa =pY ( i x ) FEATURE:
        ( A ) NAME/KEY: misc_feature
        ( B ) LOCATION: Residue No. 6
        ( C ) OTHER INFORMATION: Xaa = L- NH2

( x i ) SEQUENCE DESCRIPTION: SEQ ID NO:111:

```
Xaa Xaa Ile Ile Pro Xaa
 1               5
```

( 2 ) INFORMATION FOR SEQ ID NO:112:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: misc_feature
        ( B ) LOCATION: Residue No. 1
        ( C ) OTHER INFORMATION: Xaa = Ac- D ( i x ) FEATURE:
        ( A ) NAME/KEY: misc_feature
        ( B ) LOCATION: Residue No. 2
        ( C ) OTHER INFORMATION: Xaa =Pmp ( i x ) FEATURE:
        ( A ) NAME/KEY: misc_feature
        ( B ) LOCATION: Residue No. 6
        ( C ) OTHER INFORMATION: Xaa = L- NH2

( x i ) SEQUENCE DESCRIPTION: SEQ ID NO:112:

```
Xaa Xaa Ile Ile Pro Xaa
 1               5
```

( 2 ) INFORMATION FOR SEQ ID NO:113:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:113:

Xaa Xaa Ile Ile Xaa
1               5

( 2 ) INFORMATION FOR SEQ ID NO:114:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:114:

Xaa Xaa Ile Xaa
1

( 2 ) INFORMATION FOR SEQ ID NO:115:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:115:

Xaa Xaa Xaa
1

( 2 ) INFORMATION FOR SEQ ID NO:116:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:116:

Xaa Ile Ile Xaa
1

( 2 ) INFORMATION FOR SEQ ID NO:117:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:117:

Xaa Ile Xaa
1

( 2 ) INFORMATION FOR SEQ ID NO:118:

( i ) SEQUENCE CHARACTERISTICS:
        ( A ) LENGTH: 8 amino acids
        ( B ) TYPE: amino acid
        ( D ) TOPOLOGY: linear (ii) MOLECULE TYPE: peptide (v) FRAGMENT TYPE: internal (ix) FEATURE:
 (A) NAME/KEY: misc_feature
 (B) LOCATION: Residue No. 1
 (C) OTHER INFORMATION: Xaa = Ac- D (ix) FEATURE:
 (A) NAME/KEY: misc_feature
 (B) LOCATION: Residue No. 2
 (C) OTHER INFORMATION: Xaa =pY (ix) FEATURE:
 (A) NAME/KEY: misc_feature
 (B) LOCATION: Residue No. 8
 (C) OTHER INFORMATION: Xaa = R- NH2

(xi) SEQUENCE DESCRIPTION: SEQ ID NO:118:

Xaa Xaa Ile Ile Pro Leu Pro Xaa
1       5

(2) INFORMATION FOR SEQ ID NO:119:

(i) SEQUENCE CHARACTERISTICS:
  (A) LENGTH: 8 amino acids
  (B) TYPE: amino acid
  (D) TOPOLOGY: linear (ii) MOLECULE TYPE: peptide (v) FRAGMENT TYPE: internal (ix) FEATURE:
  (A) NAME/KEY: misc_feature
  (B) LOCATION: Residue No. 1
  (C) OTHER INFORMATION: Xaa = Ac- D (ix) FEATURE:
  (A) NAME/KEY: misc_feature
  (B) LOCATION: Residue No. 2
  (C) OTHER INFORMATION: Xaa =pY (ix) FEATURE:
  (A) NAME/KEY: misc_feature
  (B) LOCATION: Residue No. 8
  (C) OTHER INFORMATION: Xaa = R- NH2

(xi) SEQUENCE DESCRIPTION: SEQ ID NO:119:

Xaa Xaa Ile Ile Pro Leu Asp Xaa
1       5

(2) INFORMATION FOR SEQ ID NO:120:

(i) SEQUENCE CHARACTERISTICS:
  (A) LENGTH: 8 amino acids
  (B) TYPE: amino acid
  (D) TOPOLOGY: linear (ii) MOLECULE TYPE: peptide (v) FRAGMENT TYPE: internal (xi) SEQUENCE DESCRIPTION: SEQ ID NO:120:

Xaa Xaa Ile Ile Pro Asp Pro Xaa
1       5

(2) INFORMATION FOR SEQ ID NO:121:

(i) SEQUENCE CHARACTERISTICS:
  (A) LENGTH: 8 amino acids
  (B) TYPE: amino acid (D) TOPOLOGY: linear (ii) MOLECULE TYPE: peptide (v) FRAGMENT TYPE: internal (xi) SEQUENCE DESCRIPTION: SEQ ID NO:121:

Xaa Xaa Ile Ile Asp Leu Pro Xaa
1               5

(2) INFORMATION FOR SEQ ID NO:122:

(i) SEQUENCE CHARACTERISTICS:
(A) LENGTH: 8 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:122:

Xaa Xaa Ile Asp Pro Leu Pro Xaa
1               5

(2) INFORMATION FOR SEQ ID NO:123:

(i) SEQUENCE CHARACTERISTICS:
(A) LENGTH: 8 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: misc_feature
(B) LOCATION: Residue No. 1
(C) OTHER INFORMATION: Xaa = Ac- D (ix) FEATURE:
(A) NAME/KEY: misc_feature
(B) LOCATION: Residue No. 2
(C) OTHER INFORMATION: Xaa =pY (ix) FEATURE:
(A) NAME/KEY: misc_feature
(B) LOCATION: Residue No. 8
(C) OTHER INFORMATION: Xaa = D- NH2

(xi) SEQUENCE DESCRIPTION: SEQ ID NO:123:

Xaa Xaa Asp Ile Pro Leu Pro Xaa
1               5

(2) INFORMATION FOR SEQ ID NO:124:

(i) SEQUENCE CHARACTERISTICS:
(A) LENGTH: 13 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:124:

Leu Leu Ser Asn Pro Thr Xaa Ser Val Met Arg Ser Lys
1               5                   10

(2) INFORMATION FOR SEQ ID NO:125:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:125:

Leu Ser Asn Pro Thr Xaa Ser Val Met Arg Ser Lys
1               5                   10

( 2 ) INFORMATION FOR SEQ ID NO:126:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:126:

Leu Leu Ser Asn Pro Thr Xaa Ser Val
1               5

( 2 ) INFORMATION FOR SEQ ID NO:127:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:127:

Leu Leu Ser Asn Pro Thr Xaa Ser
1               5

( 2 ) INFORMATION FOR SEQ ID NO:128:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:128:

Leu Leu Ser Asn Pro Thr Xaa
1               5

( 2 ) INFORMATION FOR SEQ ID NO:129:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:129:

Leu Ser Asn Pro Thr Xaa Ser Val 1 5

(2) INFORMATION FOR SEQ ID NO:130:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:130:

Leu Ser Asn Pro Thr Xaa Ala Val
    1               5

(2) INFORMATION FOR SEQ ID NO:131:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:131:

Leu Ser Asn Ala Thr Xaa Ser Val
    1               5

(2) INFORMATION FOR SEQ ID NO:132:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:132:

Leu Ala Asn Pro Thr Xaa Ser Val
    1               5

(2) INFORMATION FOR SEQ ID NO:133:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:133:

Ala Ser Asn Pro Thr Xaa Ser Val
    1               5

(2) INFORMATION FOR SEQ ID NO:134:

(i) SEQUENCE CHARACTERISTICS:
        (A) LENGTH: 15 amino acids
        (B) TYPE: amino acid
        (D) TOPOLOGY: linear (ii) MOLECULE TYPE: peptide ( v ) FRAGMENT TYPE: internal ( x i ) SEQUENCE DESCRIPTION: SEQ ID NO:134:

Leu Tyr Ala Ser Ser Asn Pro Glu Xaa Leu Ser Ala Ser Asp Val
1               5                   10                  15

( 2 ) INFORMATION FOR SEQ ID NO:135:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:135:

Tyr Ala Ser Ser Asn Pro Glu Xaa Leu Ser Ala Ser Asp Val
1               5                   10

( 2 ) INFORMATION FOR SEQ ID NO:136:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:136:

Leu Tyr Ala Ser Ser Asn Pro Ala Xaa Leu Ser Ala Ser Asp Val
1               5                   10                  15

( 2 ) INFORMATION FOR SEQ ID NO:137:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:137:

Leu Tyr Ala Ser Ser Asn Ala Glu Xaa Leu Ser Ala Ser Asp Val
1               5                   10                  15

( 2 ) INFORMATION FOR SEQ ID NO:138:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:138:

Leu Tyr Ala Ser Ser Ala Pro Glu Xaa Leu Ser Ala Ser Asp Val
1               5                   10                  15

( 2 ) INFORMATION FOR SEQ ID NO:139:

( i ) SEQUENCE CHARACTERISTICS:
      ( A ) LENGTH: 15 amino acids (B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:139:

Leu Tyr Ala Ser Ala Asn Pro Glu Xaa Leu Ser Ala Ser Asp Val
1               5                   10                  15

(2) INFORMATION FOR SEQ ID NO:140:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:140:

Leu Tyr Ala Ala Ser Asn Pro Glu Xaa Leu Ser Ala Ser Asp Val
1               5                   10                  15

(2) INFORMATION FOR SEQ ID NO:141:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:141:

Leu Tyr Val Ser Ser Asn Pro Glu Xaa Leu Ser Ala Ser Asp Val
1               5                   10                  15

(2) INFORMATION FOR SEQ ID NO:142:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:142:

Leu Ala Ala Ser Ser Asn Pro Glu Xaa Leu Ser Ala Ser Asp Val
1               5                   10                  15

(2) INFORMATION FOR SEQ ID NO:143:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:143:

Ala Tyr Ala Ser Ser Asn Pro Glu Xaa Leu Ser Ala Ser Asp Val
1               5                   10                  15

( 2 ) INFORMATION FOR SEQ ID NO:144:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:144:

Ile  Glu  Asn  Pro  Gln  Xaa  Phe  Ser
    1                       5

( 2 ) INFORMATION FOR SEQ ID NO:145:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:145:

Glu  Pro  Gln  Xaa  Glu  Glu  Ile  Asn  Ile  Tyr  Leu
    1                     5                                10

( 2 ) INFORMATION FOR SEQ ID NO:146:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: misc_feature
        ( B ) LOCATION: Residue No. 1
        ( C ) OTHER INFORMATION: Xaa = Ac- Q ( i x ) FEATURE:
        ( A ) NAME/KEY: misc_feature
        ( B ) LOCATION: Residue No. 2
        ( C ) OTHER INFORMATION: (D/L)F2Pmp ( i x ) FEATURE:
        ( A ) NAME/KEY: misc_feature
        ( B ) LOCATION: Residue No. 6
        ( C ) OTHER INFORMATION: Xaa = P- NH2

( x i ) SEQUENCE DESCRIPTION: SEQ ID NO:146:

Xaa  Xaa  Glu  Glu  Ile  Xaa
    1                       5

( 2 ) INFORMATION FOR SEQ ID NO:147:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: misc_feature ( B ) LOCATION: Residue No. 1
                    ( C ) OTHER INFORMATION: Xaa = Ac- Q ( i x ) FEATURE:
                    ( A ) NAME/KEY: misc_feature
                    ( B ) LOCATION: Residue No. 2
                    ( C ) OTHER INFORMATION: (L)F2Pmp ( i x ) FEATURE:
                    ( A ) NAME/KEY: misc_feature
                    ( B ) LOCATION: Residue No. 6
                    ( C ) OTHER INFORMATION: Xaa = P- NH2

( x i ) SEQUENCE DESCRIPTION: SEQ ID NO:147:

Xaa  Xaa  Glu  Glu  Ile  Xaa
        1                  5

( 2 ) INFORMATION FOR SEQ ID NO:148:

( i ) SEQUENCE CHARACTERISTICS:
                    ( A ) LENGTH: 5 amino acids
                    ( B ) TYPE: amino acid
                    ( D ) TOPOLOGY: linear ( i i ) MOLECULE TYPE: peptide ( v ) FRAGMENT TYPE: internal ( x i ) SEQUENCE DESCRIPTION: SEQ ID NO:148:

Xaa  Xaa  Glu  Glu  Xaa
        1                  5

( 2 ) INFORMATION FOR SEQ ID NO:149:

( i ) SEQUENCE CHARACTERISTICS:
                    ( A ) LENGTH: 12 amino acids
                    ( B ) TYPE: amino acid
                    ( D ) TOPOLOGY: linear ( i i ) MOLECULE TYPE: peptide ( v ) FRAGMENT TYPE: internal ( x i ) SEQUENCE DESCRIPTION: SEQ ID NO:149:

Lys  Glu  Pro  Gln  Xaa  Glu  Glu  Ile  Pro  Ile  Tyr  Leu
        1                  5                              10

( 2 ) INFORMATION FOR SEQ ID NO:150:

( i ) SEQUENCE CHARACTERISTICS:
                    ( A ) LENGTH: 11 amino acids
                    ( B ) TYPE: amino acid
                    ( D ) TOPOLOGY: linear ( i i ) MOLECULE TYPE: peptide ( v ) FRAGMENT TYPE: internal ( x i ) SEQUENCE DESCRIPTION: SEQ ID NO:150:

Lys  His  Gln  Xaa  Glu  Glu  Ile  Pro  Ile  Tyr  Leu
        1                  5                         10

( 2 ) INFORMATION FOR SEQ ID NO:151:

( i ) SEQUENCE CHARACTERISTICS:
                    ( A ) LENGTH: 11 amino acids
                    ( B ) TYPE: amino acid
                    ( D ) TOPOLOGY: linear ( i i ) MOLECULE TYPE: peptide ( v ) FRAGMENT TYPE: internal ( i x ) FEATURE:
  ( A ) NAME/KEY: misc_feature
  ( B ) LOCATION: Residue No. 4
  ( C ) OTHER INFORMATION: Xaa =sY ( x i ) SEQUENCE DESCRIPTION: SEQ ID NO:151:

Glu Pro Gln Xaa Glu Glu Ile Pro Ile Tyr Leu
1               5                   10

( 2 ) INFORMATION FOR SEQ ID NO:152:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:152:

Asp His Gln Xaa Tyr Asn Asp Met Pro Gly Lys
1               5                   10

( 2 ) INFORMATION FOR SEQ ID NO:153:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:153:

Asp His Gln Tyr Xaa Asn Asp Met Pro Gly Lys
1               5                   10

( 2 ) INFORMATION FOR SEQ ID NO:154:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:154:

Glu Leu Phe Asp Asp Pro Ser Xaa Val Asn Val Gln Asn Leu Asp Lys
1               5                   10                  15

( 2 ) INFORMATION FOR SEQ ID NO:155:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:155:

Pro Ser Xaa Val Gln Val Gln Asn Leu
1               5

( 2 ) INFORMATION FOR SEQ ID NO:156:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:156:

```
Pro  Ser  Xaa  Val  Asn  Val  Gln  Asn  Leu
1                  5
```

( 2 ) INFORMATION FOR SEQ ID NO:157:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:157:

```
Pro  Ser  Xaa  Val  Asn  Val  Gln  Asn
1                  5
```

( 2 ) INFORMATION FOR SEQ ID NO:158:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:158:

```
Xaa  Val  Asn  Val  Xaa
1                  5
```

( 2 ) INFORMATION FOR SEQ ID NO:159:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:159:

```
Xaa  Xaa  Val  Asn  Xaa
1                  5
```

( 2 ) INFORMATION FOR SEQ ID NO:160:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:160:

```
           Ser  Xaa  Val  Asn  Xaa
           1                  5
```

( 2 ) INFORMATION FOR SEQ ID NO:161:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:161:

```
           Xaa  Val  Asn  Xaa
           1
```

( 2 ) INFORMATION FOR SEQ ID NO:162:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:162:

```
           Xaa  Xaa  Val  Xaa
           1
```

( 2 ) INFORMATION FOR SEQ ID NO:163:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:163:

```
           Ser  Xaa  Val  Xaa
           1
```

( 2 ) INFORMATION FOR SEQ ID NO:164:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:164:

```
           Xaa  Val  Xaa
           1
```

( 2 ) INFORMATION FOR SEQ ID NO:165:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:165:

```
Leu Asn Xaa Ile Asp Leu Asp Leu Xaa
1               5
```

( 2 ) INFORMATION FOR SEQ ID NO:166:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:166:

```
Leu Asn Xaa Ile Xaa
1               5
```

( 2 ) INFORMATION FOR SEQ ID NO:167:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:167:

```
Xaa Xaa Ile Asp Leu Asp Xaa
1               5
```

( 2 ) INFORMATION FOR SEQ ID NO:168:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:168:

```
Asn Xaa Ile Asp Leu Asp Xaa
1               5
```

( 2 ) INFORMATION FOR SEQ ID NO:169:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:169:

```
Xaa Ile Asp Leu Asp Xaa
1               5
```

( 2 ) INFORMATION FOR SEQ ID NO:170:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: misc_feature
    ( B ) LOCATION: Residue No. 1
    ( C ) OTHER INFORMATION: Xaa = Ac- A ( i x ) FEATURE:
    ( A ) NAME/KEY: misc_feature
    ( B ) LOCATION: Residue No. 2
    ( C ) OTHER INFORMATION: pY ( i x ) FEATURE:
    ( A ) NAME/KEY: misc_feature
    ( B ) LOCATION: Residue No. 8
    ( C ) OTHER INFORMATION: Xaa = D- NH2

( x i ) SEQUENCE DESCRIPTION: SEQ ID NO:170:

Xaa Xaa Asp Ile Pro Leu Pro Xaa
1                   5

( 2 ) INFORMATION FOR SEQ ID NO:171:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:171:

Asn Gly Asp Xaa Met Pro Met Ser Pro Lys Xaa
1                   5                        10

( 2 ) INFORMATION FOR SEQ ID NO:172:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:172:

Gly Asp Xaa Met Pro Met Ser Pro Lys Xaa
1               5                       10

( 2 ) INFORMATION FOR SEQ ID NO:173:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:173:

Xaa Xaa Met Pro Met Ser Pro Lys Xaa
1                   5

( 2 ) INFORMATION FOR SEQ ID NO:174:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:174:

Asp  Xaa  Met  Pro  Met  Ser  Pro  Lys  Xaa
    1                          5

( 2 ) INFORMATION FOR SEQ ID NO:175:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: misc_feature
        ( B ) LOCATION: Residue No. 1
        ( C ) OTHER INFORMATION: Xaa = Ac- pY ( i x ) FEATURE:
        ( A ) NAME/KEY: misc_feature
        ( B ) LOCATION: Residue No. 8
        ( C ) OTHER INFORMATION: S-OH ( x i ) SEQUENCE DESCRIPTION: SEQ ID NO:175:

Xaa  Met  Pro  Met  Ser  Pro  Lys  Xaa
    1                      5

( 2 ) INFORMATION FOR SEQ ID NO:176:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: misc_feature
        ( B ) LOCATION: Residue No. 1
        ( C ) OTHER INFORMATION: Xaa =pY ( i x ) FEATURE:
        ( A ) NAME/KEY: misc_feature
        ( B ) LOCATION: Residue No. 8
        ( C ) OTHER INFORMATION: S-OH ( x i ) SEQUENCE DESCRIPTION: SEQ ID NO:176:

Xaa  Met  Pro  Met  Ser  Pro  Lys  Xaa
    1                      5

( 2 ) INFORMATION FOR SEQ ID NO:177:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:177:

Xaa Met Pro Met Ser Xaa
1               5

( 2 ) INFORMATION FOR SEQ ID NO:178:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:178:

Xaa Met Pro Met Xaa
1               5

( 2 ) INFORMATION FOR SEQ ID NO:179:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:179:

Xaa Met Pro Xaa
1

( 2 ) INFORMATION FOR SEQ ID NO:180:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:180:

Xaa Met Pro Met Ser Pro Ala Xaa
1               5

( 2 ) INFORMATION FOR SEQ ID NO:181:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:181:

Xaa Met Pro Met Ser Ala Lys Xaa
1               5

( 2 ) INFORMATION FOR SEQ ID NO:182:

( i ) SEQUENCE CHARACTERISTICS:

( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:182:

Xaa Met Pro Met Ala Pro Lys Xaa
    1               5

( 2 ) INFORMATION FOR SEQ ID NO:183:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:183:

Xaa Met Ala Met Ser Pro Lys Xaa
    1               5

( 2 ) INFORMATION FOR SEQ ID NO:184:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:184:

Xaa Ala Pro Met Ser Pro Lys Xaa
    1               5

( 2 ) INFORMATION FOR SEQ ID NO:185:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:185:

Ser Leu Asn Xaa Ile Asp Leu Asp Leu Val Lys
    1               5                       10

( 2 ) INFORMATION FOR SEQ ID NO:186:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:186:

Asn Tyr Ile Asp Leu Asp Leu
    1               5

( 2 ) INFORMATION FOR SEQ ID NO:187:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:187:

```
Tyr  Ile  Asp  Leu  Asp  Leu
1                  5
```

( 2 ) INFORMATION FOR SEQ ID NO:188:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:188:

```
Asp  Tyr  Ile  Ile  Pro  Leu  Pro  Asp
1                  5
```

( 2 ) INFORMATION FOR SEQ ID NO:189:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:189:

```
Asp  Tyr  Ile  Ile  Pro  Leu  Pro  Arg
1                  5
```

( 2 ) INFORMATION FOR SEQ ID NO:190:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:190:

```
Asp  Tyr  Ile  Ile  Pro  Leu  Asp  Asp
1                  5
```

( 2 ) INFORMATION FOR SEQ ID NO:191:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:191:

Asp Tyr Ile Ile Pro Asp Pro Asp
1               5

( 2 ) INFORMATION FOR SEQ ID NO:192:

( i ) SEQUENCE CHARACTERISTICS:
       ( A ) LENGTH: 8 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:192:

Asp Tyr Ile Ile Asp Leu Pro Asp
1               5

( 2 ) INFORMATION FOR SEQ ID NO:193:

( i ) SEQUENCE CHARACTERISTICS:
       ( A ) LENGTH: 8 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:193:

Asp Tyr Ile Asp Pro Leu Pro Asp
1               5

( 2 ) INFORMATION FOR SEQ ID NO:194:

( i ) SEQUENCE CHARACTERISTICS:
       ( A ) LENGTH: 8 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:194:

Asp Tyr Asp Ile Pro Leu Pro Asp
1               5

( 2 ) INFORMATION FOR SEQ ID NO:195:

( i ) SEQUENCE CHARACTERISTICS:
       ( A ) LENGTH: 8 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:195:

Ala Tyr Asp Ile Pro Leu Pro Asp
1               5

( 2 ) INFORMATION FOR SEQ ID NO:196:

( i ) SEQUENCE CHARACTERISTICS:
       ( A ) LENGTH: 11 amino acids
       ( B ) TYPE: amino acid (D) TOPOLOGY: linear (ii) MOLECULE TYPE: peptide (v) FRAGMENT TYPE: internal (xi) SEQUENCE DESCRIPTION: SEQ ID NO:196:

Asn Gly Asp Tyr Met Pro Met Ser Pro Lys Ser
1               5                   10

(2) INFORMATION FOR SEQ ID NO:197:

(i) SEQUENCE CHARACTERISTICS:
    (A) LENGTH: 10 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:197:

Gly Asp Tyr Met Pro Met Ser Pro Lys Ser
1               5                   10

(2) INFORMATION FOR SEQ ID NO:198:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:198:

Asp Tyr Met Pro Met Ser Pro Lys Ser
1               5

(2) INFORMATION FOR SEQ ID NO:199:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:199:

Asp Tyr Met Pro Met Ser Pro Lys Ser
1               5

(2) INFORMATION FOR SEQ ID NO:200:

(i) SEQUENCE CHARACTERISTICS:
    (A) LENGTH: 8 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO:200:

Tyr Met Pro Met Ser Pro Lys Ser
1               5

( 2 ) INFORMATION FOR SEQ ID NO:201:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:201:

Tyr Met Pro Met Ser Pro Lys Ser
1               5

( 2 ) INFORMATION FOR SEQ ID NO:202:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:202:

Tyr Met Pro Met Ser Pro
1               5

( 2 ) INFORMATION FOR SEQ ID NO:203:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:203:

Tyr Met Pro Met Ser
1               5

( 2 ) INFORMATION FOR SEQ ID NO:204:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:204:

Tyr Met Pro Met
1

( 2 ) INFORMATION FOR SEQ ID NO:205:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:205:

```
        Tyr  Met  Pro  Met  Ser  Pro  Lys  Ser
        1                  5
```

( 2 ) INFORMATION FOR SEQ ID NO:206:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:206:

```
        Tyr  Met  Pro  Met  Ser  Pro  Ala  Ser
        1                  5
```

( 2 ) INFORMATION FOR SEQ ID NO:207:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:207:

```
        Tyr  Met  Pro  Met  Ser  Ala  Lys  Ser
        1                  5
```

( 2 ) INFORMATION FOR SEQ ID NO:208:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:208:

```
        Tyr  Met  Pro  Met  Ala  Pro  Lys  Ser
        1                  5
```

( 2 ) INFORMATION FOR SEQ ID NO:209:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:209:

```
        Tyr  Met  Ala  Met  Ser  Pro  Lys  Ser
        1                  5
```

( 2 ) INFORMATION FOR SEQ ID NO:210:

( i ) SEQUENCE CHARACTERISTICS:
        ( A ) LENGTH: 8 amino acids
        ( B ) TYPE: amino acid
        ( D ) TOPOLOGY: linear (i i) MOLECULE TYPE: peptide (v) FRAGMENT TYPE: internal (x i) SEQUENCE DESCRIPTION: SEQ ID NO:210:

Tyr Ala Pro Met Ser Pro Lys Ser
    1               5

(2) INFORMATION FOR SEQ ID NO:211:

(i) SEQUENCE CHARACTERISTICS:
        (A) LENGTH: 11 amino acids
        (B) TYPE: amino acid
        (D) TOPOLOGY: linear (i i) MOLECULE TYPE: peptide (v) FRAGMENT TYPE: internal (x i) SEQUENCE DESCRIPTION: SEQ ID NO:211:

Ser Leu Asn Tyr Ile Asp Leu Asp Leu Val Lys
    1               5                   1 0